(12) United States Patent
Gaczynska et al.

US011345659B2

(10) Patent No.: US 11,345,659 B2
(45) Date of Patent: May 31, 2022

(54) PIPECOLIC ESTERS FOR INHIBITION OF THE PROTEASOME

(71) Applicants: THE BOARD OF REGENTS OF THE UNIVERSY OF TEXAS SYSTEM, Austin, TX (US); BOARD OF TRUSTEES OF MICHIGAN STATE UNIVERSITY, East Lansing, MI (US)

(72) Inventors: Maria Gaczynska, San Antonio, TX (US); Pawel A. Osmulski, San Antonio, TX (US); Jetze Tepe, East Lansing, MI (US); Matt Giletto, Lansing, MI (US)

(73) Assignees: BOARD OF REGENTS, THE UNIVERSITY OF TEXAS SYSTEM, Austin, TX (US); BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 16/965,276

(22) PCT Filed: Jan. 30, 2019

(86) PCT No.: PCT/US2019/015864
§ 371 (c)(1),
(2) Date: Jul. 27, 2020

(87) PCT Pub. No.: WO2019/152527
PCT Pub. Date: Aug. 8, 2019

(65) Prior Publication Data
US 2021/0002220 A1 Jan. 7, 2021

Related U.S. Application Data

(60) Provisional application No. 62/623,861, filed on Jan. 30, 2018.

(51) Int. Cl.
*C07D 207/16* (2006.01)
*C07D 211/60* (2006.01)

(52) U.S. Cl.
CPC .......... *C07D 207/16* (2013.01); *C07D 211/60* (2013.01)

(58) Field of Classification Search
CPC .................................................. C07D 211/60
See application file for complete search history.

(56) References Cited

U.S. PATENT DOCUMENTS

| 5,506,256 | A | 4/1996 | Kobayashi et al. | |
|---|---|---|---|---|
| 5,620,971 | A | 4/1997 | Armistead et al. | |
| 6,335,348 | B1 | 1/2002 | Ross et al. | |
| 6,376,517 | B1 | 4/2002 | Ross et al. | |
| 6,544,987 | B2 * | 4/2003 | Guo | C07D 513/04 514/231.5 |
| 7,056,935 | B2 | 6/2006 | Steiner et al. | |
| 7,265,150 | B1 | 9/2007 | Ross et al. | |
| 7,550,603 | B2 * | 6/2009 | Zhu | A61P 29/00 548/304.7 |
| 2014/0356785 | A1 | 12/2014 | Williams, III et al. | |

FOREIGN PATENT DOCUMENTS

| EP | 14811064.6 | 6/2014 | |
|---|---|---|---|
| EP | 3007696 | 4/2016 | |
| WO | WO 2002/096420 A2 | 12/2002 | |
| WO | WO 2012/075048 A2 | 6/2012 | |
| WO | WO-2013007371 A2 * | 1/2013 | ........... C07D 265/30 |
| WO | WO 2013/091900 A1 | 6/2013 | |
| WO | PCT/US2014/042383 | 6/2014 | |
| WO | WO 2014/201405 | 12/2014 | |
| WO | PCT/US2019/015864 | 1/2019 | |
| WO | WO 2019/152527 | 8/2019 | |

OTHER PUBLICATIONS

Penning et al., "Discovery of the, etc.," J. Med. Chem., 52, 514-523. (Year: 2009).*
Sadiq et al., "(R)-alpha-Aminoadipic, etc.," Arkivoc(v) 28-36. (Year: 2012).*
Kreituss et al. CA 166:395165. (Year: 2016).*
Al-Momani. Inorganica Chimica Acta, 2013, 394, 176-183. (Year: 2013).*
Andre et al. (1998) "An inhibitor of HIV-1 protease modulates proteasome activity, antigen presentation, and T cell responses" *Proceedings of the National Academy of Sciences of the United States of America* 95: 13120-13124.
Babbitt, et al. (2005) "ATP hydrolysis-dependent disassembly of the 26S proteasome is part of the catalytic cycle" *Cell* 121: 553-65.
Bar-Nun and Glickman (2012) "Proteasomal AAA-ATPases: structure and function" *Biochimica et biophysica acta* 1823: 67-82.
Busse, et al. (2008) "Sensitivity of tumor cells to proteasome inhibitors is associated with expression levels and composition of proteasome subunits" *Cancer* 112: 659-670.
Chen et al. (2016) "Structural basis for dynamic regulation of the human 26S proteasome" *Proc. Natl. Acad. Sci.* 113(46): 12991-6.
Chen and Madura (2005) "Increased proteasome activity, ubiquitin-conjugating enzymes, and eEF1A translation factor detected in breast cancer tissue" *Cancer Res.* 65; 5599-5606.
Crawford, et al. (2011) "Proteasome inhibitors in cancer therapy" *J. Cell Commun. Signal.* 5: 101-110.
Dong et al. (2010) "Cryo-EM structures and dynamics of substrate-engaged human 26S proteasome" *Nature* 565(7737): 49-55.
Finley et al. (2016) "Gates, Channels, and Switches: Elements of the Proteasome Machine" *Trends Biochem. Sci.* 41: 77-93.

(Continued)

*Primary Examiner* — Noble E Jarrell
(74) *Attorney, Agent, or Firm* — Ballard Spahr LLP

(57) ABSTRACT

The present disclosure relates to chemical compounds that modulate proteasome activity, pharmaceutical compositions containing such compounds, and use of these compounds and compositions for the treatment of disorders of uncontrolled cellular proliferation such as, for example, a cancer. This abstract is intended as a scanning tool for purposes of searching in the particular art and is not intended to be limiting of the present invention.

7 Claims, 11 Drawing Sheets

Specification includes a Sequence Listing.

(56) References Cited

OTHER PUBLICATIONS

Forster et al. (2005) "The 1.9 A structure of a proteasome-11S activator complex and implications for proteasome-PAN/PA700 interactions" *Mol. Cell* 18(5): 589-99.
Gaczynska and Osmulski (2009) "A tetrahedral transition state at the active sites of the 20S proteasome is coupled to opening of the alpha-ring channel" Atomic Force Microscopy as a Tool to Study the Proteasome Assemblies; Osmulski et al. (2009) *Structure* 17(8): 1137-1147.
Gizynska et al. (2019) "Proline- and Arginine-Rich Peptides as Flexible Allosteric Modulators of Human Proteasome Activity" *J. Med. Chem.* 62(1): 359-70.
Glickman and Ciechanover (2002) "The ubiquitin-proteasome proteolytic pathway: destruction for the sake of construction" *Physiol. Rev.* 82: 373-428.
Jankowska, et al. (2010) "Potential allosteric modulators of the proteasome activity" *Biopolymers* 93: 481.
Jones et al. (2017) "Small Molecule Enhancement of 20S Proteasome Activity Targets Intrinsically Disordered Proteins" *ACS CHem. Biol.* 12(9): 2240-2247.
Kisselev, et al. (2003) "The caspase-like sites of proteasomes, their substrate specificity, new inhibitors and substrates, and allosteric interactions with the trypsin-like sites" *J. Biol. Chem.* 278: 35869-77.
Lander et al. (2012) "Complete subunit architecture of the proteasome regulatory particle" *Nature* 482(7384): 186-91.
Liu, et al. (2006) "ATP binding and ATP hydrolysis play distinct roles in the function of 26S proteasome" *Molecular Cell* 24: 39-50.
Madura, K. (2009) "Cell biology: The proteasome assembly line" *Nature* 259: 787-788.
Njomen et al. (2018) "Small Molecule Modulation of Proteasome Assembly" *Biochemistry* 57(28): 4214-24.
Orlowski and Kuhn (2008) "Proteasome inhibitors in cancer therapy: lessons from the first decade" *Clinical Cancer Research* 14: 1649-1657.
Osmulski et al. (2009) "A tetrahedral transition state at the active sites of the 20S proteasome is coupled to opening of the alpha-ring channel" *Structure* 17: 1137-1147.
Osmulski and Gaczynska (2000) "Atomic force microscopy reveals two conformations of the 20 S proteasome from fission yeast" *J. Biol. CHem.* 275: 13171-13174.
Osmulski and Gaczynska (2002) "Nanoenzymology of the 20S proteasome: proteasomal actions are controlled by the allosteric transition" *Biochemistry* 41(22): 7047-53.
Vignot et al. (2005) "mTOR-targeted therapy of cancer with rapamycin derivatives" *Ann. Oncol.* 16: 525-537.
Yang, et al. (2006) "Bortezomib (VELCADE) in metastatic breast cancer: pharmacodynamics, biological effects, and prediction of clinical benefits" *Ann. Oncol.* 17(5): 813-817.
International Search Report and Written Opinion dated Aug. 8, 2019 by the International Searching Authority for International Application No. PCT/US2019/015864, filed on Jan. 30, 2019, and published as WO 2019/152527 on Aug. 8, 2019 (Applicant—The Board of Regents of The University of Texas System) (14 Pages).
International Search Report dated Dec. 18, 2014 by the International Searching Authority for International Application No. PCT/US2014/042383, filed on Jun. 13, 2014, and published as WO 2014/201405 on Dec. 18, 2014 (Applicant—The Board of Regents of The University of Texas System) (7 Pages).
Written Opinion dated Dec. 14, 2015 by the International Searching Authority for International Application No. PCT/US2014/042383, filed on Jun. 13, 2014, and published as WO 2014/201405 on Dec. 18, 2014 (Applicant—The Board of Regents of The University of Texas System) (5 Pages).
International Preliminary Report on Patentability dated Dec. 15, 2015 by the International Searching Authority for International Application No. PCT/US2014/042383, filed on Jun. 13, 2014, and published as WO 2014/201405 on Dec. 18, 2014 (Applicant—The Board of Regents of The University of Texas System) (6 Pages).

Supplementary European Search Report dated Aug. 30, 2017 by the European Patent Office for EP Application No. 14811064.6, filed on Jun. 13, 2014, and published as 3007696 on Apr. 20, 2016 (Applicant—The Board of Regents of The University of Texas System) (12 Pages).
Nakatsuji et al. (2007) "Mild, powerful, and robust methods for esterification, amide formation, and thioesterification between acid chlorides and alcohols, amines, thiols, respectively," *Tetrahedron* 63(48): 12071-12080.
Shinada et al. (2000) "Squaric Acid Derivatives Prevent the Removal of N-Cbz and N-Fmoc Groups under Catalytic Hydrogenation Reaction," *Synlett* 10: 1506-1508.
Adams, J. (2004) "The proteasome: a suitable antineoplastic target" *Nat. Rev. Cancer* 4: 349-360.
Sezen (2005) "Selective and catalytic arylation of N-phenylpyrrolidine: (sp3) C—H bond functionalization in the absence of a directing group " *J. Am. Chem. Soc.* 127: 5284-5.
Dallakyan and Olson (2015) "Small-molecule library screening by docking with PyRx" *Methods Mol. Biol.* 1263: 243-250.
De Bettignies and Coux (2010) "Proteasome inhibitors: Dozens of molecules and still counting" *Biochimie* 92: 1530.
Engel, et al. (2007) "A phase II study of single agent bortezomib in patients with metastatic breast cancer: a single institution experience" *Cancer Investigation* 25: 733-737.
Gaczynska et al. (2003) "Proline- and arginine-rich peptides constitute a novel class of allosteric inhibitors of proteasome activity" *Biochemistry* 42: 8663-8670.
Gaczynska and Osmulski (2008) "Atomic force microscopy as a tool to study the proteasome assemblies" *Methods Cell Biol.* 90: 39-60.
Gaczynska and Osmulski (2011) "Atomic force microscopy of proteasome assemblies" *Methods Mol. Biol.* 736: 117-32.
Goodey and Benjovic (2008) "Allosteric regulation and catalysis emerge via a common route" *Nature Chemical Biology* 4: 474-482.
Gopalakrishnan, et al. (2012) "Evaluation of synthetic FK506 analogues as ligands for the FK506-binding proteins 51 and 52" *Journal of Medicinal Chemistry* 55(9): 4114-4122.
Groll et al. (2005) "Molecular machines for protein degradation" *Chembiochem* 6: 222-256.
Groll et al. (2006) "Crystal structures of Salinosporamide A (NPI-0052) and B (NPI-0047) in complex with the 20S proteasome reveal important consequences of beta-lactone ring opening and a mechanism for irreversible binding" *J. Am. Chem. Soc.* 128:5136-5141.
Groll and Potts (2011) "Proteasome structure, function, and lessons learned from beta-lactone inhibitors" *Curr. Top. Med. Chem.* 11: 2850-2878.
Gunasekaran, et al. (2004) "Is allostery an intrinsic property of all dynamic proteins?" *Proteins* 57: 433.
Hamilton, et al. (1998) "Immunophilins: beyond immunosuppression" *Journal of Medicinal Chemistry* 41 (26): 5119-5143.
Hamilton, et al. (2002) "Synthesis of N-glyoxyl prolyl and pipecolyl amides and thioesters and evaluation of their in vitro and in vivo nerve regenerative effects" *ournal of Medicinal Chemistry* 45(16): 3549-3557.
Holt, et al. (1993) "Design, synthesis, and kinetic evaluation of high-affinity FKBP ligands and the X-ray crystal structures of their complexes with FKBP12" *Journal of the American Chemical Society* 115(22): 9925-9938.
Huang et al. (2016) "An atomic structure of the human 26S proteasome" *Nat. Struct. Mol. Biol.* 23: 778-785.
Jankowska et al. (2013) "The proteasome in health and disease" *Current pharmaceutical design* 19: 1010-1028.
Klejinen, et al. (2007) "Stability of the proteasome can be regulated allosterically through engagement of its proteolytic active sites" *Nature Structural & Molecular Biology* 14: 1180-1188.
Kraus, et al. (2007) "Activity patterns of proteasome subunits reflect bortezomib sensitivity of hematologic malignancies and are variable in primary human leukemia cells" *Leukemia* 21: 84-92.
Kuhn et al. (2011) "Second generation proteasome inhibitors: carfilzomib and immunoproteasome-specific inhibitors (IPSIs)" *Curr. Cancer Drug Targets* 11: 285-295.
PubChem CID 2385813, created Jul. 15, 2005.
PubChem CID 9967728, created Oct. 25, 2006.

(56) References Cited

OTHER PUBLICATIONS

PubChem 12000171, created Feb. 5, 2007.
Rodriguez, et al. (2010) "Molecular mechanisms of proteasome plasticity in aging" *Mech Ageing Dev* 131(2): 144-155.
Rosenzweig, et al. (2008) "The central unit within the 19S regulatory particle of the proteasome" *Nat Struct Mol Biol* 15(6): 573-580.
Schweitzer, et al. (2016) "Structure of the human 26S proteasome at a resolution of 3.9 Å" PNAS 113(28): 7816-7821.
Smith, et al. (2007) "Docking of the Proteasomal ATPases' C-termini in the 20S Proteasomes alpha Ring Opens the Gate for Substrate Entry" *Mol Cell* 27(5): 731-744.
Stadtmueller, et al. (2010) "Structural models for interactions between the 20S proteasome and its PAN/19S activators" *The Journal of Biological Chemistry* 285(1): 13-17.
Trott and Olsen (2010) "AutoDock Vina: improving the speed and accuracy of docking with a new scoring function, efficient optimization and multithreading" *J Comput Chem* 31(2): 455-461.
Whitehurst, et al. (2007) "Synthetic lethal screen identification of chemosensitizer loci in cancer cells" *Nature* 446: 815-819.
Yamaguchi, et al. (2009) *Cancer Science* 100: 1668-1674.
U.S. Appl. No. 62/623,861, filed Jan. 30, 2018, Maria Gaczynska.
U.S. Appl. No. 61/835,221, filed Jun. 14, 2013, Maria Gaczynska.
U.S. Appl. No. 14/896,984, filed Jun. 13, 2014, Maria Gaczynska.

\* cited by examiner

PIPECOLIC ESTERS FOR INHIBITION OF THE PROTEASOME

CROSS-REFERENCE TO RELATED APPLICATIONS

This Application is a national stage filing under 35 U.S.C. § 371 of International Application No. PCT/US2019/015864, filed on Jan. 30, 2019, which claims the benefit of U.S. Provisional Application No. 62/623,861, filed on Jan. 30, 2018, the contents of which are incorporated herein by reference in their entireties.

REFERENCE TO SEQUENCE LISTING

The Sequence Listing submitted Jul. 27, 2020 as a text file named "21105_0050U2_ST25.txt," created on Jul. 20, 2020, and having a size of 543 bytes is hereby incorporated by reference pursuant to 37 C.F.R. § 1.52(e)(5).

BACKGROUND

The proteasome is an essential protease that regulates intracellular processes and maintains biological homeostasis through the proteolytic degradation of misfolded and redundant proteins (Glickman et al. (2002) *Physiol. Rev.* 82: 373-428). Inhibition of the proteasome induces apoptosis, which has translated in the clinic as a means to treat various cancers, most notably multiple myeloma and mantle cell lymphoma (Jankowska et al. (2013) *Current pharmaceutical design* 19: 1010-1028; Adams, J. (2004) *Nat. Rev. Cancer* 4: 349-360; Kuhn et al. (2011) *Curr. Cancer Drug Targets* 11: 285-295). The activities of the proteasome, the essential, multifunctional human proteolytic assembly, are not infrequently found to be affected by compounds with non-proteasomal primary targets. For example, this is the case with chloroquine (Sprangers et al. (2008) *Biochemistry* 47: 6727-6734), proline and arginine rich peptides (Gaczynska et al. (2003) *Biochemistry* 42: 8663-8670), and ritonavir (Andre et al. (1998) *Proceedings of the National Academy of Sciences of the United States of America* 95: 13120-13124). Recently, it was found that the natural product and established immunosuppressive drug rapamycin allosterically inhibits the human 20 S proteasome (Osmulski and Gaczynska (2013) *Molecular pharmacology* 84: 104-113). Rapamycin and its close homologs are used as anti-cancer drugs (rapalogs) (Vignot et al. (2005) *Ann. Oncol.* 16: 525-537) and are macrocyclic compounds sharing common "binding" and "effector" domains. The former domain promotes dimerization of mTOR (mammalian/mechanistic target of rapamycin) and FKBP12 (FK-binding protein 12), whereas the latter allosterically inhibits the kinase activity of mTOR (Liang et al. (1999) *Acta Crystallogr. D. Biol. Cyrstallogr.* 55: 736-744; Banaszynski et al. (2005) *J. Am. Chem. Soc.* 127: 4715-4721). The mTOR signaling pathway is one of the major regulators of intracellular homeostasis (Ma et al. (2009) *Nat. Rev. Mol. Cell Biol.* 10: 307-318). The anti-proteasome actions of rapamycin are exerted at much higher concentrations than the mTOR inhibition and thus would have no physiological relevance, if not for some additional important observations. Namely, it was determined that the rapamycin metabolite seco-rapamycin with the macrocyclic ring open still inhibits the proteasome while not affecting the mTOR pathway (Osmulski and Gaczynska (2013) *Molecular pharmacology* 84: 104-113). Thus, the development of a novel proteasome-targeting pharmacophore is desirable.

The 26 S proteasome is the most common form of the human proteasome, which consists of a 20 S core particle (required for substrate proteolysis) and two 19 S regulatory particles (required for substrate recognition and unfolding) (Huang et al. (2016) *Nat. Struct. Mol. Biol.* 23: 778-785; Finley et al. (2016) *Trends Biochem. Sci.* 41: 77-93). At least one 19 S module is required to allow the proteasome to process substrates tagged for degradation by chains of small protein ubiquitin (Glickman and Ciechanover (2002) *Physiol. Rev.* 82: 373-428). The 20 S proteasome is a barrel-shaped multisubunit complex composed of 28 subunits arranged in four stacked heptameric rings. The inner β-rings contain three catalytic subunits (β5, β2, and β1) that exhibit chymotrypsin-like (ChT-L), trypsin-like (T-L) and caspase-like (Casp-L) proteolytic activities, respectively, cleaving on carboxyl side of hydrophobic (and branched), basic and acidic (and small neutral) amino acids (Groll et al. (2005) *Chembiochem* 6: 222-256). The outer α-rings do not exhibit proteolytic activity. Instead, they control access to the proteolytic core chamber via a gate-opening/closing mechanism. The 20 S proteasome exists primarily as a closed-gate (inactive) conformation in its latent form (Groll and Potts (2011) *Curr. Top. Med. Chem.* 11: 2850-2878). Conformational change leading to gate opening can be induced by docking an activator protein onto the α-ring, by inserting the "anchors" of 19 S Rpt subunits (regulatory particle ATPases) into α-ring pockets and by allosteric signaling from the active centers (Finley et al. (2016) *Trends Biochem. Sci.* 41: 77-93; Stadtmueller et al. (2010) *J. Biol. Chem.* 285: 13-17; Bar-Nun and Glickman (2012) *Biochimica et biophysica acta* 1823: 67-82; Osmulski et al. (2009) *Structure* 17: 1137-1147).

Nearly all proteasome inhibitors are competitive inhibitors that covalently bind in the catalytic subunits in the β-ring of the proteasome (Groll et al. (2006) *J. Am. Chem. Soc.* 128: 5136-5141). In contrast to the typical competitive inhibitors, rapamycin was found to allosterically modulate proteolytic activity by putatively binding to the α-face (the outer surface of α rings) of the 20 S proteasome (Osmulski and Gaczynska (2013)*Molecular pharmacology* 84: 104-113). Allosteric modulation relies on coupling conformational changes between distant sites.

Despite the relative toxicity and inevitable resistant observed with the competitive proteasome inhibitors currently used in the clinic, the development of allosteric proteasome inhibitors has remained elusive. Thus, there remains a need for small molecules capable of allosteric proteasome modulation. These needs and others are met by the following disclosure.

SUMMARY

In accordance with the purpose(s) of the invention, as embodied and broadly described herein, the invention, in one aspect, relates to compounds and compositions for use in the treatment of disorders of uncontrolled cellular proliferation such as, for example, a cancer.

Disclosed are compounds having a structure represented by a formula selected from:

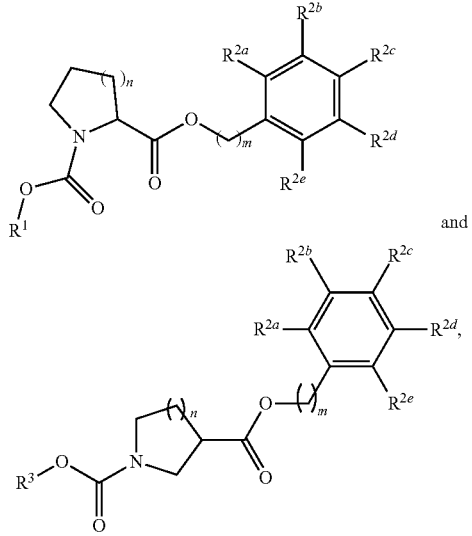

and wherein n is 1 or 2; wherein m is 1, 2, or 3; wherein $R^1$ is selected from $(CH_2)_qCy^1$, $Cy^1$, and C1-C8 acyclic alkyl substituted with 0, 1, 2, or 3 groups independently selected from halogen, —CN, —$NH_2$, —$NO_2$, —OH, —C(O)$NR^{20a}R^{20b}$, —$CO_2H$, and —$CO_2$(C1-C4 alkyl); wherein q, when present, is 1, 2, or 3; wherein each of $R^{20a}$ and $R^{20b}$, when present, is independently selected from hydrogen and C1-C4 alkyl; wherein $Cy^1$ is selected from cyclohexyl and 6-membered monocyclic aryl, and is substituted with 0, 1, 2, or 3 groups independently selected from halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein each of $R^{2a}$, $R^{2b}$, $R^{2c}$, $R^{2d}$, and $R^{2e}$ is independently selected from hydrogen, halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein $R^3$, when present, is selected from C1-C8 alkyl, $(CH_2)_qCy^1$, and $Cy^1$, provided at least one of $R^{2a}$, $R^{2b}$, $R^{2c}$, $R^{2d}$, and $R^{2e}$ is —OH, C1-C4 alkoxy, or C1-C4 haloalkoxy, and provided when at least one of $R^{2a}$, $R^{2b}$, $R^{2c}$, $R^{2d}$, and $R^{2e}$ is C1-C4 alkoxy and $R^1$ is C1-C8 acyclic alkyl, then $R^1$ is substituted with 1, 2, or 3 groups independently selected from halogen, —CN, —$NH_2$, —$NO_2$, —OH, —C(O)$NR^{20a}R^{20b}$, —$CO_2H$, and —$CO_2$(C1-C4 alkyl), or a pharmaceutically acceptable salt thereof.

Also disclosed are compounds having a structure selected from:

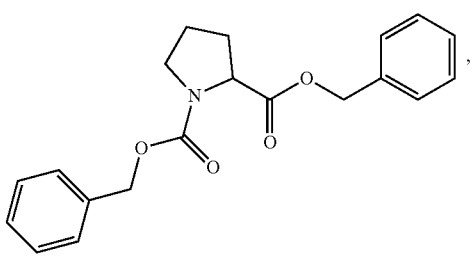

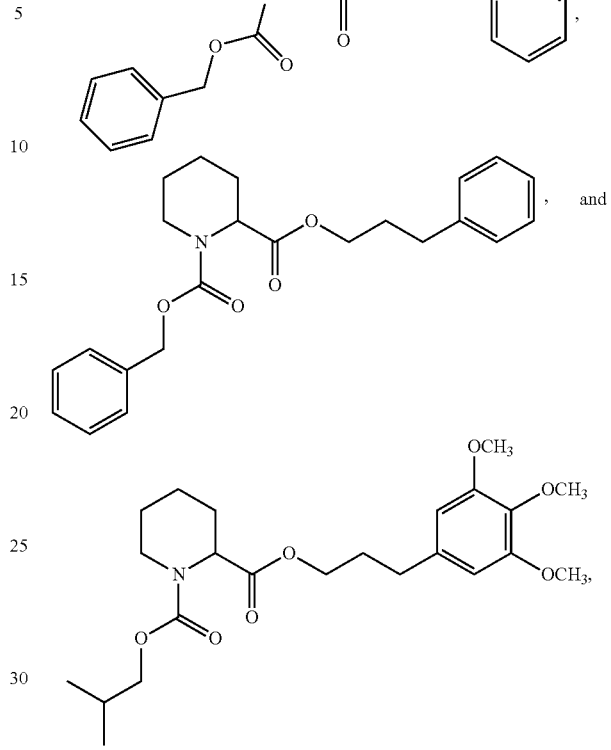

or a pharmaceutically acceptable salt thereof.

Also disclosed are methods of making a disclosed compound.

Also disclosed are pharmaceutical compositions comprising at least one disclosed compound.

Also disclosed are methods for the treatment of a disorder of uncontrolled cellular proliferation in a subject, the method comprising the step of administering to the subject an effective amount of at least one disclosed compound or composition.

Also disclosed are methods for modifying a proteasome in a subject, the method comprising the step of administering to the subject an effective amount of a disclosed compound or composition.

Also disclosed are methods for modifying a proteasome in at least one cell, the method comprising the step of contacting at least one cell with an effective amount of a disclosed compound or composition.

Also disclosed are methods of effecting immunosuppression in a subject, the method comprising the step of administering to the subject an effective amount of a disclosed compound or composition.

Also disclosed are kits comprising at least one disclosed compound or composition, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
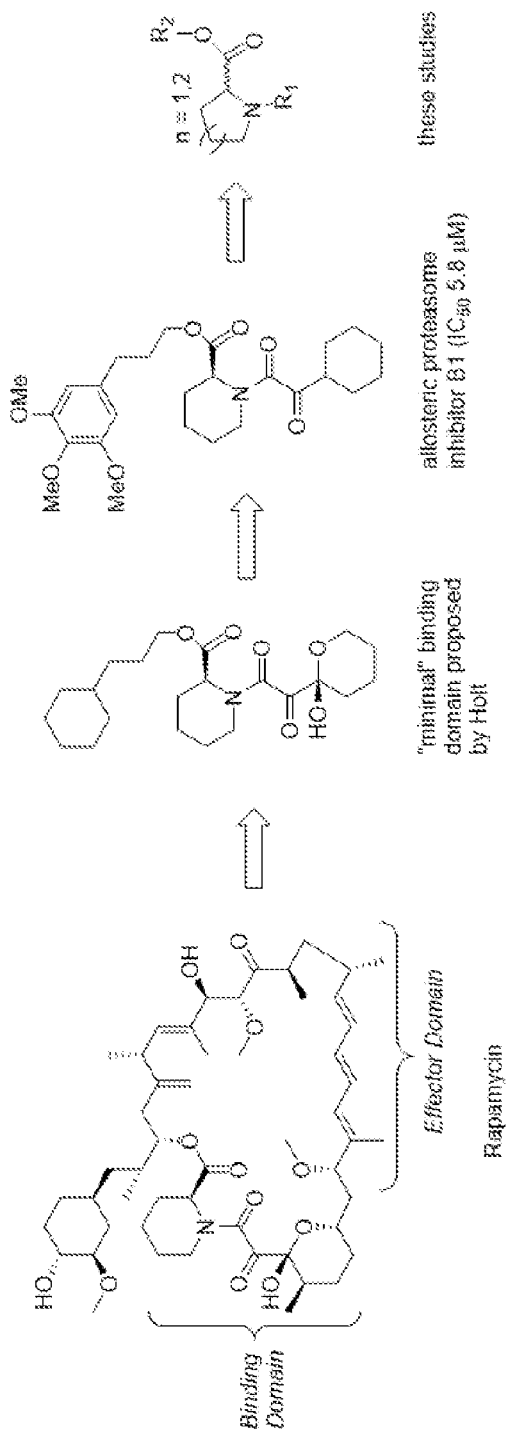
FIG. 1 shows a representative design of a proteasome-targeting pharmacophore of rapamycin.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated 10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrhythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. For example, the cycloalkyl group and heterocycloalkyl group can be substituted with 0, 1, 2, 3, or 4 groups independently selected from C1-C4 alkyl, C3-C7 cycloalkyl, C1-C4 alkoxy, —NH$_2$, (C1-C4) alkylamino, (C1-C4)(C1-C4) dialkylamino, ether, halogen, —OH, C1-C4 hydroxyalkyl, —NO$_2$, silyl, sulfo-oxo, —SH, and C1-C4 thioalkyl, as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbomenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. For example, the cycloalkenyl group and heterocycloalkenyl group can be substituted with 0, 1, 2, 3, or 4 groups independently selected from C1-C4 alkyl, C3-C7 cycloalkyl, C1-C4 alkoxy, C2-C4 alkenyl, C3-C6 cycloalkenyl, C2-C4 alkynyl, aryl, heteroaryl, aldehyde, —NH$_2$, (C1-C4) alkylamino, (C1-C4)(C1-C4) dialkylamino, carboxylic acid, ester, ether, halogen, —OH, C1-C4 hydroxyalkyl, ketone, azide, —NO$_2$, silyl, sulfo-oxo, —SH, and C1-C4 thioalkyl, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptenyl, cyclooctenyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to α ring structure having cyclic clouds of delocalized π electrons above and below the plane of the molecule, where the 1 clouds contain (4n+2)π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" or "CO" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo [c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxy" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN or —C≡N.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R°$; $—(CH_2)_{0-4}OR°$; $—O(CH_2)_{0-4}R°$, $—O—(CH_2)_{0-4}C(O)OR°$; $—(CH_2)_{0-4}CH(OR°)_2$; $—(CH_2)_{0-4}SR°$; $—(CH_2)_{0-4}Ph$, which may be substituted with R°; $—(CH_2)_{0-4}O(CH_2)_{0-1}Ph$ which may be substituted with R°; —CH=CHPh, which may be substituted with R°; $—(CH_2)_{0-4}O(CH_2)_{0-1}$-pyridyl which may be substituted with R°; $—NO_2$; —CN; $—N_3$; $—(CH_2)_{0-4}N(R°)_2$; $—(CH_2)_{0-4}N(R°)C(O)R°$; $—N(R°)C(S)R°$; $—(CH_2)_{0-4}N(R°)C(O)NR°_2$; $—N(R°)C(S)NR°_2$; $—(CH_2)_{0-4}N(R°)C(O)OR°$; $—N(R°)N(R°)C(O)R°$; $—N(R°)N(R°)C(O)NR°_2$; $—N(R°)N(R°)C(O)OR°$; $—(CH_2)_{0-4}C(O)R°$; $—C(S)R°$; $—(CH_2)_{0-4}C(O)OR°$; $—(CH_2)_{0-4}C(O)SR°$; $—(CH_2)_{0-4}C(O)OSiR°_3$; $—(CH_2)_{0-4}OC(O)R°$; $—OC(O)(CH_2)_{0-4}SR—$, $SC(S)SR°$; $—(CH_2)_{0-4}SC(O)R°$; $—(CH_2)_{0-4}C(O)NR°_2$; $—C(S)NR°_2$; $—C(S)SR°$; $—(CH_2)_{0-4}OC(O)NR°_2$; $—C(O)N(OR°)R°$; $—C(O)C(O)R°$; $—C(O)CH_2C(O)R°$; $—C(NOR°)R°$; $—(CH_2)_{0-4}SSR°$; $—(CH_2)_{0-4}S(O)_2R°$; $—(CH_2)_{0-4}S(O)_2OR°$; $—(CH_2)_{0-4}OS(O)_2R°$; $—S(O)_2NR°_2$; $—(CH_2)_{0-4}S(O)R°$; $—N(R°)S(O)_2NR°_2$; $—N(R°)S(O)_2R°$; $—N(OR°)R°$; $—C(NH)NR°_2$; $—P(O)_2R°$; $—P(O)R°_2$; $—OP(O)R°_2$; $—OP(O)(OR°)_2$; $SiR°_3$; $—(C_{1-4}$ straight or branched alkylene)O—$N(R°)_2$; or $—(C_{1-4}$ straight or branched alkylene)C(O)O—$N(R°)_2$, wherein each R° may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^●$, -(haloR$^●$), —$(CH_2)_{0-2}$OH, —$(CH_2)_{0-2}OR^●$, —$(CH_2)_{0-2}$CH(OR$^●$)$_2$; —O(haloR$^●$), —CN, —$N_3$, —$(CH_2)_{0-2}$C(O)R$^●$, —$(CH_2)_{0-2}$C(O)OH, —$(CH_2)_{0-2}$C(O)OR$^●$, —$(CH_2)_{0-2}$SR$^●$, —$(CH_2)_{0-2}$SH, —$(CH_2)_{0-2}NH_2$, —$(CH_2)_{0-2}$NHR$^●$, —$(CH_2)_{0-2}NR^●_2$, —$NO_2$, —SiR$^●_3$, —OSiR$^●_3$, —C(O)SR$^●$, —$(C_{1-4}$ straight or branched alkylene)C(O)OR$^●$, or —SSR$^●$ wherein each R$^●$ is unsubstituted or where preceded by "halo" is substituted only with one or more halogens, and is independently selected from $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$ S—, wherein each independent occurrence of R* is selected from hydrogen, C1-6 aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —$NH_2$, —NHR$^●$, —NR$^●_2$, or —$NO_2$, wherein each R$^●$ is unsubstituted or where preceded by "halo" is substituted only with one or more halogens, and is independently C1-4 aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)$CH_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —$NH_2$, —NHR$^●$, —NR$^●$2, or —$NO_2$, wherein each R$^●$ is unsubstituted or where preceded by "halo" is substituted only with one or more halogens, and is independently $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

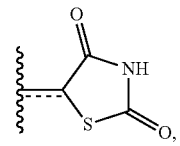

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkylcar-boxamide, alkylsulfonyl, alkylsulfinyl, thioalkyl, thiohaloal-kyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

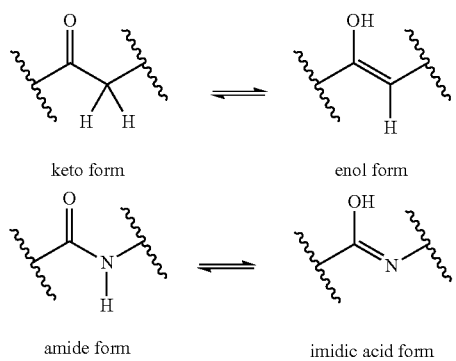

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

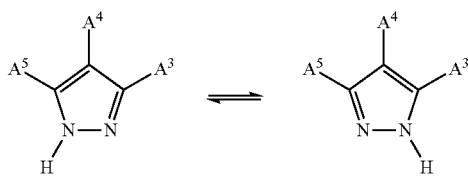

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

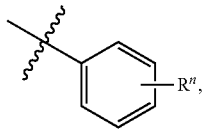

which is understood to be equivalent to a formula:

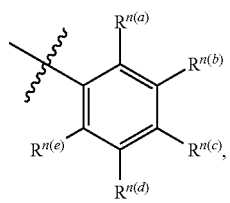

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B—F, C-D, C-E, and C—F are considered disclosed. Likewise, any subset or combination of these is also disclosed. Thus, for example, the sub-group of A-E, B—F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, disclosed are compounds useful in treating or preventing a disorder of uncontrolled cellular proliferation such as, for example, a cancer. Examples of cancers include, but are not limited to, a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

In one aspect, the compounds of the invention are useful in the treatment or prevention of disorders associated with the proteasome, as further described herein. In a further aspect, the disclosed compounds exhibit modulation of the proteasome. In a still further aspect, the disclosed compounds exhibit inhibition of proteasome activity.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula selected from:

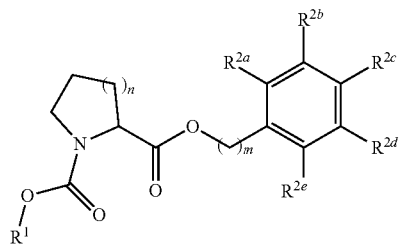

and

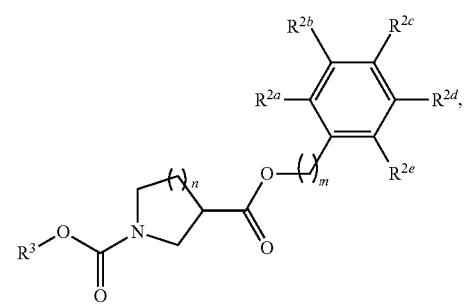

wherein n is 1 or 2; wherein m is 1, 2, or 3; wherein $R^1$ is selected from $(CH_2)_qCy^1$, $Cy^1$, and C1-C8 acyclic alkyl substituted with 0, 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl); wherein q, when present, is 1, 2, or 3; wherein each of $R^{20a}$ and $R^{20b}$, when present, is independently selected from hydrogen and C1-C4 alkyl; wherein $Cy^1$ is selected from cyclohexyl and 6-membered monocyclic aryl, and is substituted with 0, 1, 2, or 3 groups independently selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein each of $R^{2a}$, $R^{2b}$, $R^{2c}$, $R^{2d}$, and $R^{2e}$ is independently selected from hydrogen, halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein $R^3$, when present, is selected from C1-C8 alkyl, $(CH_2)_qCy^1$, and $Cy^1$, provided at least one of $R^{2a}$, $R^{2b}$, $R^{2c}$, $R^{2d}$, and $R^{2e}$ is —OH, C1-C4 alkoxy, or C1-C4 haloalkoxy, and provided when at least one of $R^{2a}$, $R^{2b}$, $R^{2c}$, $R^{2d}$, and $R^{2e}$ is C1-C4 alkoxy and $R^1$ is C1-C8 acyclic alkyl, then $R^1$ is substituted with 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl), or a pharmaceutically acceptable salt thereof.

In one aspect, disclosed are compounds having a structure selected from:

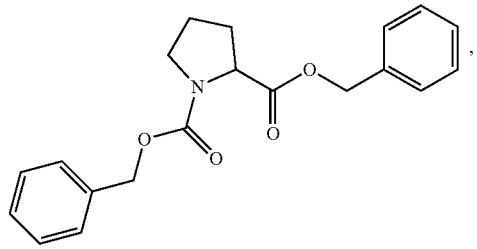,

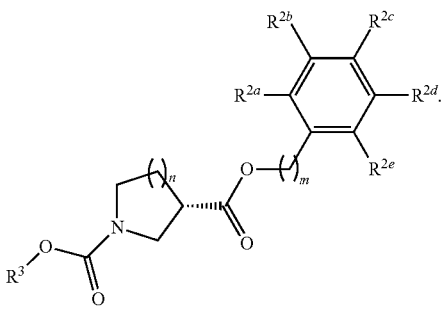,

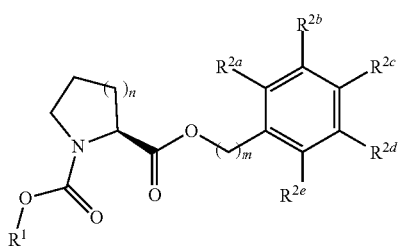, and

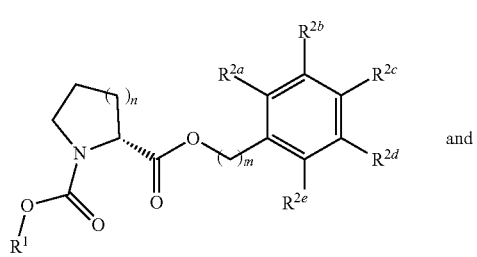

or a pharmaceutically acceptable salt thereof.

In a further aspect, the compound has a structure represented by a formula selected from:

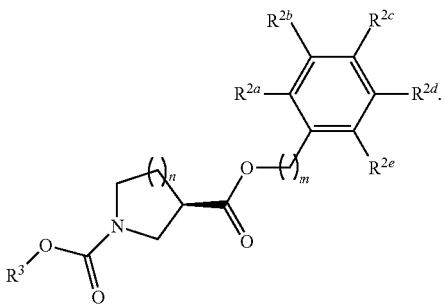 and

In a further aspect, the compound has a structure represented by a formula selected from:

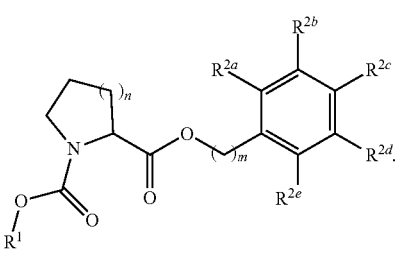

In a further aspect, the compound has a structure represented by a formula:

In a further aspect, the compound has a structure represented by a formula:

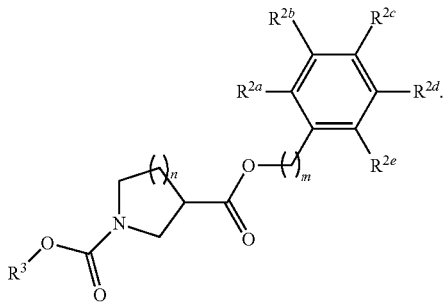

In a further aspect, the compound has a structure represented by a formula selected from:

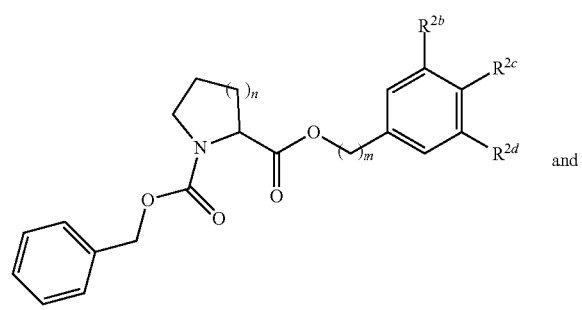

and

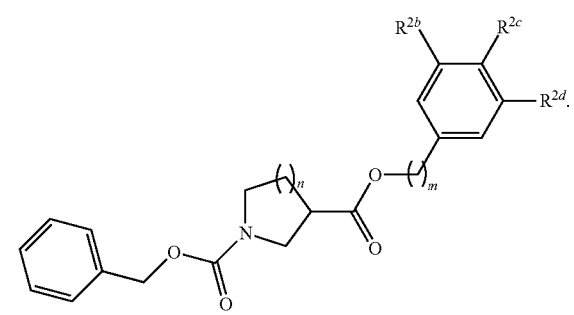

In a further aspect, the compound has a structure represented by a formula selected from:

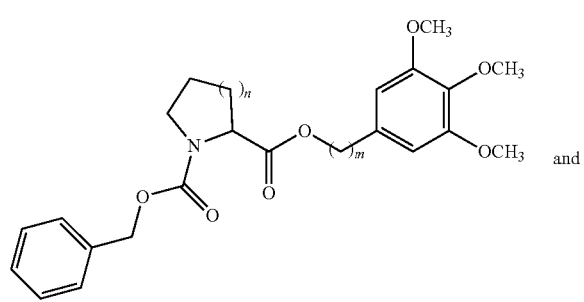

and

-continued

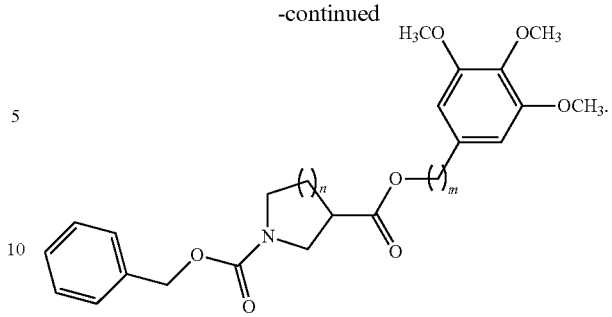

In one aspect, n is 1 or 2. In a further aspect, n is 1. In a still further aspect, n is 2.

In one aspect, m is 1, 2, or 3. In a further aspect, m is 1 or 2. In a still further aspect, m is 2 or 3. In yet a further aspect, m is 1 or 3. In an even further aspect, m is 1. In a still further aspect, m is 2. In yet a further aspect, m is 3.

In one aspect, q, when present, is 1, 2, or 3. In a further aspect, q, when present, is 1 or 2. In a still further aspect, q, when present, is 2 or 3. In yet a further aspect, q, when present, is 1 or 3. In an even further aspect, q, when present, is 1. In a still further aspect, q, when present, is 2. In yet a further aspect, q, when present, is 3.

a. $R^1$ Groups

In one aspect, $R^1$ is selected from $(CH_2)_q Cy^1$, $Cy^1$, and C1-C8 acyclic alkyl substituted with 0, 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl).

In a further aspect, $R^1$ is C1-C8 acyclic alkyl substituted with 0, 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl). In a still further aspect, $R^1$ is C1-C8 acyclic alkyl substituted with 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl). In yet a further aspect, $R^1$ is C1-C8 acyclic alkyl substituted with 0, 1, or 2 groups independently selected from halogen, —CN, —NH$_2$, —NO$_2$, —OH, —C(O)NR$^{20a}$R$^{20b}$, —C$_2$H, and —C$_2$(C1-C4 alkyl). In an even further aspect, $R^1$ is C1-C8 acyclic alkyl substituted with 0 or 1 group selected from halogen, —CN, —NH$_2$, —NO$_2$, —OH, —C(O)NR$^{20a}$R$^{20b}$, —C$_2$H, and —C$_2$(C1-C4 alkyl). In a still further aspect, $R^1$ is C1-C8 acyclic alkyl monosubstituted with a group selected from halogen, —CN, —NH$_2$, —NO$_2$, —OH, —C(O)NR$^{20a}$R$^{20b}$, —C$_2$H, and —C$_2$(C1-C4 alkyl). In yet a further aspect, $R^1$ is unsubstituted C1-C8 acyclic alkyl.

In a further aspect, $R^1$ is C1-C8 acyclic alkyl substituted with 1, 2, or 3 groups independently selected from halogen, —CN, —NH$_2$, —NO$_2$, —OH, —C(O)NR$^{2a}$R$^{20b}$, —CO$_2$H, and —CO$_2$(C1-C4 alkyl). In a still further aspect, $R^1$ is C1-C8 acyclic alkyl substituted with 1 or 2 groups independently selected from halogen, —CN, —NH$_2$, —NO$_2$, —OH, —C(O)NR$^{20a}$R$^{20b}$, —CO$_2$H, and —CO$_2$(C1-C4 alkyl). In yet a further aspect, $R^1$ is C1-C8 acyclic alkyl substituted with 2 or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl). In an even further aspect, $R^1$ is C1-C8 acyclic alkyl substituted with 1 or 3 groups independently selected from halogen, —CN, —NH$_2$, —NO$_2$, —OH, —C(O)NR$^{20a}$R$^{20b}$, —C$_2$H, and —CO$_2$(C1-C4 alkyl). In a still further aspect, $R^1$ is C1-C8 acyclic alkyl substituted with 2 groups independently selected from halogen, —CN, —NH$_2$, —NO$_2$, —OH, —C(O)NR$^{20a}$R$^{20b}$, —C$_2$H, and —CO$_2$(C1-C4 alkyl). In yet a further aspect, $R^1$ is C1-C8 acyclic alkyl substituted with 3 groups independently selected from halogen, —CN, —NH$_2$, —NO$_2$, —OH, —C(O)NR$^{20a}$R$^{20b}$, —CO$_2$H, and —CO$_2$(C1-C4 alkyl).

In a further aspect, $R^1$ is selected from (CH$_2$)$_q$Cy$^1$ and Cy$^1$. In a still further aspect, $R^1$ is (CH$_2$)$_q$Cy$^1$. In yet a further aspect, $R^1$ is Cy$^1$.

In a further aspect, $R^1$ is selected from CH$_2$Cy$^1$ and Cy$^1$. In a still further aspect, $R^1$ is CH$_2$Cy$^1$.

In a further aspect, $R^1$ is C1-C8 acyclic alkyl. In a still further aspect, $R^1$ is C1-C4 acyclic alkyl. In yet a further aspect, $R^1$ is selected from methyl, ethyl, n-propyl, and i-propyl. In an even further aspect, $R^1$ is selected from methyl and ethyl. In a still further aspect, $R^1$ is selected from n-propyl, and i-propyl. In yet a further aspect, $R^1$ is ethyl. In an even further aspect, $R^1$ is methyl.

b. $R^{2a}$, $R^{2b}$, $R^{2c}$, $R^{2d}$, and $R^{2e}$ Groups

In one aspect, each of $R^{2a}$, $R^{2b}$, $R^{2c}$, $R^{2d}$, and $R^{2e}$ is independently selected from hydrogen, halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In a further aspect, each of $R^{2a}$, $R^{2b}$, $R^{2c}$, $R^{2d}$, and $R^{2e}$ is hydrogen.

In a further aspect, each of $R^{2a}$, $R^{2b}$, $R^{2c}$, $R^{2d}$, and $R^{2e}$ is independently selected from hydrogen, —F, —Cl, —CN, —NH$_2$, —NO$_2$, —OH, methyl, ethyl, n-propyl, i-propyl, n-butyl, t-butyl, s-butyl, i-butyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$C, —CH(CH$_3$)CH$_2$C, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH$_2$CH$_2$CH$_3$, and —N(CH$_3$)CH(CH$_3$)$_2$. In a still further aspect, each of $R^{2a}$, $R^{2b}$, $R^{2c}$, $R^{2d}$, and $R^{2e}$ is independently selected from hydrogen, —F, —Cl, —CN, —NH$_2$, —NO$_2$, —OH, methyl, ethyl, n-propyl, i-propyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH$_2$CH$_2$CH$_3$, and —N(CH$_3$)CH(CH$_3$)$_2$. In yet a further aspect, each of $R^{2a}$, $R^{2b}$, $R^{2c}$, $R^{2d}$, and $R^{2e}$ is independently selected from hydrogen, —F, —Cl, —CN, —NH$_2$, —NO$_2$, —OH, methyl, ethyl, —CH$_2$F, —CH$_2$CH$_2$F, —CH$_2$C, —CH$_2$CH$_2$Cl, —CH$_2$OH, —CH$_2$CH$_2$OH, —OCH$_3$, —OCH$_2$CH$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In an even further aspect, each of $R^{2a}$, $R^{2b}$, $R^{2c}$, $R^{2d}$, and $R^{2e}$ is independently selected from hydrogen, —F, —Cl, —CN, —NH$_2$, —NO$_2$, —OH, methyl, —CH$_2$F, —CH$_2$Cl, —CH$_2$OH, —OCH$_3$, —NHCH$_3$, and —N(CH$_3$)$_2$.

In a further aspect, each of $R^{2a}$, $R^{2b}$, $R^{2c}$, $R^{2d}$, and $R^{2e}$ is independently selected from hydrogen, —F, —Cl, —CN, —NH$_2$, —NO$_2$, —OH, —C$_2$H, —CH$_2$OH, —CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH$_2$CH$_2$CH$_3$, and —N(CH$_3$)CH(CH$_3$)$_2$. In yet a further aspect, each of $R^{2a}$, $R^{2b}$, $R^{2c}$, $R^{2d}$, and $R^{2e}$ is independently selected from hydrogen, —F, —Cl, —CN, —NH$_2$, —NO$_2$, —OH, —CH$_2$OH, —CH$_2$CH$_2$OH, —OCH$_3$, —OCH$_2$CH$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In an even further aspect, each of $R^{2a}$, $R^{2b}$, $R^{2c}$, $R^{2d}$, and $R^{2e}$ is independently selected from hydrogen, —F, —Cl, —CN, —NH$_2$, —NO$_2$, —OH, —CH$_2$OH, —OCH$_3$, —NHCH$_3$, and —N(CH$_3$)$_2$.

In a further aspect, each of $R^{2a}$, $R^{2b}$, $R^{2c}$, $R^{2d}$, and $R^{2e}$ is independently selected from hydrogen, —F, —Cl, methyl, ethyl, n-propyl, i-propyl, n-butyl, t-butyl, s-butyl, i-butyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH$_2$CH$_2$CH$_3$, and —N(CH$_3$)CH(CH$_3$)$_2$. In a still further aspect, each of $R^{2a}$, $R^{2b}$, $R^{2c}$, $R^{2d}$, and $R^{2e}$ is independently selected from hydrogen, —F, —Cl, methyl, ethyl, n-propyl, i-propyl, —CH$_2$F, —CH$_2$CH$_2$F, —CH$_2$CH$_2$CH$_2$F, —CH(CH$_3$)CH$_2$F, —CH$_2$Cl, —CH$_2$CH$_2$Cl, —CH$_2$CH$_2$CH$_2$Cl, —CH(CH$_3$)CH$_2$Cl, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH$_2$CH$_2$CH$_3$, and —N(CH$_3$)CH(CH$_3$)$_2$. In yet a further aspect, each of $R^{2a}$, $R^{2b}$, $R^{2c}$, $R^{2d}$, and $R^{2e}$ is independently selected from hydrogen, —F, —Cl, methyl, ethyl, —CH$_2$F, —CH$_2$CH$_2$F, —CH$_2$Cl, —CH$_2$CH$_2$Cl, —CH$_2$OH, —CH$_2$CH$_2$OH, —OCH$_3$, —OCH$_2$CH$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In an even further aspect, each of $R^{2a}$, $R^{2b}$, $R^{2c}$, $R^{2d}$, and $R^{2e}$ is independently selected from hydrogen, —F, —Cl, methyl, —CH$_2$F, —CH$_2$Cl, —CH$_2$OH, —OCH$_3$, —NHCH$_3$, and —N(CH$_3$)$_2$.

In a further aspect, each of $R^{2a}$, $R^{2b}$, $R^{2c}$, $R^{2d}$, and $R^{2e}$ is independently selected from hydrogen and halogen. In a still further aspect, each of $R^{2a}$, $R^{2b}$, $R^{2c}$, $R^{2d}$, and $R^{2e}$ is independently selected from hydrogen, —F, —Cl, and —Br. In yet a further aspect, each of $R^{2a}$, $R^{2b}$, $R^{2c}$, $R^{2d}$, and $R^{2e}$ is independently selected from hydrogen, —F, and —Cl. In an even further aspect, each of $R^{2a}$, $R^{2b}$, $R^{2c}$, $R^{2d}$, and $R^{2e}$ is independently selected from hydrogen and —F. In a still further aspect, each of $R^{2a}$, $R^{2b}$, $R^{2c}$, $R^{2d}$, and $R^{2e}$ is independently selected from hydrogen and —Cl.

In a further aspect, each of $R^{2a}$, $R^{2b}$, $R^{2c}$, $R^{2d}$, and $R^{2e}$ is independently selected from hydrogen and C1-C4 alkyl. In a still further aspect, each of $R^{2a}$, $R^{2b}$, $R^{2c}$, $R^{2d}$, and $R^{2e}$ is independently selected from hydrogen, methyl, ethyl, n-propyl, and i-propyl. In yet a further aspect, each of $R^{2a}$, $R^{2b}$, $R^{2c}$, $R^{2d}$, and $R^{2e}$ is independently selected from hydrogen, methyl, and ethyl. In an even further aspect, each of $R^{2a}$, $R^{2b}$, $R^{2c}$, $R^{2d}$, and Re is independently selected from hydrogen and ethyl. In a still further aspect, each of $R^{2a}$, $R^{2b}$, $R^{2c}$, $R^{2d}$, and $R^{2e}$ is independently selected from hydrogen and methyl.

In a further aspect, each of $R^{2a}$, $R^{2b}$, $R^{2c}$, $R^{2d}$, and $R^{2e}$ is independently selected from hydrogen, —NH$_2$, —OH, —CH$_2$OH, —CH$_2$CH$_2$OH, —CH$_2$CH$_2$CH$_2$OH, —CH (CH$_3$)CH$_2$OH, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH$_2$CH$_2$CH$_3$, and —N(CH$_3$)CH(CH$_3$)$_2$. In yet a further aspect, each of R$^{2a}$, Rb, Re, R$^{2d}$, and R$^{2e}$ is independently selected from hydrogen, —NH$_2$, —OH, —CH$_2$OH, —CH$_2$CH$_2$OH, —OCH$_3$, —OCH$_2$CH$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In an even further aspect, each of R$^{2a}$, R$^{2b}$, R$^{2c}$, R$^{2d}$, and R$^{2e}$ is independently selected from hydrogen, —NH$_2$, —OH, —CH$_2$OH, —OCH$_3$, —NHCH$_3$, and —N(CH$_3$)$_2$.

In a further aspect, each of R$^{2a}$, R$^{2b}$, R$^{2c}$, R$^{2d}$, and R$^{2e}$ is independently selected from hydrogen, —NH$_2$, —OH, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH$_2$CH$_2$CH$_3$, and —N(CH$_3$)CH(CH$_3$)$_2$. In yet a further aspect, each of R$^{2a}$, R$^{2b}$, R$^{2c}$, R$^{2d}$, and R$^{2e}$ is independently selected from hydrogen, —NH$_2$, —OH, —OCH$_3$, —OCH$_2$CH$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In an even further aspect, each of R$^{2a}$, R$^{2b}$, R$^{2c}$, R$^{2d}$, and R$^{2e}$ is independently selected from hydrogen, —NH$_2$, —OH, —OCH$_3$, —NHCH$_3$, and —N(CH$_3$)$_2$.

In a further aspect, each of R$^{2a}$, R$^{2b}$, R$^{2c}$, R$^{2d}$, and R$^{2e}$ is independently selected from hydrogen, —NH$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)$_2$, —N(CH$_3$)CH$_2$CH$_2$CH$_3$, and —N(CH$_3$)CH(CH$_3$)$_2$. In yet a further aspect, each of R$^{2a}$, R$^{2b}$, R$^{2c}$, R$^{2d}$, and R$^{2e}$ is independently selected from hydrogen, —NH$_2$, —NHCH$_3$, —NHCH$_2$CH$_3$, —N(CH$_3$)$_2$, —N(CH$_3$)CH$_2$CH$_3$, and —N(CH$_2$CH$_3$)$_2$. In an even further aspect, each of R$^{2a}$, R$^{2b}$, R$^{2c}$, R$^{2d}$, and R$^{2e}$ is independently selected from hydrogen, —NH$_2$, —NHCH$_3$, and —N(CH$_3$)$_2$.

In a further aspect, each of R$^{2a}$, R$^{2b}$, R$^{2c}$, R$^{2d}$, and R$^{2e}$ is independently selected from hydrogen, —OH, —OCH$_3$, —OCH$_2$CH$_3$, —OCH$_2$CH$_2$CH$_3$, and —OCH(CH$_3$)$_2$. In yet a further aspect, each of R$^{2a}$, R$^{2b}$, R$^{2c}$, R$^{2d}$, and R$^{2e}$ is independently selected from hydrogen, —OH, —OCH$_3$, and —OCH$_2$CH$_3$. In an even further aspect, each of R$^{2a}$, R$^{2b}$, R$^{2c}$, R$^{2d}$, and R$^{2e}$ is independently selected from hydrogen, —OH, and —OCH$_3$.

In a further aspect, at least one of R$^{2a}$, R$^{2b}$, R$^{2c}$, R$^{2d}$, and R$^{2e}$ is C1-C4 alkoxy or C1-C4 haloalkoxy. In a still further aspect, at least two of R$^{2a}$, R$^{2b}$, R$^{2c}$, R$^{2d}$, and R$^{2e}$ are C1-C4 alkoxy or C1-C4 haloalkoxy. In yet a further aspect, at least three of R$^{2a}$, R$^{2b}$, R$^{2c}$, R$^{2d}$, and R$^{2e}$ are C1-C4 alkoxy or C1-C4 haloalkoxy.

In a further aspect, at least one of R$^{2a}$, R$^{2b}$, R$^{2c}$, R$^{2d}$, and R$^{2e}$ is C1-C4 alkoxy. In a still further aspect, at least two of R$^{2a}$, R$^{2b}$, R$^{2c}$, R$^{2d}$, and R$^{2e}$ are C1-C4 alkoxy. In yet a further aspect, at least three of R$^{2a}$, R$^{2b}$, R$^{2c}$, R$^{2d}$, and R$^{2e}$ are C1-C4 alkoxy.

In a further aspect, at least one of R$^{2a}$, R$^{2b}$R$^{2c}$, R$^{2d}$, and R$^{2e}$ is methoxy. In a still further aspect, at least two of R$^{2a}$, R$^{2b}$, R$^{2c}$, R$^{2d}$, and R$^{2e}$ are methoxy. In yet a further aspect, at least three of R$^{2a}$, R$^{2b}$, R$^{2c}$, R$^{2d}$, and R$^{2e}$ are methoxy.

In a further aspect, each of R$^{2b}$, R$^{2c}$, and R$^{2d}$ is methoxy.

c. R$^3$ Groups

In one aspect, R$^3$, when present, is selected from C1-C8 alkyl, (CH$_2$)$_q$Cy$^1$, and Cy$^1$. In a further aspect, R$^3$, when present, is selected from C1-C4 alkyl, (CH$_2$)$_q$Cy$^1$, and Cy$^1$.

In a still further aspect, R$^3$, when present, is selected from methyl, ethyl, n-propyl, i-propyl, (CH$_2$)$_q$Cy$^1$, and Cy$^1$.

In a further aspect, R$^3$, when present, is selected from (CH$_2$)$_q$Cy$^1$ and Cy$^1$. In a still further aspect, R$^3$, when present, (CH$_2$)$_q$Cy$^1$. In yet a further aspect, R$^3$, when present, Cy$^1$.

In a further aspect, R$^3$, when present, is selected from CH$_2$Cy$^1$ and Cy$^1$. In a still further aspect, R$^3$, when present, is CH$_2$Cy$^1$.

In a further aspect, R$^3$, when present, is C1-C8 alkyl. In a still further aspect, R$^3$, when present, is C1-C4 alkyl. In yet a further aspect, R$^3$, when present, is selected from methyl, ethyl, n-propyl, and i-propyl. In an even further aspect, R$^3$, when present, is selected from methyl and ethyl. In a still further aspect, R$^3$, when present, is selected from n-propyl, and i-propyl. In yet a further aspect, R$^3$, when present, is ethyl. In an even further aspect, R$^3$, when present, is methyl.

d. R$^{20A}$ and R$^{20B}$ Groups

In one aspect, each of R$^{20a}$ and R$^{20b}$, when present, is independently selected from hydrogen and C1-C4 alkyl. In a further aspect, each of R$^{20a}$ and R$^{20b}$, when present, is independently selected from hydrogen, methyl, ethyl, n-propyl, and i-propyl. In a still further aspect, each of R$^{20a}$ and R$^{20b}$, when present, is independently selected from hydrogen, methyl, and ethyl. In yet a further aspect, each of R$^{20a}$ and R$^{20b}$, when present, is independently selected from hydrogen and ethyl. In an even further aspect, each of R$^{20a}$ and R$^{20b}$, when present, is independently selected from hydrogen and methyl. In a still further aspect, each of R$^{20a}$ and R$^{20b}$, when present, is hydrogen.

In a further aspect, each of R$^{20a}$ and R$^{20b}$, when present, is independently C1-C4 alkyl. In a still further aspect, each of R$^{20a}$ and R$^{20b}$, when present, is independently selected from methyl, ethyl, n-propyl, and i-propyl. In yet a further aspect, each of R$^{20a}$ and R$^{20b}$, when present, is independently selected from methyl and ethyl. In an even further aspect, each of R$^{20a}$ and R$^{20b}$, when present, is ethyl. In a still further aspect, each of R$^{20a}$ and R$^{20b}$, when present, is methyl.

In a further aspect, R$^{20a}$, when present, is hydrogen and R$^{20b}$, when present, is selected from hydrogen and C1-C4 alkyl. In a still further aspect, R$^{20a}$, when present, is hydrogen and R$^{20b}$, when present, is selected from hydrogen, methyl, ethyl, n-propyl, and i-propyl. In yet a further aspect, R$^{20a}$, when present, is hydrogen and R$^{20b}$, when present, is selected from hydrogen, methyl, and ethyl. In an even further aspect, R$^{20a}$, when present, is hydrogen and R$^{20b}$, when present, is selected from hydrogen and ethyl. In a still further aspect, R$^{20a}$, when present, is hydrogen and R$^{20b}$, when present, is selected from hydrogen and methyl.

In a further aspect, R$^{20b}$, when present, is hydrogen and R$^{20a}$, when present, is selected from hydrogen and C1-C4 alkyl. In a still further aspect, R$^{20b}$, when present, is hydrogen and R$^{20a}$, when present, is selected from hydrogen, methyl, ethyl, n-propyl, and i-propyl. In yet a further aspect, R$^{20b}$, when present, is hydrogen and R$^{20a}$, when present, is selected from hydrogen, methyl, and ethyl. In an even further aspect, R$^{20b}$, when present, is hydrogen and R$^{20a}$, when present, is selected from hydrogen and ethyl. In a still further aspect, R$^{20b}$, when present, is hydrogen and R$^{20a}$, when present, is selected from hydrogen and methyl.

e. Cy$^1$ Groups

In one aspect, Cy$^1$ is selected from cyclohexyl and 6-membered monocyclic aryl, and is substituted with 0, 1, 2, or 3 groups independently selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In a further aspect, Cy$^1$ is selected from cyclohexyl and 6-membered monocyclic aryl, and is substituted with 0, 1, or 2 groups independently selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In a still further aspect, Cy is selected from cyclohexyl and 6-membered monocyclic aryl, and is substituted with 0 or 1 group selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In yet a further aspect, Cy$^1$ is selected from cyclohexyl and 6-membered monocyclic aryl, and is monosubstituted with a group selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In an even further aspect, Cy$^1$ is selected from cyclohexyl and 6-membered monocyclic aryl, and is unsubstituted.

In a further aspect, Cy$^1$ is cyclohexyl substituted with 0, 1, 2, or 3 groups independently selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In a still further aspect, Cy$^1$ is cyclohexyl substituted with 0, 1, or 2 groups independently selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In yet a further aspect, Cy$^1$ is cyclohexyl substituted with 0 or 1 group selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In an even further aspect, Cy$^1$ is cyclohexyl monosubstituted with a group selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino. In a still further aspect, Cy is unsubstituted 6-membered monocyclic aryl.

2. Example Compounds

In one aspect, a compound can be present as one or more of the following structures:

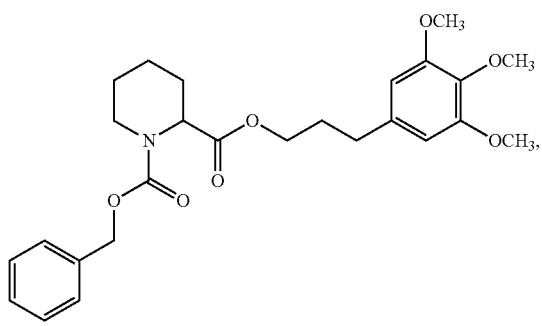

-continued

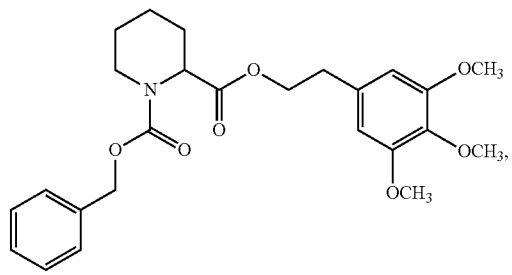

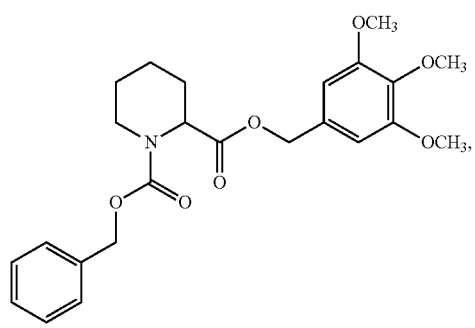

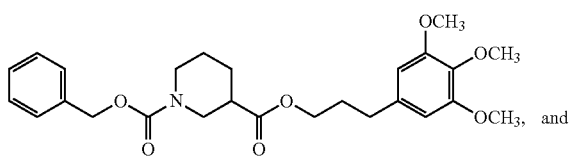

and

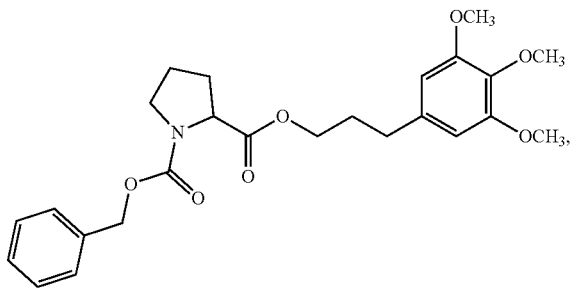

or a pharmaceutically acceptable salt thereof.

In one aspect, a compound can be present as one or more of the following structures:

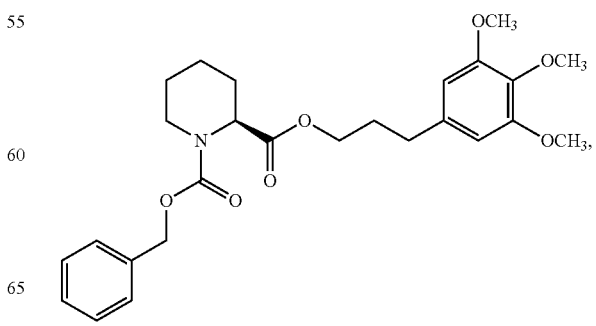

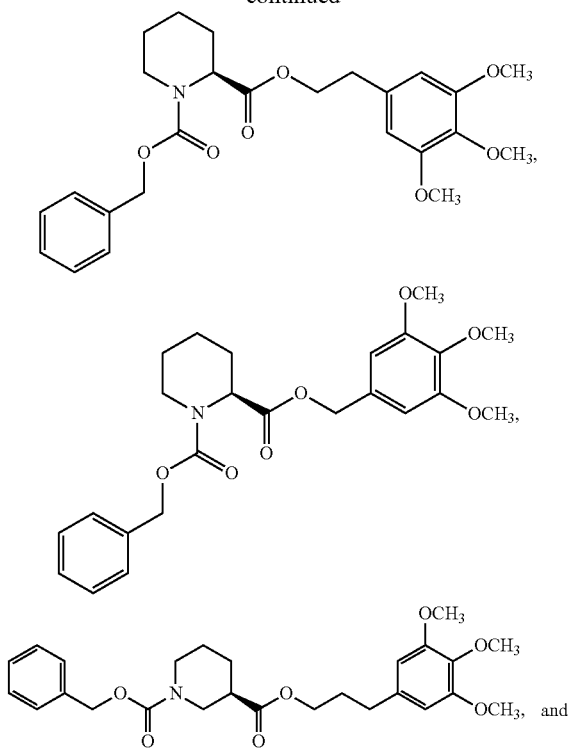
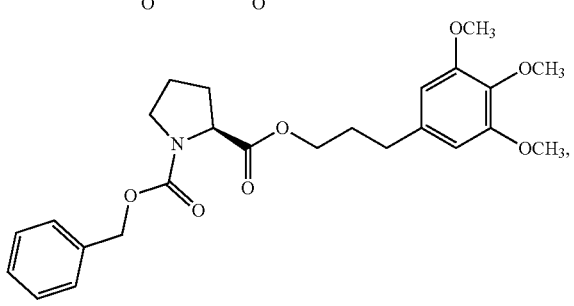
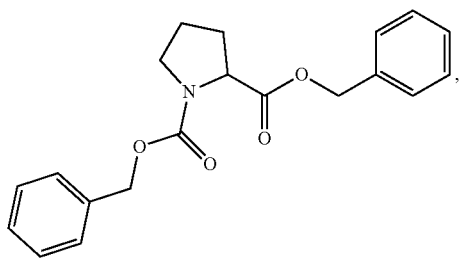
or a pharmaceutically acceptable salt thereof.
In one aspect, a compound can be present as one or more of the following structures:
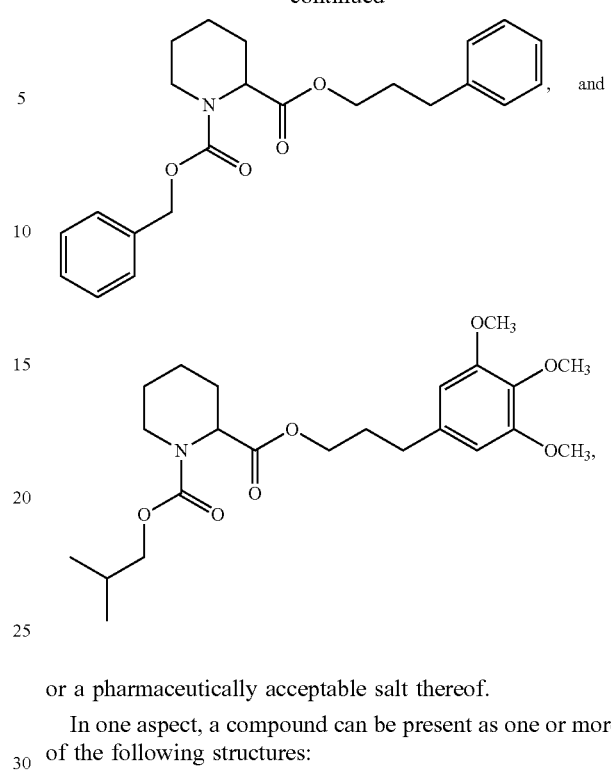
or a pharmaceutically acceptable salt thereof.
In one aspect, a compound can be present as one or more of the following structures:
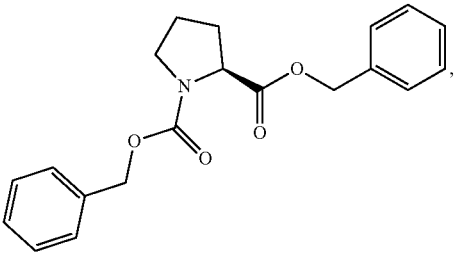
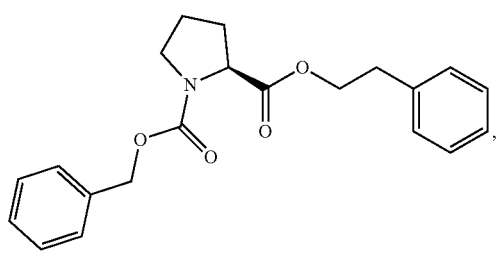
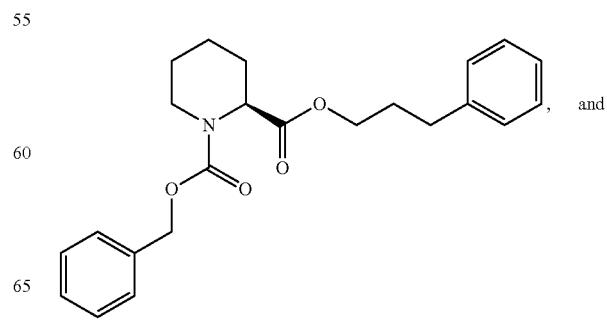

-continued

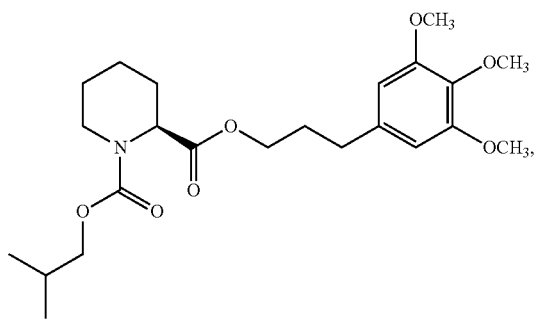

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as proteasome inhibitors, and such activity can be determined using the assay methods described herein.

In one aspect, a compound can be selected from:

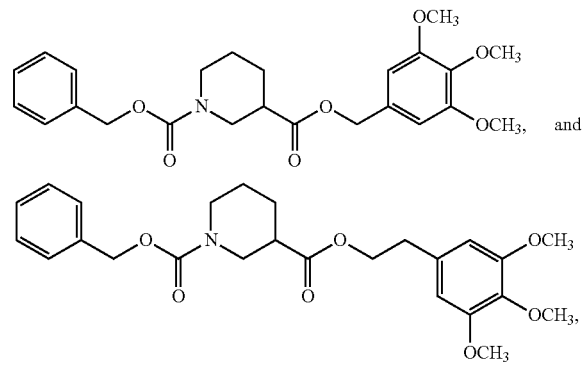

or a pharmaceutically acceptable derivative thereof.

In one aspect, a compound can be selected from:

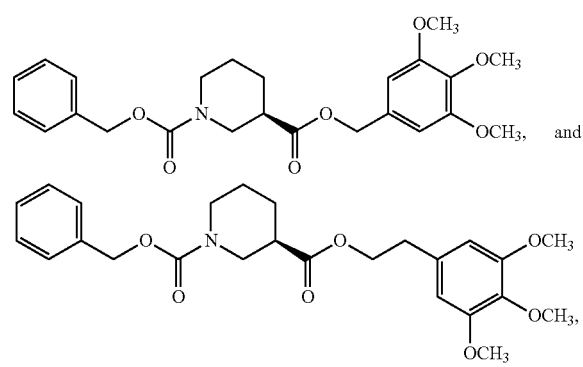

or a pharmaceutically acceptable derivative thereof.

In one aspect, a compound can be selected from:

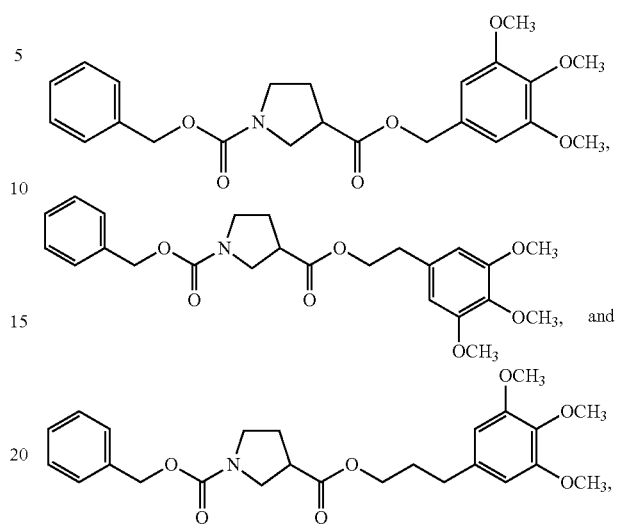

or a pharmaceutically acceptable derivative thereof.

In one aspect, a compound can be selected from:

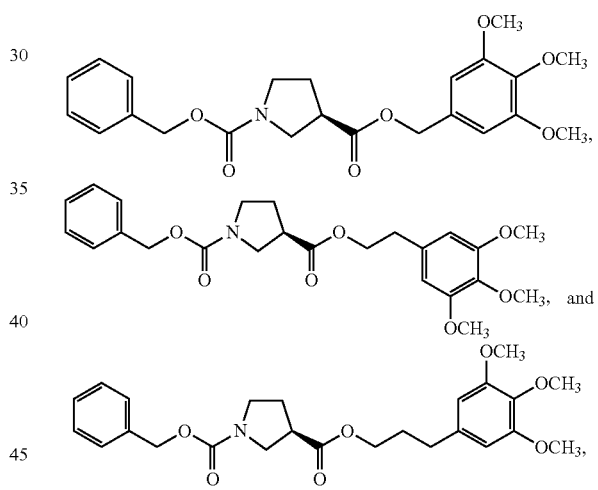

or a pharmaceutically acceptable derivative thereof.

C. Methods of Making a Compound

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-II, as described and exemplified below. The following examples are provided so that the invention might be more fully understood, are illustrative only, and should not be construed as limiting.

1. Route I

In one aspect, substituted pipecolic esters can be prepared as shown below.

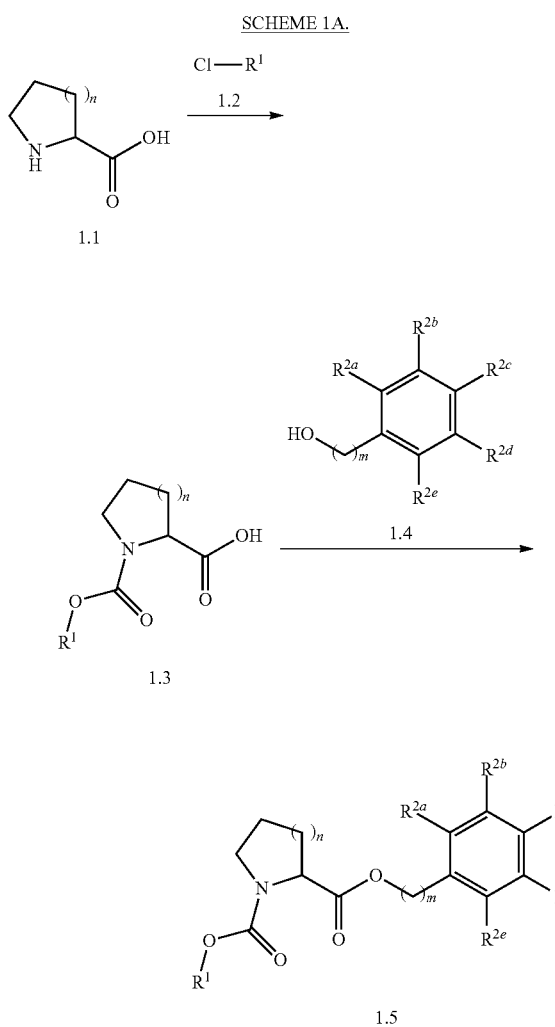

Compounds are represented in generic form, with substituents as noted in compound descriptions elsewhere herein. A more specific example is set forth below.

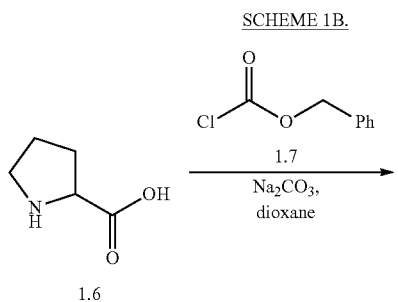

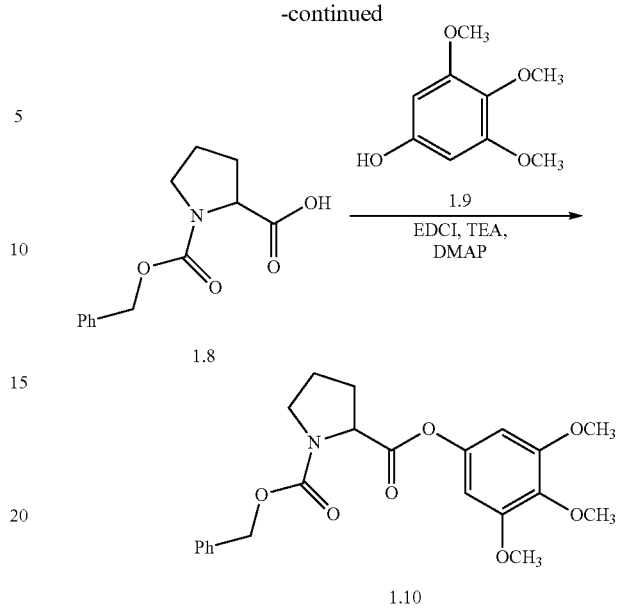

In one aspect, compounds of type 1.10, and similar compounds, can be prepared according to reaction Scheme 1B above. Thus, compounds of type 1.3 can be prepared by an acylation reaction of an appropriate amine, e.g., 1.1 as shown above, and an appropriate acyl halide, e.g., 1.2 as shown above. Appropriate amines and appropriate acyl halides are commercially available or prepared by methods known to one skilled in the art. The acylation reaction is carried out in the presence of an appropriate base, e.g., sodium carbonate, in an appropriate solvent, e.g., dioxane. Compounds of type 1.5 can be prepared by a coupling reaction of an appropriate carboxylic acid, e.g., 1.3 as shown above, and an appropriate alcohol, e.g., 1.4 as shown above. Appropriate alcohols are commercially available or prepared by methods known to one skilled in the art. The coupling reaction is carried out in the presence of an appropriate coupling agent, e.g., 1-ethyl-3-(3-dimethylaminopropyl)carbodiimide (EDCI), an appropriate base, e.g., triethylamine (TEA), and an appropriate catalyst, e.g., 4-dimethylaminopyridine (DMAP). As can be appreciated by one skilled in the art, the above reaction provides an example of a generalized approach wherein compounds similar in structure to the specific reactants above (compounds similar to compounds of type 1.6, 1.7, 1.8, and 1.9), can be substituted in the reaction to provide substituted pipecolic esters similar to Formula 1.10.

2. Route II

In one aspect, substituted pipecolic esters can be prepared as shown below.

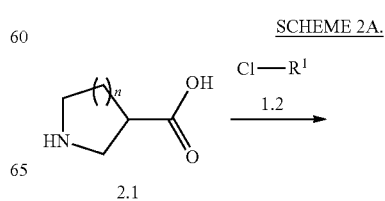

-continued

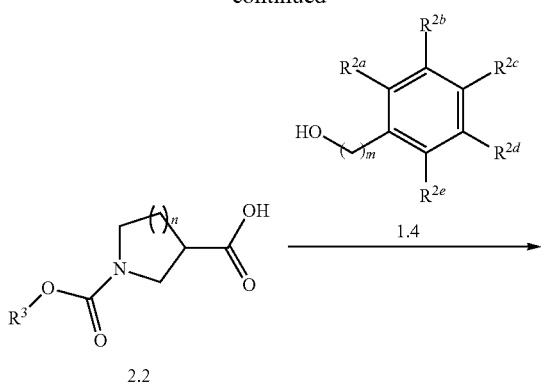

2.2

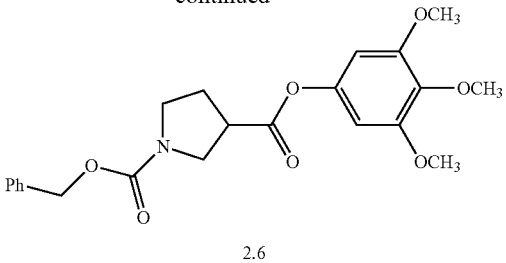

2.6

Compounds are represented in generic form, with substituents as noted in compound descriptions elsewhere herein. A more specific example is set forth below.

SCHEME 2B.

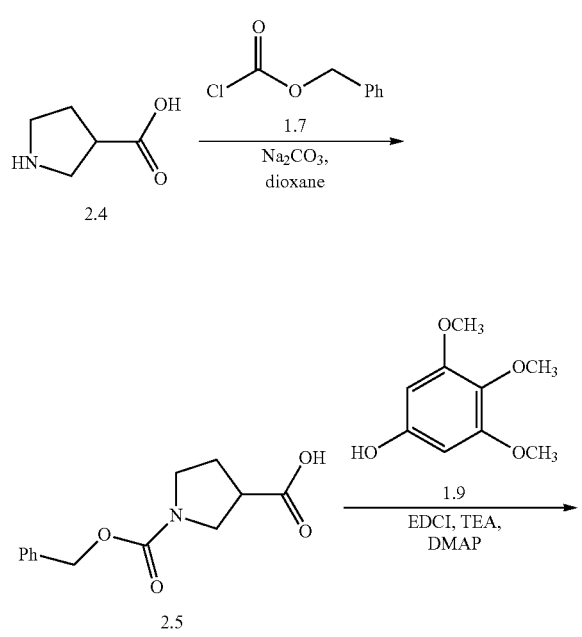

In one aspect, compounds of type 2.6, and similar compounds, can be prepared according to reaction Scheme 2B above. Thus, compounds of type 2.2 can be prepared by an acylation reaction of an appropriate amine, e.g., 2.1 as shown above, and an appropriate acyl halide, e.g., 1.2 as shown above. Appropriate amines and appropriate acyl halides are commercially available or prepared by methods known to one skilled in the art. The acylation reaction is carried out in the presence of an appropriate base, e.g., sodium carbonate, in an appropriate solvent, e.g., dioxane. Compounds of type 2.3 can be prepared by a coupling reaction of an appropriate carboxylic acid, e.g., 2.2 as shown above, and an appropriate alcohol, e.g., 1.4 as shown above. Appropriate alcohols are commercially available or prepared by methods known to one skilled in the art. The coupling reaction is carried out in the presence of an appropriate coupling agent, e.g., 1-ethyl-3-(3-dimethylaminopropyl)carbodiimide (EDCI), an appropriate base, e.g., triethylamine (TEA), and an appropriate catalyst, e.g., 4-dimethylaminopyridine (DMAP). As can be appreciated by one skilled in the art, the above reaction provides an example of a generalized approach wherein compounds similar in structure to the specific reactants above (compounds similar to compounds of type 1.7, 1.9, 2.4, and 2.5), can be substituted in the reaction to provide substituted pipecolic esters similar to Formula 2.6.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

D. Pharmaceutical Compositions

In one aspect, disclosed are pharmaceutical compositions comprising a disclosed compound, or a pharmaceutically acceptable salt thereof and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder of uncontrolled cellular proliferation such as, for example, a cancer.

It is understood that the disclosed compositions can be prepared from the disclosed compounds. It is also understood that the disclosed compositions can be employed in the disclosed methods of using.

E. Methods of Treating a Disorder of Uncontrolled Cellular Proliferation in a Subject In various aspects, the compounds and compositions disclosed herein are useful for treating, preventing, ameliorating, controlling or reducing the risk of a variety of disorders of uncontrolled cellular proliferation, including, for example, cancer. Thus, in one aspect, disclosed are methods of treating a disorder of uncontrolled cellular proliferation in a subject, the method comprising administering to the subject an effective amount of at least one disclosed compound or a pharmaceutically acceptable salt thereof.

In one aspect, disclosed are methods for the treatment of a disorder of uncontrolled cellular proliferation in a subject, the method comprising the step of administering to the subject an effective amount of at least one compound having a structure represented by a formula selected from:

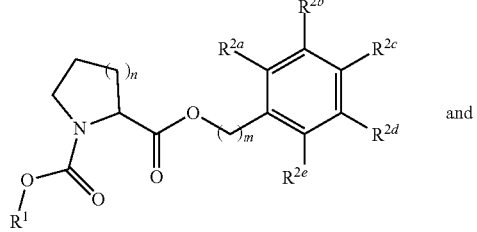

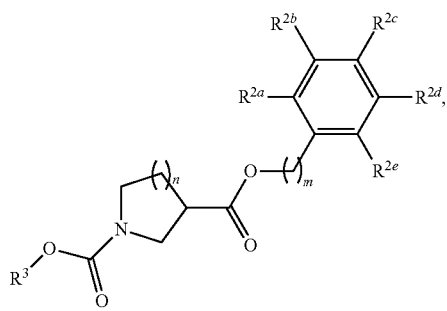

wherein n is 1 or 2; wherein m is 1, 2, or 3; wherein $R^1$ is selected from $(CH_2)_q Cy^1$, $Cy^1$, and C1-C8 acyclic alkyl substituted with 0, 1, 2, or 3 groups independently selected from halogen, —CN, —$NH_2$, —$NO_2$, —OH, —C(O)$NR^{20a}R^{20b}$, —$CO_2H$, and —$CO_2$(C1-C4 alkyl); wherein q, when present, is 1, 2, or 3; wherein each of $R^{20a}$ and $R^{20b}$, when present, is independently selected from hydrogen and C1-C4 alkyl; wherein $Cy^1$ is selected from cyclohexyl and 6-membered monocyclic aryl, and is substituted with 0, 1, 2, or 3 groups independently selected from halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; wherein each of $R^{2a}$, $R^{2b}$, $R^{2c}$, $R^{2d}$, and $R^{2e}$ is independently selected from halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein $R^3$, when present, is selected from C1-C8 alkyl, $(CH_2)_q Cy^1$, and $Cy^1$, provided at least one of $R^{2a}$, $R^{2b}$, $R^{2c}$, $R^{2d}$, and $R^{2e}$ is C1-C4 alkoxy or C1-C4 haloalkoxy, and provided when at least one of $R^{2a}$, $R^{2b}$, $R^{2c}$, $R^{2d}$, and $R^{2e}$ is C1-C4 alkoxy and $R^1$ is C1-C8 acyclic alkyl, then $R^1$ is substituted with 1, 2, or 3 groups independently selected from halogen, —CN, —$NH_2$, —$NO_2$, —OH, —C(O)$NR^{20a}R^{20b}$, —$CO_2H$, and —$CO_2$ (C1-C4 alkyl), or a pharmaceutically acceptable salt thereof.

In one aspect, disclosed are methods for the treatment of a disorder of uncontrolled cellular proliferation in a subject, the method comprising the step of administering to the subject an effective amount of at least one compound having a structure selected from:

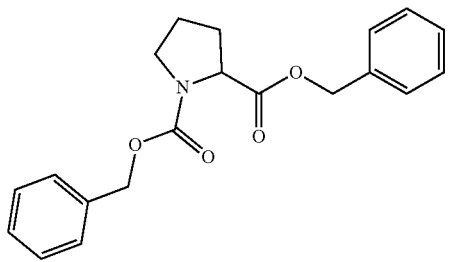

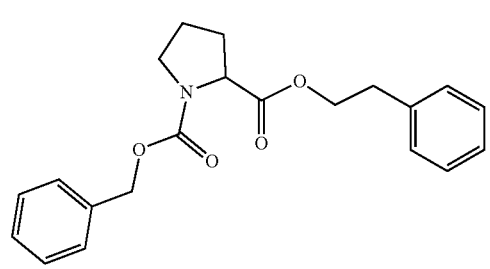

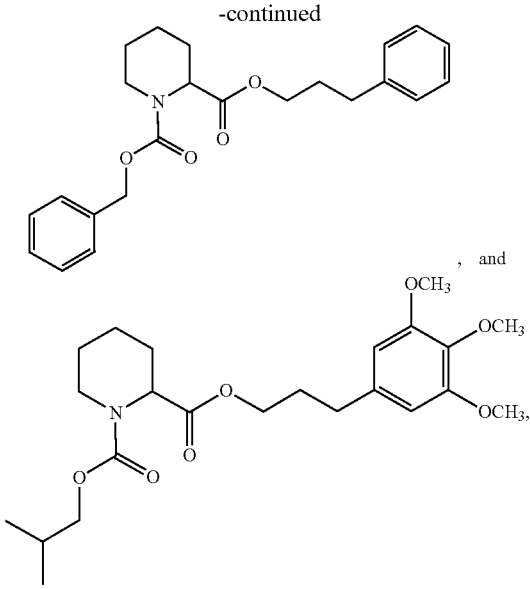

or a pharmaceutically acceptable salt thereof.

In various aspects, the disclosed compounds can be used in combination with one or more other drugs in the treatment, prevention, control, amelioration, or reduction of risk of disorders of uncontrolled cellular proliferation for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In a further aspect, the compound exhibits modulation of a proteasome. In a still further aspect, the compound exhibits inhibition of proteasome activity. In a still further aspect, the compound exhibits a decrease in proteasome activity.

In a further aspect, the compound exhibits inhibition of proteasome activity with an $IC_{50}$ of from about 0.001 µM to about 25 µM. In a still further aspect, the compound exhibits inhibition of proteasome activity with an $IC_{50}$ of from about 0.001 µM to about 15 µM. In yet a further aspect, the compound exhibits inhibition of proteasome activity with an $IC_{50}$ of from about 0.001 µM to about 10 µM. In an even further aspect, the compound exhibits inhibition of proteasome activity with an $IC_{50}$ of from about 0.001 µM to about 5 µM. In a still further aspect, the compound exhibits inhibition of proteasome activity with an $IC_{50}$ of from about 0.001 µM to about 1 µM. In yet a further aspect, the compound exhibits inhibition of proteasome activity with an $IC_{50}$ of from about 0.001 µM to about 0.5 µM. In an even further aspect, the compound exhibits inhibition of protea- some activity with an $IC_{50}$ of from about 0.001 µM to about 0.1 µM. In a still further aspect, the compound exhibits inhibition of proteasome activity with an $IC_{50}$ of from about 0.001 µM to about 0.05 µM. In yet a further aspect, the compound exhibits inhibition of proteasome activity with an $IC_{50}$ of from about 0.001 µM to about 0.01 µM. In an even further aspect, the compound exhibits inhibition of proteasome activity with an $IC_{50}$ of from about 0.001 µM to about 0.005 µM. In a still further aspect, the compound exhibits inhibition of proteasome activity with an $IC_{50}$ of from about 0.005 µM to about 25 µM. In yet a further aspect, the compound exhibits inhibition of proteasome activity with an $IC_{50}$ of from about 0.01 µM to about 25 µM. In an even further aspect, the compound exhibits inhibition of proteasome activity with an $IC_{50}$ of from about 0.05 µM to about 25 µM. In a still further aspect, the compound exhibits inhibition of proteasome activity with an $IC_{50}$ of from about 0.1 µM to about 25 µM. In yet a further aspect, the compound exhibits inhibition of proteasome activity with an $IC_{50}$ of from about 0.5 µM to about 25 µM. In an even further aspect, the compound exhibits inhibition of proteasome activity with an $IC_{50}$ of from about 1 µM to about 25 µM. In a still further aspect, the compound exhibits inhibition of proteasome activity with an $IC_{50}$ of from about 5 µM to about 25 µM. In yet a further aspect, the compound exhibits inhibition of proteasome activity with an $IC_{50}$ of from about 10 µM to about 25 µM. In an even further aspect, the compound exhibits inhibition of proteasome activity with an $IC_{50}$ of from about 15 µM to about 25 µM.

In a further aspect, the subject is a mammal. In a still further aspect, the mammal is human.

In a further aspect, the subject has been diagnosed with a need for treatment of the disorder prior to the administering step. In a still further aspect, the subject is at risk for developing the disorder prior to the administering step.

In a further aspect, the method further comprises identifying a subject at risk for developing the disorder prior to the administering step. In a further aspect, the method further comprises identifying a subject in need of treatment of the disorder prior to the administering step.

In a further aspect, the effective amount is a therapeutically effective amount. In a still further aspect, the effective amount is a prophylactically effective amount.

In a further aspect, the disorder of uncontrolled cellular proliferation is a cancer. In a still further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

F. Methods of Modifying a Proteasome in a Subject

In one aspect, disclosed are methods of modifying a proteasome in a subject, the method comprising the step of administering to the subject an effective amount of at least one disclosed compound, or a pharmaceutically acceptable salt thereof. In a further aspect, modifying is inhibiting.

In one aspect, disclosed are methods for modifying a proteasome in a subject, the method comprising the step of administering to the subject an effective amount of a compound having a structure represented by a formula selected from:

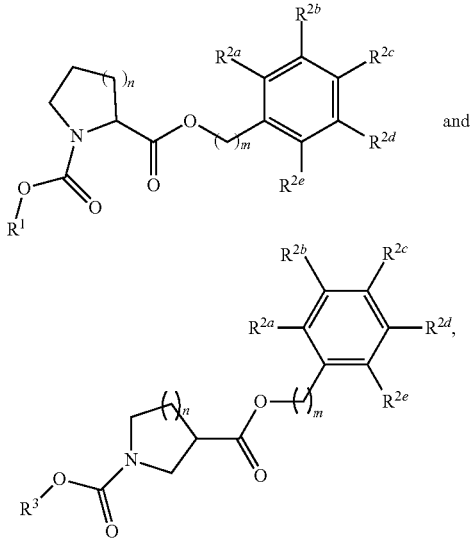

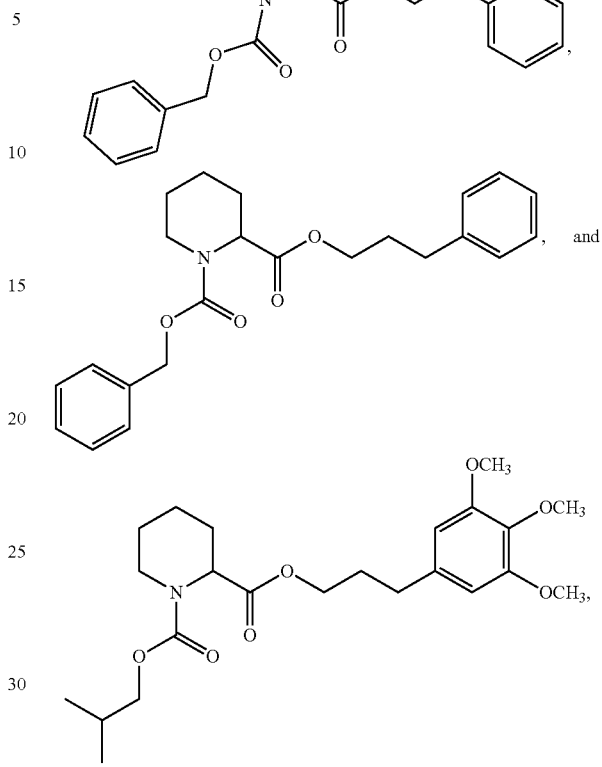

wherein n is 1 or 2; wherein m is 1, 2, or 3; wherein $R^1$ is selected from $(CH_2)_qCy^1$, $Cy^1$, and C1-C8 acyclic alkyl substituted with 0, 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl); wherein q, when present, is 1, 2, or 3; wherein each of $R^{20a}$ and $R^{20b}$, when present, is independently selected from hydrogen and C1-C4 alkyl; wherein $Cy^1$ is selected from cyclohexyl and 6-membered monocyclic aryl, and is substituted with 0, 1, 2, or 3 groups independently selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; wherein each of $R^{2a}$, $R^{2b}$, $R^{2c}$, $R^{2d}$, and $R^{2e}$ is independently selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein $R^3$, when present, is selected from C1-C8 alkyl, $(CH_2)_qCy^1$, and $Cy^1$, provided at least one of $R^{2a}$, $R^{2b}$, $R^{2c}$, $R^{2d}$, and $R^{2e}$ is C1-C4 alkoxy or C1-C4 haloalkoxy, and provided when at least one of $R^{2a}$, $R^{2b}$, $R^{2c}$, $R^{2d}$, and $R^{2e}$ is C1-C4 alkoxy and $R^1$ is C1-C8 acyclic alkyl, then $R^1$ is substituted with 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl), or a pharmaceutically acceptable salt thereof.

In one aspect, disclosed are methods for modifying a proteasome in a subject, the method comprising the step of administering to the subject an effective amount of a compound having a structure selected from:

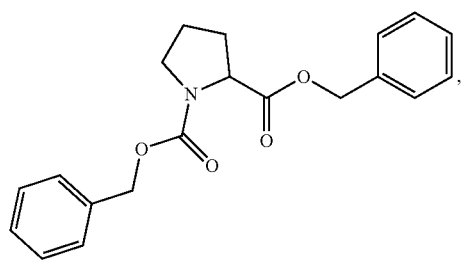

or a pharmaceutically acceptable salt thereof.

In a further aspect, the proteasome is 26 S proteasome or 20 S proteasome.

In a further aspect, modifying is inhibiting.

In a further aspect, the compound exhibits inhibition of proteasome activity. In a still further aspect, the compound exhibits a decrease in proteasome activity.

In a further aspect, the compound exhibits inhibition of proteasome activity with an IC$_{50}$ of from about 0.001 µM to about 25 µM. In a still further aspect, the compound exhibits inhibition of proteasome activity with an IC$_{50}$ of from about 0.001 µM to about 15 µM. In yet a further aspect, the compound exhibits inhibition of proteasome activity with an IC$_{50}$ of from about 0.001 µM to about 10 µM. In an even further aspect, the compound exhibits inhibition of proteasome activity with an IC$_{50}$ of from about 0.001 µM to about 5 µM. In a still further aspect, the compound exhibits inhibition of proteasome activity with an IC$_{50}$ of from about 0.001 µM to about 1 µM. In yet a further aspect, the compound exhibits inhibition of proteasome activity with an IC$_{50}$ of from about 0.001 µM to about 0.5 µM. In an even further aspect, the compound exhibits inhibition of proteasome activity with an IC$_{50}$ of from about 0.001 µM to about 0.1 µM. In a still further aspect, the compound exhibits inhibition of proteasome activity with an IC$_{50}$ of from about 0.001 µM to about 0.05 µM. In yet a further aspect, the compound exhibits inhibition of proteasome activity with an IC$_{50}$ of from about 0.001 µM to about 0.01 µM. In an even further aspect, the compound exhibits inhibition of proteasome activity with an IC$_{50}$ of from about 0.001 µM to about 0.005 µM. In a still further aspect, the compound exhibits inhibition of proteasome activity with an IC$_{50}$ of from about 0.005 μM to about 25 μM. In yet a further aspect, the compound exhibits inhibition of proteasome activity with an IC$_{50}$ of from about 0.01 μM to about 25 μM. In an even further aspect, the compound exhibits inhibition of proteasome activity with an IC$_{50}$ of from about 0.05 μM to about 25 μM. In a still further aspect, the compound exhibits inhibition of proteasome activity with an IC$_{50}$ of from about 0.1 μM to about 25 μM. In yet a further aspect, the compound exhibits inhibition of proteasome activity with an IC$_{50}$ of from about 0.5 μM to about 25 μM. In an even further aspect, the compound exhibits inhibition of proteasome activity with an IC$_{50}$ of from about 1 μM to about 25 μM. In a still further aspect, the compound exhibits inhibition of proteasome activity with an IC$_{50}$ of from about 5 μM to about 25 μM. In yet a further aspect, the compound exhibits inhibition of proteasome activity with an IC$_{50}$ of from about 10 μM to about 25 μM. In an even further aspect, the compound exhibits inhibition of proteasome activity with an IC$_{50}$ of from about 15 μM to about 25 μM.

In a further aspect, the subject is a mammal. In a still further aspect, the mammal is human.

In a further aspect, the effective amount is a therapeutically effective amount. In a still further aspect, the effective amount is a prophylactically effective amount.

In a further aspect, the subject has been diagnosed with a need for modifying a proteasome prior to the administering step. In a still further aspect, the subject has been diagnosed with a need for treatment of a disorder of uncontrolled cellular proliferation prior to the administering step.

In a further aspect, the method further comprises the step of identifying a subject in need of treatment of a disorder of uncontrolled cellular proliferation.

In a further aspect, the disorder of uncontrolled cellular proliferation is a cancer. In a still further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

G. Methods of Modifying a Proteasome in at Least One Cell

In one aspect, disclosed are methods of modifying a proteasome in at least one cell, the method comprising the step of contacting the at least one cell with an effective amount of at least one disclosed compound, or a pharmaceutically acceptable salt thereof. In a further aspect, modulating is inhibiting.

In one aspect, disclosed are methods of modulating pantothenate kinase activity in at least one cell, the method comprising the step of contacting the at least one cell with an effective amount of at least one compound having a structure represented by a formula selected from:

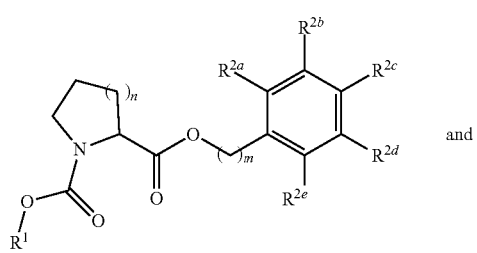

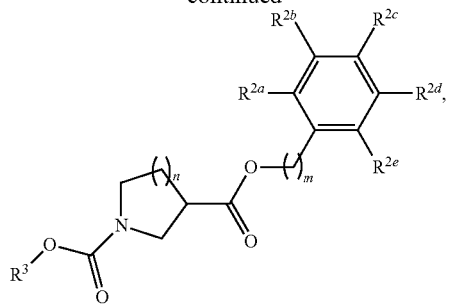

wherein n is 1 or 2; wherein m is 1, 2, or 3; wherein R$^1$ is selected from (CH$_2$)$_q$Cy$^1$, Cy, and C1-C8 acyclic alkyl substituted with 0, 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl); wherein q, when present, is 1, 2, or 3; wherein each of R$^{20a}$ and R$^{20b}$, when present, is independently selected from hydrogen and C1-C4 alkyl; wherein Cy$^1$ is selected from cyclohexyl and 6-membered monocyclic aryl, and is substituted with 0, 1, 2, or 3 groups independently selected from halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein each of R$^{2a}$, R$^{2b}$, R$^{2c}$, R$^{2d}$, and R$^{2e}$ is independently selected from hydrogen, halogen, —CN, —NH$_2$, —NO$_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein R$^3$, when present, is selected from C1-C8 alkyl, (CH$_2$)$_q$Cy$^1$, and Cy$^1$, provided at least one of R$^{2a}$, R$^{2b}$, R$^{2c}$, R$^{2d}$, and R$^{2e}$ is —OH, C1-C4 alkoxy, or C1-C4 haloalkoxy, and provided when at least one of R$^{2a}$, R$^{2b}$, R$^{2c}$, R$^{2d}$, and R$^{2e}$ is C1-C4 alkoxy and R$^1$ is C1-C8 acyclic alkyl, then R$^1$ is substituted with 1, 2, or 3 groups independently selected from halogen, —CN, —NH$_2$, —NO$_2$, —OH, —C(O)NR$^{20a}$R$^{20b}$, —CO$_2$H, and —CO$_2$(C1-C4 alkyl), or a pharmaceutically acceptable salt thereof.

In one aspect, disclosed are methods of modulating pantothenate kinase activity in at least one cell, the method comprising the step of contacting the at least one cell with an effective amount of at least one compound having a structure selected from:

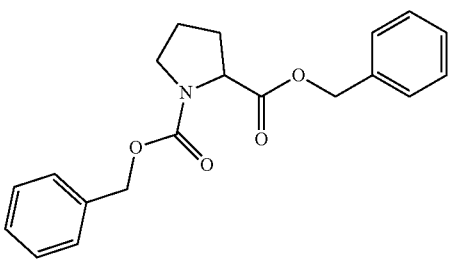

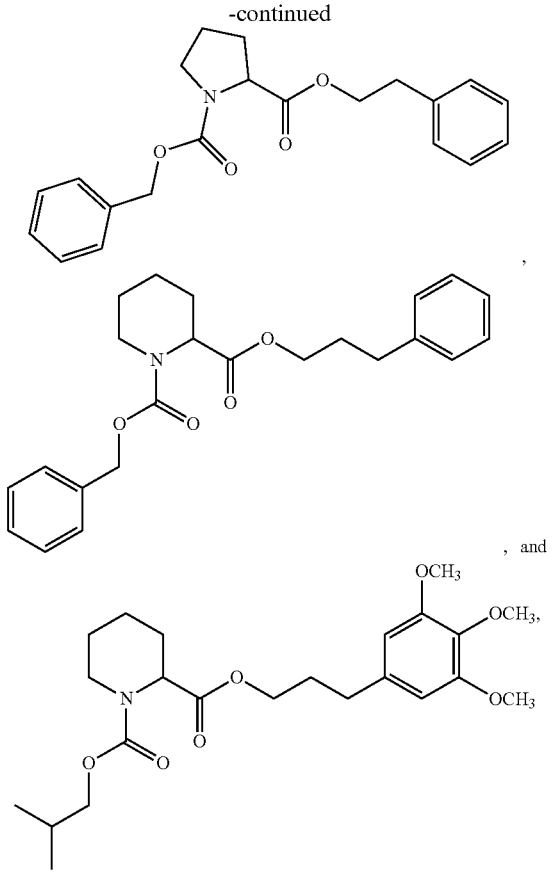

or a pharmaceutically acceptable salt thereof.

In a further aspect, the cell is mammalian. In a still further aspect, the cell is human. In yet a further aspect, the cell has been isolated from a mammal prior to the contacting step. In an even further aspect, the cell has been isolated from a human prior to the contacting step.

In a further aspect, contacting is via administration to a mammal. In a still further aspect, the mammal has been diagnosed with a need for treatment of a disorder of uncontrolled cellular proliferation prior to the administering step. In yet a further aspect, the disorder of uncontrolled cellular proliferation is a cancer. In an even further aspect, the mammal has been diagnosed with a need for modifying a proteasome prior to the administering step.

In a further aspect, modifying is inhibiting.

H. Methods of Effecting Immunosuppression in a Subject

In one aspect, disclosed are methods of effecting immunosuppression in a subject, the method comprising the step of administering to the subject an effective amount of at least one disclosed compound, or a pharmaceutically acceptable salt thereof.

In one aspect, disclosed are methods of effecting immunosuppression in a subject, the method comprising the step of administering to the subject an effective amount of a compound having a structure represented by a formula selected from:

wherein n is 1 or 2; wherein m is 1, 2, or 3; wherein $R^1$ is selected from $(CH_2)_q Cy$, Cy, and C1-C8 acyclic alkyl substituted with 0, 1, 2, or 3 groups independently selected from halogen, —CN, —$NH_2$, —$NO_2$, —OH, —C(O)$NR^{20a}R^{20b}$, —$CO_2H$, and —$CO_2$(C1-C4 alkyl); wherein q, when present, is 1, 2, or 3; wherein each of $R^{20a}$ and $R^{20b}$, when present, is independently selected from hydrogen and C1-C4 alkyl; wherein $Cy^1$ is selected from cyclohexyl and 6-membered monocyclic aryl, and is substituted with 0, 1, 2, or 3 groups independently selected from halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; wherein each of $R^{2a}$, $R^{2b}$, $R^{2c}$, $R^{2d}$, and $R^{2e}$ is independently selected from halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein $R^3$, when present, is selected from C1-C8 alkyl, $(CH_2)_q Cy^1$, and Cy, provided at least one of $R^{2a}$, $R^{2b}$, $R^{2c}$, $R^{2d}$, and $R^{2e}$ is C1-C4 alkoxy or C1-C4 haloalkoxy, and provided when at least one of $R^{2a}$, $R^{2b}$, $R^{2c}$, $R^{2d}$, and $R^{2e}$ is C1-C4 alkoxy and $R^1$ is CT-C8 acyclic alkyl, then $R^1$ is substituted with 1, 2, or 3 groups independently selected from halogen, —CN, —$NH_2$, —$NO_2$, —OH, —C(O)$NR^{20a}R^{20b}$, —$CO_2H$, and —$CO_2$(C1-C4 alkyl), or a pharmaceutically acceptable salt thereof.

In one aspect, disclosed are methods of effecting immunosuppression in a subject, the method comprising the step of administering to the subject an effective amount of a compound having a structure selected from:

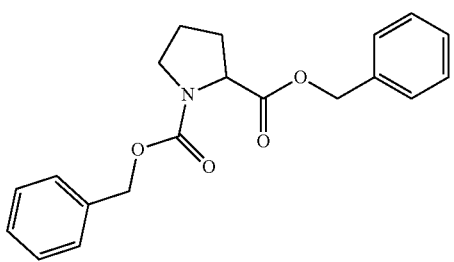

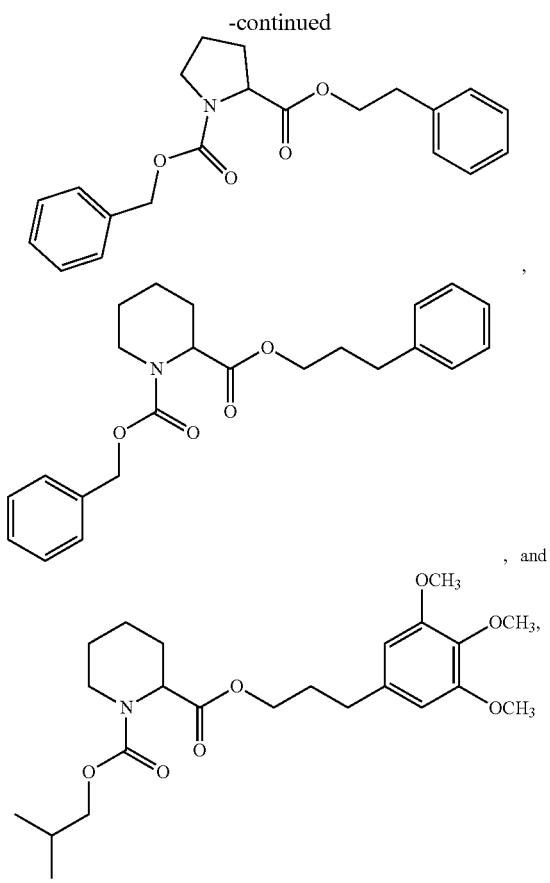

, and or a pharmaceutically acceptable salt thereof.

In a further aspect, the subject is a mammal. In a still further aspect, the mammal is human.

In a further aspect, the effective amount is a therapeutically effective amount. In a still further aspect, the effective amount is a prophylactically effective amount.

In a further aspect, the subject has been diagnosed with a need for immunosuppression prior to the administering step. In a still further aspect, the subject has been diagnosed with a need for treatment of a disorder of uncontrolled cellular proliferation prior to the administering step. In yet a further aspect, the disorder of uncontrolled cellular proliferation is a cancer.

In a further aspect, the method further comprises the step of identifying a subject in need of immunosuppression.

I. Methods of Using the Compounds and Compositions

Provided are methods of using of a disclosed compound or composition. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, the invention relates to a method for the manufacture of a medicament for treating a disorder of uncontrolled cellular proliferation such as, for example, a cancer, in a mammal, the method comprising combining a therapeutically effective amount of a disclosed compound or product of a disclosed method with a pharmaceutically acceptable carrier or diluent.

With regard to these applications, the present method includes administration to an animal, particularly a mammal, and more particularly a human, of a therapeutically effective amount of the compound effective in the inhibition of a proteasome and especially 26 S proteasome or 20 S proteasome. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the disorder.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

2. Use of Compounds and Compositions

Also provided are the uses of the disclosed compounds and compositions.

Thus, in one aspect, the invention relates to the uses of modulators of a proteasome such as, for example, 26 S proteasome or 20 S proteasome.

In a further aspect, the invention relates to the use of a disclosed compound or product of a disclosed method in the manufacture of a medicament for the treatment of a disorder associated with proteasome activity such as, for example, a cancer.

In a further aspect, the use relates to a process for preparing a pharmaceutical composition comprising a therapeutically effective amount of a disclosed compound or a product of a disclosed method, and a pharmaceutically acceptable carrier, for use as a medicament.

In a further aspect, the use relates to a process for preparing a pharmaceutical composition comprising a therapeutically effective amount of a disclosed compound or a product of a disclosed method, wherein a pharmaceutically acceptable carrier is intimately mixed with a therapeutically effective amount of the disclosed compound or the product of a disclosed method.

In various aspects, the use relates to the treatment of a cancer in a vertebrate animal. In a further aspect, the use relates to the treatment of a cancer in a human subject.

In a further aspect, the use is the treatment of a disorder of uncontrolled cellular proliferation. In a still further aspect, the disorder of uncontrolled cellular proliferation is a cancer. In yet a further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

It is understood that the disclosed uses can be employed in connection with the disclosed compounds, methods, compositions, and kits. In a further aspect, the invention relates to the use of a disclosed compound or composition of a medicament for the treatment of a disorder associated with proteasome activity in a mammal.

In a further aspect, the invention relates to the use of a disclosed compound or composition in the manufacture of a medicament for the treatment of a disorder associated with proteasome activity selected from a cancer.

3. Kits

In various aspects, disclosed are kits comprising at least one disclosed compound or composition, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

In one aspect, disclosed are kits comprising at least one compound having a structure represented by a formula selected from:

wherein n is 1 or 2; wherein m is 1, 2, or 3; wherein $R^1$ is selected from $(CH_2)_qCy^1$, $Cy^1$, and C1-C8 acyclic alkyl substituted with 0, 1, 2, or 3 groups independently selected from halogen, —CN, —$NH_2$, —$NO_2$, —OH, —C(O)$NR^{20a}R^{20b}$, —$CO_2H$, and —$CO_2$(C1-C4 alkyl); wherein q, when present, is 1, 2, or 3; wherein each of $R^{20a}$ and $R^{20b}$, when present, is independently selected from hydrogen and C1-C4 alkyl; wherein $Cy^1$ is selected from cyclohexyl and 6-membered monocyclic aryl, and is substituted with 0, 1, 2, or 3 groups independently selected from halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; wherein each of $R^{2a}$, $R^{2b}$, $R^{2c}$, $R^{2d}$, and $R^{2e}$ is independently selected from halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein $R^3$, when present, is selected from C1-C8 alkyl, $(CH_2)_qCy^1$, and $Cy^1$, provided at least one of $R^{2a}$, $R^{2b}$, $R^{2c}$, $R^{2d}$, and $R^{2e}$ is C1-C4 alkoxy or C1-C4 haloalkoxy, and provided when at least one of $R^{2a}$, $R^{2b}$, $R^{2c}$, $R^{2d}$, and $R^{2e}$ is C1-C4 alkoxy and $R^1$ is C1-C8 acyclic alkyl, then $R^1$ is substituted with 1, 2, or 3 groups independently selected from halogen, —CN, —$NH_2$, —$NO_2$, —OH, —C(O)$NR^{20a}R^{20b}$, —$CO_2H$, and —$CO_2$(C1-C4 alkyl), or a pharmaceutically acceptable salt thereof, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

In one aspect, disclosed are kits comprising at least one compound having a structure selected from:

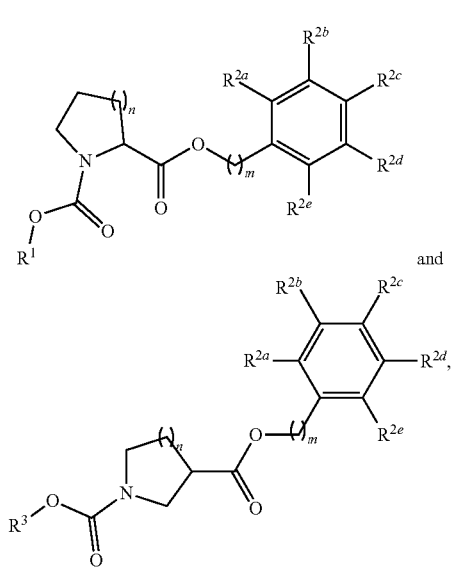

and

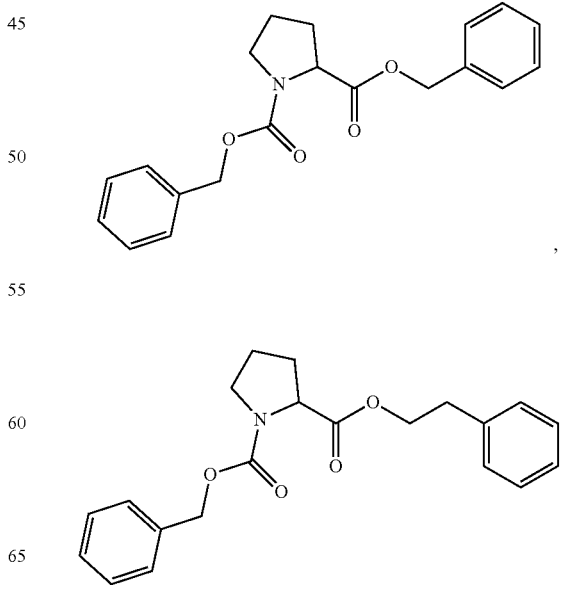

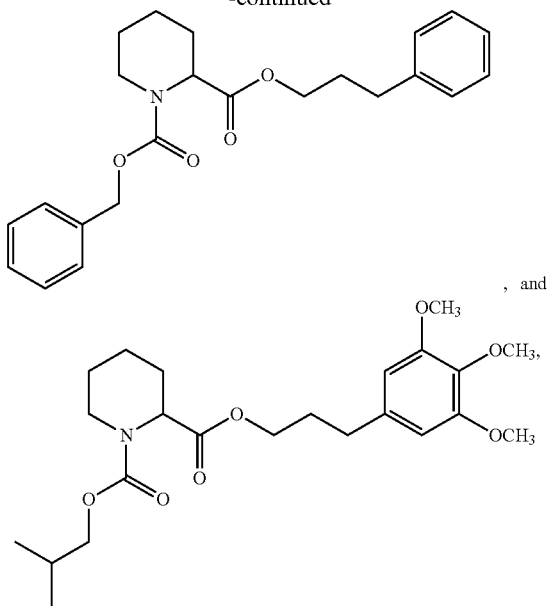

, and or a pharmaceutically acceptable salt thereof, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

In various aspects, the agents and pharmaceutical compositions described herein can be provided in a kit. The kit can also include combinations of the agents and pharmaceutical compositions described herein.

In various aspects, the informational material can be descriptive, instructional, marketing or other material that relates to the methods described herein and/or to the use of the agents for the methods described herein. For example, the informational material may relate to the use of the agents herein to treat a subject who has, or who is at risk for developing, a disorder associated with proteasome activity. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, a disorder associated with proteasome activity.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the compound and the at least one agent are co-formulated. In a still further aspect, the compound and the at least one agent are co-packaged.

In a further aspect, the at least one agent is a chemotherapeutic agent. In a still further aspect, the chemotherapeutic agent is selected from an alkylating agent, an antimetabolite agent, an antineoplastic antibiotic agent, a mitotic inhibitor agent, and a mTor inhibitor agent.

In a further aspect, the chemotherapeutic agent is an antineoplastic antibiotic agent. In a still further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the chemotherapeutic agent is an antimetabolite agent. In a still further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the chemotherapeutic agent is an alkylating agent. In a still further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the chemotherapeutic agent is a mitotic inhibitor agent. In a still further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In a further aspect, the chemotherapeutic agent is a mTor inhibitor agent. In a still further aspect, the mTor inhibitor agent is selected from everolimus, sirolimus, and temsirolimus, or a pharmaceutically acceptable salt, hydrate, solvate, or polymorph thereof.

In a further aspect, the kit further comprises a plurality of dosage forms, the plurality comprising one or more doses; wherein each dose comprises an effective amount of the compound and the at least one agent. In a still further aspect, the effective amount is a therapeutically effective amount. In yet a further aspect, the effective amount is a prophylactically effective amount. In an even further aspect, each dose of the compound and at least one agent are co-packaged. In a still further aspect, each dose of the compound and the at least one agent are co-formulated.

In a further aspect, the disorder of uncontrolled cellular proliferation is a cancer. In a still further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

4. Subjects

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder of uncontrolled cellular proliferation prior to the administering step. In some aspects of the disclosed methods, the subject has been identified with a need for treatment of a disorder of uncontrolled cellular proliferation prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, Pa.). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, N.Y.).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops, syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

J. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals a. 3-(3,4,5-trimethoxyphenyl)propan-1-ol (R2)

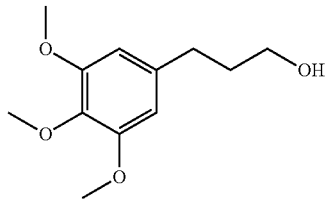 [SMILES: COc1cc(CCCO)cc(OC)c1OC]

To an oven-dried roundbottom flask containing a stir bar was added freshly distilled THF (150 mL). The reaction vessel was immersed in an ice water bath, sealed with a septa, and flushed with nitrogen for 15 minutes while stirring. The septa was removed and lithium aluminum hydride (LAH) was added slowly (1.70 g, 45.0 mmol). The vessel was sealed and flushed with nitrogen for 10 minutes. To the reaction mixture was added dropwise via syringe 3,4,5-trimethoxycinnamic acid (9.94 g, 42.0 mmol, dissolved in 80 mL THF). Vigorous bubbling was observed. The reaction was allowed to warm to room temperature and continued overnight. The next day, the reaction mixture was cooled to 0° C. in an ice water bath and methanol was added dropwise until no gas evolution was observed. After this, concentrated HCl was added dropwise until no gas evolution was observed. The reaction mixture was removed from the ice bath and stirred at room temperature for 20 minutes. The crude reaction mixture was concentrated in vacuo to approximately one-third the original volume and transferred to a separatory funnel. To the crude mixture was added water (100 mL) and DCM (100 mL). The reaction mixture was partitioned and extracted with DCM (4×50 mL per extraction). The organic layers were combined and concentrated in vacuo to yield an orange oil that was purified through silica gel chromatography (1:1 ethyl acetate:hexanes, $R_f$=0.24) to yield the product as an oil (4.4 g, 46%). Occasionally the reduction of the allylic alcohol was incomplete, yielding approximately 10% (by $^1$H NMR integration) of the allylic alcohol. This impurity can easily be converted to the alkane through catalytic hydrogenation (hydrogen balloon over 10% palladium on carbon in ethyl acetate). This step was performed as needed. Spectroscopic data matches that reported for this compound. $^1$H NMR (500 MHz) (CDC$_3$) δ: 6.42 (2H, s), 3.85 (3H, s), 3.82 (6H, s), 3.69 (2H, t, J=6.5 Hz), 2.66 (2H, t, J=7.0 Hz), 1.92-1.88 (2H, m), 1.51 (1H, br s). $^{13}$C NMR (125 MHz) (CDC$_3$) δ: 153.1, 137.6, 136.0, 105.2, 62.2, 60.8, 56.0, 34.3, 32.5.

b. 2-(3,4,5-trimethoxyphenyl)ethan-1-ol (R$_2$)

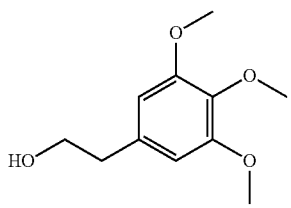

To a 250 mL roundbottom flask was added a stir bar and freshly distilled THF (100 mL). The reaction vessel was cooled in an ice-water bath and stirring commenced. LAH (1.11 g, 30.0 mmol) was added in portions. The reaction vessel was sealed with a septa and flushed with nitrogen. In a separate vessel 3,4,5-trimethoxyphenylacetic acid (4.52 g, 20.0 mmol) was dissolved in THF (30 mL), and was added dropwise to the LAH/THF solution. The reaction was allowed to warm to room temperature and proceed overnight. The following day, the reaction vessel was cooled in an ice-water bath and the reaction was quenched with water (until gas no longer evolved) and concentrated HCl (~ 1 mL). The reaction mixture was partitioned between ethyl acetate (200 mL) and water (100 mL). The organic layer was dried over sodium sulfate and concentrated in vacuo to yield the crude product as a clear, yellow oil. The crude material was purified with silica gel chromatography (1:1 ethyl acetate:hexanes) to yield the final product as a yellow oil that solidified on standing (2.9 g, 68%). Spectroscopic data matches that reported for this compound. $^1$H NMR (500 MHz) (CDC$_3$) δ: 6.45 (2H, s), 3.87-3.83 (11H, m), 2.81 (2H, t, J=7.0, 7.0 Hz). $^{13}$C NMR (125 MHz) (CDCl$_3$) δ: 153.2, 136.5, 134.2, 105.8, 63.5, 60.8, 56.0, 39.5. M.P.=40° C.

c. 1-((benzyloxy)carbonyl)piperidine-2-carboxylic Acid

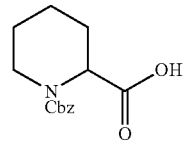 [SMILES: O=C(O)C1CCCCN1C(=O)OCc1ccccc1]

To a 100 mL roundbottom containing a stir bar was added piperidine-2-carboxylic acid (1.29 g, 10.0 mmol) followed by a water:dioxane mixture (40 mL of a 1:1 mixture). Stirring commenced and sodium carbonate was added (2.41 g, 23.0 mmol). Gas evolved; once the evolution had ceased most of the solid had dissolved. To this stirring mixture was added Cbz-Cl (1.7 mL, 2.04 g, 12.0 mmol) dropwise. The reaction mixture was allowed to stir overnight. The following day, the reaction mixture was concentrated to approximately half-volume in vacuo. This mixture was transferred to a separatory funnel and extracted with DCM (50 mL). This extract was discarded. In the separatory funnel, the aqueous layer was acidified by addition of concentrated HCl until the aqueous layer was acidic (pH~2 by pH paper). The acidified aqueous layer was extracted 3 times with DCM (50 mL per extraction). The organic layers were combined and dried over sodium sulfate and concentrated in vacuo to yield the pure product as a clear oil (2.3 g, 88%). Spectroscopic data matches that reported for this compound. $^1$H NMR (500 MHz) (CDCl$_3$) δ: 10.08 (1H, br s), 7.37-7.31 (5H, m), 5.16 (2H, m), 5.01-4.90 (1H, app d), 4.10 (1H, app d), 3.10-2.97 (1H, m), 2.25 (1H, dd, J=27.5, 12.5 Hz), 1.73-1.63 (3H, m), 1.47-1.23 (2H, m). $^{13}$C NMR (125 MHz) (CDCl$_3$) δ: 177.6, 177.5, 156.7, 155.9, 136.4, 128.4, 128.0, 127.8, 67.5, 67.4, 54.3, 54.1, 41.9, 41.7, 26.6, 26.5, 24.6, 24.4, 20.7, 20.6.

d. 1-benzyl 2-(3-(3,4,5-trimethoxyphenyl)propyl) piperidine-1,2-dicarboxylate (2)

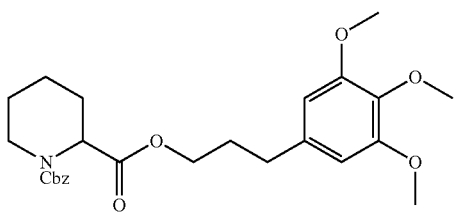 [SMILES: COc1cc(CCCOC(=O)C2CCCCN2C(=O)OCc2ccccc2)cc(OC)c1OC]

To a 250 mL roundbottom flask containing a stir bar and 1-((benzyloxy)carbonyl)piperidine-2-carboxylic acid (5.6 g, 20.0 mmol) was added DCM (100 mL). Stirring commenced and the following reagents were added in the order listed: TEA (4.2 mL, 3.0 g, 30.0 mmol), EDCI (4.20 g, 22.0 mmol), DMAP (0.248 g, 2.0 mmol), and 3-(3,4,5-trimethoxyphenyl) propan-1-ol (4.47 g, 19.8 mmol, dissolved in 10 mL DCM). The reaction mixture was sealed with a septa, flushed with nitrogen, and allowed to proceed overnight. The following day, the reaction mixture was transferred to a separatory funnel and extracted with water. The organic layer was dried over sodium sulfate and concentrated in vacuo to yield the crude product. This material was purified by silica gel chromatography (1:3 ethyl acetate:hexanes, $R_f$=0.22) to yield the pure product as a clear oil (4.7 g, 50%). $^1$H NMR (500 MHz) (CDCl$_3$) (amide rotamers) δ: 7.35-7.25 (5H, m), 6.39-6.36 (2H, m), 5.15-5.10 (2H, m), 4.97-4.85 (1H, m), 4.17-4.04 (3H, m), 3.83-3.82 (9H, m), 3.10-2.94 (1H, app dt), 2.40-2.55 (2H, m), 1.98-1.88 (2H, m), 1.71-1.62 (3H, m), 1.47-1.39 (1H, m), 1.29-1.21 (1H, m). $^{13}$C NMR (125 MHz) (CDC$_3$) (amide rotamers) δ: 171.6, 153.1, 136.7, 136.5, 136.1, 128.4, 127.9, 127.7, 105.2, 67.3, 67.2, 64.2, 60.8, 56.0, 54.6, 54.4, 41.9, 32.4, 30.3, 26.7, 24.7, 24.5, 20.7, 20.6. HRMS calc'd for [M+Na]=494.2155, observed=494.2157. IR (NaCl, DCM): 2941, 1736, 1701, 1589, 1508, 1336, 1164, 1011, 981.

e. 1-((benzyloxy)carbonyl) (S)-piperidine-2-carboxylic Acid (11)

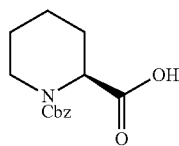 [SMILES: O=C(O)[C@@H]1CCCCN1C(=O)OCc1ccccc1]

To a 100 mL roundbottom containing a stir bar was added (S)-piperidine-2-carboxylic acid (0.500 g, 3.8 mmol) followed by a 1:1 mixture of water:dioxane (20 mL). Stirring commenced and sodium carbonate was added (0.525 g, 5.0 mmol). Gas evolved; once the evolution had ceased most of the solid had dissolved. To this stirring mixture was added Cbz-Cl (0.325 mL, 0.391 g, 2.3 mmol) dropwise. The reaction mixture was allowed to stir overnight. The following day, the reaction mixture was concentrated to approximately half-volume on a rotary evaporator. This mixture was transferred to a separatory funnel and extracted with DCM (50 mL). This extract was discarded. In the separatory funnel, the aqueous layer was acidified by addition of concentrated HCl until the aqueous layer was acidic (pH~2 by pH paper). The acidified aqueous layer was extracted with DCM (3×50 mL). The organic layers were combined and dried over sodium sulfate and concentrated in vacuo to yield the pure product as a clear oil (0.904 g, 89%). Spectroscopic data matches that reported for this compound. $^1$H NMR (500 MHz) (CDCl$_3$)(amide rotamers) δ: 10.08 (1H, br s), 7.37-7.31 (5H, m), 5.16 (2H, m), 5.01-4.90 (1H, app d), 4.10 (1H, app d), 3.10-2.97 (1H, m), 2.25 (1H, dd, J=27.5, 12.5 Hz), 1.73-1.63 (3H, m), 1.47-1.23 (2H, m). $^{13}$C NMR (125 MHz) (CDCl$_3$)(amide rotamers) δ: 177.6, 177.5, 156.7, 155.9, 136.4, 128.4, 128.0, 127.8, 67.5, 67.4, 54.3, 54.1, 41.9, 41.7, 26.6, 26.5, 24.6, 24.4, 20.7, 20.6.

f. 1-benzyl 2-(3-(3,4,5-trimethoxyphenyl)propyl) (S)-piperidine-1,2-dicarboxylate (3)

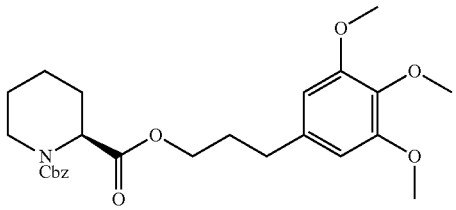 [SMILES: COc1cc(CCCOC(=O)[C@@H]2CCCCN2C(=O)OCc2ccccc2)cc(OC)c1OC]

To a 100 mL roundbottom flask containing a stir bar was added (S)-2-piperidine carboxylic acid (0.250 g, 1.9 mmol), followed by a water:dioxane mixture (10 mL of a 1:1 mixture). Stirring commenced and sodium carbonate was added (0.630 g, 6.0 mmol), followed by Cbz-Cl (0.328 mL, 0.391 g, 2.3 mmol). The reaction mixture was stirred at room temperature for 48 hours. After this time, the reaction mixture was transferred to a separatory funnel and made acidic by the dropwise addition of concentrated HCl (pH~2 measured by pH paper). The acidified reaction mixture was extracted with DCM (3×20 mL). The organic layers were combined, dried over sodium sulfate, and concentrated to dryness in vacuo to yield the crude product as a clear oil (0.432 g, 91%). The crude mixture was carried on to the following step.

To a 50 mL roundbottom flask containing a stir bar was added 1-benzyl 2-(3-(3,4,5-trimethoxyphenyl)propyl) (S)-piperidine-1,2-dicarboxylate (0.432 g, 1.7 mmol) was added DCM (10 mL) followed by TEA (0.696 mL, 0.505 g, 5.0 mmol), EDCI (0.380 g, 2.0 mmol), 3-(3,4,5-trimethoxyphenyl)propan-1-ol (0.384 g, 1.7 mmol), and DMAP (0.024 g, 0.20 mmol). The reaction vessel was sealed, flushed with nitrogen, and stirred overnight. The following day, the reaction mixture was transferred to a separatory funnel and washed with water (50 mL). The organic layer was separated, dried over sodium sulfate, and concentrated in vacuo to yield the product as an oil. The crude material was purified by silica gel chromatography (1:3 ethyl acetate: hexanes, $R_f$=0.22) to obtain the pure product as a clear oil (0.527 g, 66% yield). $^1$H NMR (500 MHz) (CDCl$_3$) (amide rotamers) δ: 7.36-7.30 (5H, m), 6.43-6.37 (2H, m), 5.16-5.11 (2H, m), 4.98-4.86 (1H, m), 4.18-4.05 (3H, m), 3.86-3.83 (9H, m), 3.12-2.89 (1H, m), 2.65-2.56 (2H, m), 2.27-2.12 (1H, m), 2.07-1.89 (2H, m), 1.72-1.63 (2H, m), 1.48-1.40 (1H, m), 1.31-1.22 (1H, m). $^{13}$C NMR (125 MHz) (CDCl$_3$) (amide rotamers) δ: 171.6, 153.1, 136.7, 136.5, 136.2, 128.4, 128.0, 127.7, 105.2, 67.3, 67.2, 64.3, 64.2, 60.8, 56.0, 54.7, 54.4, 41.9, 32.4, 30.3, 30.2, 26.7, 24.7, 24.5, 20.7, 20.6.

HRMS calc'd for [M+H]=472.2335, observed=472.2333. IR (NaCl, DCM): 2942, 1735, 1703, 1590, 1504, 1420, 1334, 1128, 1014.

g. 1-(isobutoxycarbonyl) (S)-piperidine-2-carboxylic Acid

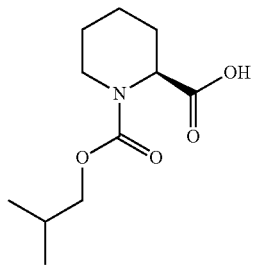 [SMILES: CC(C)COC(=O)N1CCCC[C@H]1C(=O)O]

To a 50 mL roundbottom flask containing a stir bar was added (S)-pipecolic acid (0.250 g, 1.9 mmol) and water (5 mL) followed by 2N aqueous sodium hydroxide (0.200 g, 5.0 mmol in 5 mL water). Stirring commenced and isobutyl chloroformate was added (0.275 mL, 0.285 g, 2.1 mmol). The reaction mixture was allowed to stir overnight. The following day, the reaction was quenched by the addition of concentrated HCl (until the mixture was pH~2 by pH paper) and extracted with ethyl acetate (2×25 mL). The organic layers were combined, dried over sodium sulfate, and concentrated in vacuo to yield the crude product as an oil. The crude material was purified by filtering through a plug of silica gel (1:2 ethyl acetate:hexanes) to yield the pure product as a clear oil which solidifies on standing (0.302 g, 69%). $^1$H NMR (500 MHz) (CDCl$_3$) (amide rotamers) δ: 10.31 (1H, br s), 4.91 (1H, br d), 4.05 (1H, br d), 3.92-3.82 (2H, m), 3.07-2.95 (1H, m), 2.25 (1H, br t, J=14.0 Hz), 1.98-1.90 (1H, m), 1.74-1.65 (3H, m), 1.46-1.40 (1H, m), 1.36-1.28 (1H, m), 0.92 (6H, dd, J=21.0, 7.0 Hz). $^{13}$C NMR (125 MHz) (CDC$_3$) (amide rotamers) δ: 177.7, 177.5, 156.9, 156.2, 71.9, 71.8, 54.2, 54.0, 41.7, 41.5, 27.9, 26.7, 26.5, 24.6, 24.4, 20.7, 20.6, 19.0. HRMS calc'd for [M−H]=228.1241, observed=228.1233. IR (NaCl, DCM): 3095, 2960, 2874, 1744, 1704, 1667, 1470, 1434, 1386, 1259, 1167, 1044, 973. M.P.=67° C.

h. 1-isobutyl 2-(3-(3,4,5-trimethoxyphenyl)propyl) (S)-piperidine-1,2-dicarboxylate (4)

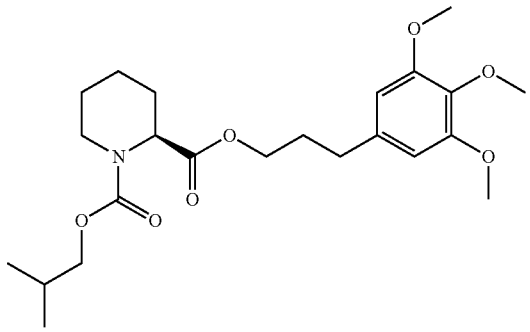 [SMILES: COc1cc(CCCOC(=O)[C@@H]2CCCCN2C(=O)OCC(C)C)cc(OC)c1OC]

To a 100 mL roundbottom flask containing a stir bar was added 1-(isobutoxycarbonyl)piperidine-2-carboxylic acid (0.302 g, 1.32 mmol) followed by DCM (10 mL). To this solution was added 3-(3,4,5-trimethoxyphenyl)propan-1-ol (0.316 g, 1.4 mmol dissolved in 2 mL DCM). Stirring commenced and the following reagents were added in the order listed: EDCI (0.304 g, 1.6 mmol), TEA (0.350 mL, 0.252 g, 2.5 mmol) and DMAP (0.06 g, 0.50 mmol). The reaction vessel was sealed, flushed with nitrogen, and allowed to stir overnight. The following day, the reaction mixture was transferred to a separatory funnel and washed with water (50 mL). The organic layer was dried with sodium sulfate and concentrated in vacuo to yield the crude product as an oil. This material was purified by silica gel chromatography (1:3 ethyl acetate:hexanes, R$_f$=0.32) to yield the pure product as a clear oil (0.301 g, 52% yield). $^1$H NMR (500 MHz) (CDCl$_3$) (amide rotamers) δ: 6.39 (2H, s), 4.95-4.83 (1H, br d), 4.17-3.91 (4H, m), 3.90-3.82 (9H, m), 3.09-2.93 (1H, br dt), 2.62 (2H, br t, J=7.0 Hz), 2.25-2.22 (1H, m), 1.99-1.89 (3H, m), 1.74-1.64 (3H, m), 1.45-1.43 (1H, m), 1.30-1.22 (1H, m), 0.94-0.88 (6H, m). $^{13}$C NMR (125 MHz) (CDCl$_3$) (amide rotamers) δ: 171.8, 171.8, 156.8, 156.2, 153.1, 136.7, 136.2, 105.2, 71.7, 71.6, 64.3, 64.2, 60.8, 56.0, 54.5, 54.3, 41.7, 32.4, 30.3, 30.3, 27.9, 26.8, 26.7, 24.7, 24.5, 20.8, 20.6, 19.0. HRMS calc'd for [M+H]=438.2492, observed=438.2494. IR (NaCl, DCM): 2948, 1735, 1701, 1591, 1457, 1421, 1292, 1016.

i. 1-(methoxycarbonyl) (S)-piperidine-2-carboxylic acid

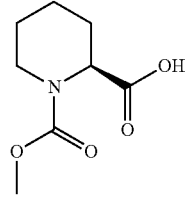

To a 50 mL roundbottom flask containing a stir bar was added (S)-pipecolic acid (0.250 g, 1.9 mmol) and water (5 mL) followed by 2N aqueous sodium hydroxide (0.200 g, 5.0 mmol in 5 mL water). Stirring commenced and methyl chloroformate was added (0.160 mL, 0.198 g, 2.1 mmol). The reaction mixture was allowed to stir overnight. The following day the reaction was quenched with the addition of concentrated HCl (until pH~2 by pH paper) and extracted twice with ethyl acetate (30 mL per extraction). The organic layers were dried over sodium sulfate and concentrated to dryness in vacuo to yield the crude product as a clear oil. The crude material was purified by silica gel chromatography (1:1 ethyl acetate:hexanes) to yield the pure produce as a clear oil (0.238 g, 66%). Spectroscopic data matches that reported for this compound. $^1$H NMR (500 MHz) (CDCl$_3$) (amide rotamers) δ: 9.65 (1H, br s), 4.90 (1H, app d), 4.04 (1H, app dd), 3.72 (3H, app d), 3.06-2.94 (1H, m), 2.25 (1H, br t, J=15.0 Hz), 1.73-1.64 (3H, m), 1.44-1.27 (2H, m). $^{13}$C NMR (125 MHz) (CDC$_3$) (amide rotamers): 177.5, 177.4, 157.3, 156.6, 54.3, 54.0, 53.0, 41.8, 41.6, 26.7, 26.5, 24.6, 24.4, 20.6.

j. 1-methyl 2-(3-(3,4,5-trimethoxyphenyl)propyl) (S)-piperidine-1,2-dicarboxylate (5)

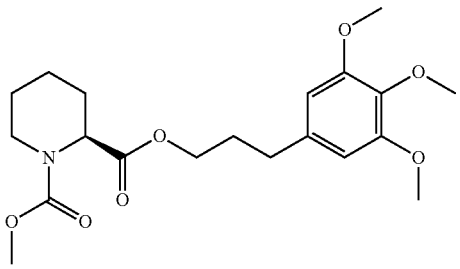 [SMILES: COC(=O)N1CCCC[C@H]1C(=O)OCCCc1cc(OC)c(OC)c(OC)c1]

To a 50 mL roundbottom flask was added 1-(methoxycarbonyl) (S)-piperidine-2-carboxylic acid (0.238 g, 1.32 mmol) followed by DCM (10 mL). Stirring commenced and to the reaction mixture was added the following (in the order listed): EDCI (0.304 g, 1.6 mmol) and DMAP (0.060 g, 0.5 mmol). The reaction vessel was sealed with a septa and flushed with nitrogen. To the stirring reaction mixture was added via syringe (in the order listed): TEA (0.350 mL, 0.252 g, 2.5 mmol) followed by 3-(3,4,5-trimethoxyphenyl)propan-1-ol (0.293 g, 1.3 mmol dissolved in 3.0 mL DCM). The reaction mixture was allowed to stir overnight. The following day, the reaction was quenched by the addition of water (10 mL) and partitioned in a separatory funnel. The organic layer was dried over sodium sulfate and concentrated to dryness in vacuo to yield the crude product as an oil. The crude material was purified by silica gel chromatography (1:2 ethyl acetate:hexanes, $R_f$=0.42) to yield the pure product as a clear oil (0.222 g, 44%). $^1$H NMR (500 MHz) (CDC$_3$) (amide rotamers) δ: 6.39 (2H, s), 4.95-4.80 (1H, m), 4.17-4.11 (2H, m), 3.87-3.82 (9H, m), 3.72-3.70 (3H, m), 3.08-2.92 (1H, m), 2.62 (2H, br t, J=7.0 Hz), 2.25-2.23 (1H, m), 1.96 (2H, quintet, J=7.0 Hz), 1.72-1.63 (4H, m), 1.44-1.42 (1H, br m), 1.29-1.21 (1H, m).). $^{13}$C NMR (125 MHz) (CDCl$_3$) (amide rotamers) δ: 171.7, 15.1, 136.7, 136.2, 105.2, 64.2, 60.8, 56.0, 54.3, 52.8, 41.8, 32.4, 30.3, 26.7, 24.7, 24.5, 20.7. HRMS calc'd for [M+H]=396.2022, observed=396.2019. IR (NaCl, DCM): 2944, 1735, 1699, 1652, 1448, 1242.

k. (R)-1-((benzyloxy)carbonyl)piperidine-3-carboxylic acid

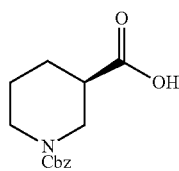 [SMILES: O=C(O)[C@@H]1CCCN(C(=O)OCc2ccccc2)C1]

To a 100 mL roundbottom flask containing a stir bar was added (R)-3-pipecolic acid (1.0 g, 7.7 mmol) followed by 1,4-dioxane (10 mL) and water (10 mL). Stirring commenced and sodium carbonate was added (2.1 g, 20.0 mmol) followed by Cbz-Cl (1.20 mL, 1.44 g, 8.5 mmol). The reaction mixture was stirred overnight. The following day the reaction was quenched by the addition of HCl (36 mmol HCl 10 mL of a 3.6 M solution). The reaction mixture was transferred to a separatory funnel and extracted with ethyl acetate (3×20 mL per extraction). The organic layers were combined, dried over sodium sulfate, and concentrated in vacuo to yield the crude product as an oil. This material was dissolved in a 1:1 mixture of ethyl acetate:hexanes and passed through a plug of silica gel to yield the crude product as a an oil that on standing turns into a waxy, white solid (1.74 g, 84%). $^1$H NMR (500 MHz) (CDC$_3$) (amide rotamers) δ: 7.38-7.29 (5H, m), 5.17-5.10 (2H, m), 4.27-4.15 (1H, m), 3.97 (1H, dt, J=9.5, 3.5, 3.5 Hz), 3.17-3.06 (1H, m), 2.96-2.90 (1H, m), 2.51 (1H, br s), 2.10-2.07 (1H, m), 1.74-1.65 (2H, m) 1.50 (1H, br s). $^{13}$C NMR (125 MHz) (CDCl$_3$) (amide rotamers): 178.8, 155.2, 136.6, 128.5, 128.0, 127.9, 67.2, 45.4, 44.1, 40.9, 27.0, 24.0. HRMS calc'd for [M+H]=264.1236, observed=264.1259; calc'd for [M+Na]=286.1055, observed=286.1058. IR (NaCl, DCM): 3435, 2953, 1732, 1697, 1473, 1291, 1150, 1078. M.P.=97° C.

l. 1-benzyl 3-(3-(3,4,5-trimethoxyphenyl)propyl) (R)-piperidine-1,3-dicarboxylate (6)

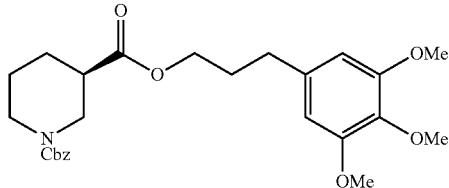 [SMILES: COc1cc(CCCOC(=O)[C@@H]2CCCN(C(=O)OCc3ccccc3)C2)cc(OC)c1OC]

To a 100 mL roundbottom flask containing (R)-1-((benzyloxy)carbonyl)piperidine-3-carboxylic acid (0.542 g, 2.0 mmol) was added a stir bar followed by DCM (15 mL), EDCI (0.414 g, 2.2 mmol), TEA (0.696 mL, 0.505 g, 5.0 mmol), DMAP (0.060 g, 0.5 mmol), and 3-(3,4,5-trimethoxyphenyl)propan-1-ol (0.461 g, 2.0 mmol). The reaction mixture was stirred overnight. The reaction mixture was transferred to a separatory funnel and washed with dilute HCl (10 mL 5% HCl v/v) followed by saturated aqueous sodium bicarbonate (20 mL). The organic layer was dried over sodium sulfate and concentrated in vacuo. The crude material was purified by silica gel chromatography (1:2 ethyl acetate:hexanes) to yield the product as a clear oil (0.453 g, 48%). $^1$H NMR (500 MHz) (CDC$_3$) (amide rotamers) δ: 7.36-7.30 (5H, m), 6.39 (2H, s), 5.16-5.11 (2H, m), 4.28-3.90 (4H, m), 3.84-3.82 (9H, m), 3.15-3.04 (1H, m), 2.95-2.90 (1H, m), 2.62 (2H, br t, J=7.0 Hz), 2.08-2.05 (1H, m), 1.97-1.92 (2H, m), 1.72-1.62 (2H, m), 1.50 (1H, br s). $^{13}$C NMR (125 MHz) (CDCl$_3$) (amide rotamers): 173.2, 155.1, 153.1, 136.8, 136.7, 136.2, 128.5, 128.0, 127.8, 105.2, 67.1, 63.9, 60.8, 56.0, 45.7, 44.2, 41.3, 32.5, 30.2, 27.2, 24.3. HRMS calc'd for [M+H]=472.2335, observed=472.2331. IR (NaCl, DCM): 2491, 1733, 1698, 1589, 1420, 1237, 1127.

m. 1-benzyl 2-(3,4,5-trimethoxyphenethyl) (S)-piperidine-1,2-dicarboxylate (7)

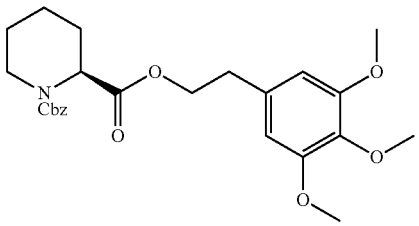 [SMILES: COc1cc(CCOC(=O)[C@@H]2CCCCN2C(=O)OCc2ccccc2)cc(OC)c1OC]

To a 500 mL roundbottom flask containing a stir bar and (S)-1-((benzyloxy)carbonyl)piperidine-2-carboxylic acid (0.386 g, 1.5 mmol) was added DCM (10 mL). Stirring commenced, and in the order listed was added TEA (0.417 mL, 0.303 g, 3.0 mmol), EDCI (0.323 g, 1.7 mmol), DMAP (0.060 g, 0.50 mmol), and 2-(3,4,5-trimethoxyphenyl)ethan-1-ol (0.318 g, 1.5 mmol). The reaction vessel was sealed, flushed with nitrogen, and allowed to stir overnight. The following day, the reaction mixture was quenched with water (10 mL) and partitioned in a separatory funnel. The organic layer was dried over sodium sulfate and concentrated in vacuo to a yellow oil. The crude product was purified by silica gel chromatography (1:3 ethyl acetate:hexanes) to yield the product as a clear oil (0.145 g, 21%). $^1$H NMR (500 MHz) (CDCl$_3$) (amide rotamers) δ: 7.37-7.29 (5H, m), 6.41 (2H, d, J=14.0 Hz), 5.16-5.10 (2H, m), 4.95-4.82 (1H, m), 4.38-4.29 (2H, m), 4.09-3.99 (1H, m), 3.84 (6H, app d, J=3.5 Hz), 3.81 (3H, app d, J=5.0 Hz), 3.00-2.80 (3H, m), 2.17 (1H, t, J=16.0 Hz), 1.67-1.56 (3H, m), 1.43-1.38 (1H, m), 1.55-1.10 (1H, m). $^{13}$C NMR (125 MHz) (CDCl$_3$) (amide rotamers) δ: 171.6, 171.6, 156.5, 155.9, 153.2, 136.6, 136.6, 133.2, 133.1, 128.4, 128.0, 127.8, 105.7, 67.3, 67.1, 65.5, 65.4, 60.8, 56.0, 54.6, 54.4, 41.8, 41.7, 35.4, 35.3, 26.7, 24.6, 24.4, 20.6, 20.5. HRMS calc'd for [M+Na]=480.1998, observed=480.2011. IR (DCM, NaCl): 1746, 1697, 1597, 1421, 1362, 1190, 1022.

n. 1-benzyl 2-(3,4,5-trimethoxybenzyl) piperidine-1,2-dicarboxylate (8)

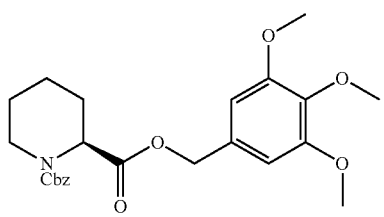 [SMILES: COc1cc(COC(=O)[C@@H]2CCCCN2C(=O)OCc2ccccc2)cc(OC)c1OC]

To a 100 mL roundbottom flask containing a stir bar was added 1-((benzyloxy)carbonyl)piperidine-2-carboxylic acid (0.435 g, 1.6 mmol), followed by DCM 1 mL). The reaction mixture was stirred and the following reagents were added (in the order listed): TEA (0.417 mL, 0.303 g, 3.0 mmol), EDCI (0.342 g, 1.8 mmol), and DMAP (0.060 g, 0.50 mmol). Stirring commenced and the reaction vessel was sealed with a septa and flushed with nitrogen. To this mixture was added 3,4,5-trimethoxybenzyl alcohol (0.273 mL, 0.336 g, 1.7 mmol, dissolved in 2.0 mL DCM) via syringe. The reaction mixture was allowed to stir overnight. The following day, the reaction mixture was transferred to a separatory funnel and extracted with water (50 mL) and brine (50 mL). The organic layer was dried over sodium sulfate and concentrated in vacuo to yield the crude product as a clear oil. The crude material was purified by silica gel chromatography (1:3 ethyl acetate:hexanes, R$_f$=0.28) to yield the final product as a clear oil (0.371 g, 50%). $^1$H NMR (500 MHz) (CDCl$_3$) (amide rotamers) δ: 7.35-7.25 (5H, m), 6.55-6.52 (2H, m), 5.15-4.89 (5H, m), 4.14-4.03 (1H, m), 3.83-3.82 (9H, m), 3.11-2.96 (1H, m), 2.28-2.21 (1H, m), 1.70-1.41 (4H, m), 1.28-1.22 (1H, m). $^{13}$C NMR (125 MHz) (CDCl$_3$) (amide rotamers) δ: 171.5, 156.4, 155.9, 153.3, 137.7, 136.5, 131.4, 131.2, 128.4, 128.4, 128.0, 127.7, 127.6, 104.9, 104.8, 67.3, 67.2, 66.8, 60.8, 56.1, 54.7, 54.4, 41.9, 41.8, 26.7, 24.7, 24.5, 20.7, 20.6. HRMS calc'd for [M+Na]=466.1842, observed=466.1845. IR (NaCl, DCM): 2941, 1734, 1699, 1592, 1457, 1420, 1242, 1192, 1127.

o. 1-benzyl 2-(3-phenylpropyl) (S)-piperidine-1,2-dicarboxylate (9)

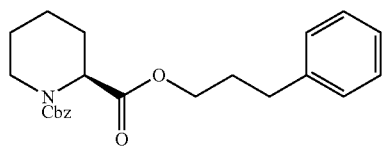 [SMILES: O=C(OCCCc1ccccc1)[C@@H]1CCCCN1C(=O)OCc1ccccc1]

To a 50 mL roundbottom flask containing a stir bar was added 1-((benzyloxy)carbonyl) (S)-piperidine-2-carboxylic acid (0.523 g, 1.98 mmol), followed by DCM (20 mL). To the reaction vessel was added (in the order listed) EDCI (0.45 g, 2.5 mmol), TEA (0.696 mL, 0.505 g, 5.0 mmol), and DMAP (0.060 g, 0.50 mmol). The reaction vessel was sealed and flushed with nitrogen. Stirring commenced and 3-phenyl-1-propanol was added via syringe (0.258 mL, 0.258 g, 1.9 mmol). The reaction was allowed to proceed overnight. The following day, the reaction was transferred to a separatory funnel in which it was washed with water (10 mL), dilute HCl (10 mL 0.5 M HCl), saturated aqueous sodium bicarbonate (20 mL) and brine. The crude product was dried over sodium sulfate and concentrated to dryness in vacuo. The crude product was purified by silica gel chromatography (1:4 ethyl acetate:hexanes, R$_f$=0.30) to yield the pure product as a clear oil (0.276 g, 38%). $^1$H NMR (500 MHz) (CDCl$_3$) (amide rotamers) δ: 7.35-7.13 (10H, m), 5.16-5.13 (2H, m), 4.97-4.85 (1H, m), 4.15-4.05 (3H, m), 3.10-2.94 (1H, m), 2.68-2.61 (2H, m), 2.27-2.19 (1H, m), 1.98-1.89 (2H, m), 1.71-1.62 (3H, m), 1.47-1.41 (1H, m), 1.29-1.21 (1H, m). $^{13}$C NMR (125 MHz) (CDCl$_3$) (amide rotamers) δ: 171.6, 156.5, 155.4, 141.0, 136.6, 128.4, 128.4, 127.9, 127.8, 126.0, 67.3, 67.2, 64.3, 54.6, 54.4, 41.9, 41.8, 32.0, 26.8, 26.7, 24.7, 24.5, 20.7, 20.6. HRMS calc'd for [M+H]=382.2018, observed=382.2044. IR (NaCl, DCM): 3028, 2943, 2860, 1737, 1710, 1454, 1417, 1336, 1255, 1255, 1203, 1163, 1090, 1044.

p. (S)-2-(propoxycarbonyl)piperidin-1-ium Chloride

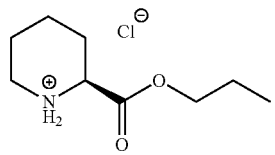

To a 100 mL roundbottom flask containing a stir bar was added (S)-pipecolic acid (0.250 g, 1.9 mmol) and 1-propanol (40 mL). Stirring commenced and thionyl chloride was added to the mixture dropwise (0.5 mL). A reflux condenser was attached to the flask and the reaction mixture was heated to reflux overnight. The following day the reaction mixture was cooled to room temperature and concentrated in vacuo to approximately 20% original volume. To this mixture was added diethyl ether (40 mL). The reaction mixture turned white and solid began to form. The crude mixture was placed in a −20° C. freezer overnight. The following day the solid was filtered and washed with ether. The solid material was dried under vacuum to yield the pure product as a white solid (0.269 g, 68%). $^1$H NMR (500 MHz) ($d_6$-DMSO): 9.69 (1H, br s), 9.37 (1H, br s), 4.16-4.07 (2H, m), 4.04 (1H, dd, J=11.0, 3.5 Hz), 3.20 (1H, br d, J=12.5 Hz), 2.87 (1H, td, J=11.5, 3.0 Hz), 2.07-2.04 (1H, m), 1.72-1.52 (7H, m), 0.89 (3H, t, J=8.0 Hz). $^{13}$C NMR (125 MHz) ($d_6$-DMSO): 169.2, 67.4, 55.9, 43.7, 26.0, 21.8, 21.6, 21.4, 10.6. HRMS calc'd for [M-Cl]=172.1338, observed=172.1333. IR (NaCl, DCM): 1653, 1558, 1456, 1373, 1226. M.P.=162° C.

q. 1-benzyl 2-propyl (S)-piperidine-1,2-dicarboxylate (10)

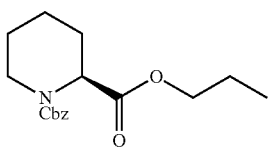 [SMILES: CCCOC(=O)[C@@H]1CCCCN1C(=O)OCc1ccccc1]

To a 50 mL roundbottom flask containing a stir bar was added (S)-2-(propoxycarbonyl)piperidin-1-ium chloride (0.220 g, 1.06 mmol) followed by dioxane (2 mL) and water (2 mL). Stirring commenced and sodium carbonate was added as a solid (0.315 g, 3.0 mmol), followed by Cbz-Cl (0.170 mL, 0.204 g, 1.2 mmol). The reaction mixture was stirred at room temperature overnight. The following day the reaction was quenched by the addition of HCl (24.0 mmol, 2 mL conc. HCl, and 8 mL distilled water). The reaction mixture was transferred to a separatory funnel and extracted with ethyl acetate (3×15 mL per extraction). The crude material was concentrated in vacuo to yield an oil, which was purified by silica gel chromatography (1:2 ethyl acetate:hexanes) to yield the pure product as a clear oil (0.266 g, 75%). $^1$H NMR (500 MHz) (CDC$_3$) (amide rotamers) δ: 7.36-7.30 (5H, m), 5.17-5.09 (2H, m), 4.95-4.83 (1H, m), 4.13-4.03 (3H, m), 3.10-2.94 (1H, m), 2.27-2.19 (1H, m), 1.70-1.58 (5H, m), 1.46-1.40 (1H, m), 1.29-1.21 (1H, m), 0.94-0.88 (3H, m). $^{13}$C NMR (125 MHz) (CDC$_3$) (amide rotamers): 171.7, 171.6, 156.5, 155.9, 136.6, 128.5, 128.4, 127.9, 127.7, 67.2, 67.1, 66.6, 54.6, 54.4, 41.8, 41.8, 26.8, 26.7, 24.7, 24.5, 21.9, 20.7, 20.6, 10.4. HRMS calc'd for [M+H]=306.1705, observed=306.1708. IR (NaCl, DCM): 2979, 1698, 1669, 1540, 1419.

r. ((benzyloxy)carbonyl)-L-proline

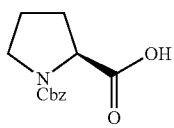 [SMILES: O=C(O)[C@@H]1CCCN1C(=O)OCc1ccccc1]

To a 100 mL roundbottom flask containing a stir bar was added L-proline (1.15 g, 10.0 mmol), followed by a 1:1 water:dioxane mixture (20 mL). Stirring commenced and sodium carbonate (2.41 g, 23.0 mmol) was added in one portion. After gas ceased to evolve, Cbz-Cl was added dropwise (1.7 mL, 1.2 g, 12.0 mmol). The reaction was allowed to stir overnight. The following day, the reaction mixture was transferred to a separatory funnel and extracted with ether twice (50 mL per extraction). The aqueous layer was acidified with concentrated HCl (pH~2 by pH paper) and extracted three times with ethyl acetate (50 mL per extraction). The organic layer was dried over sodium sulfate and concentrated in vacuo to yield the product as a clear oil (2.5 g, 100%). The crude material is suitable for use, but an analytical sample was prepared by purification through silica gel chromatography (elute in 1:4 ethyl acetate:hexanes). Spectroscopic data matches that reported for this compound. $^1$H NMR (500 MHz) (CDCl$_3$)(amide rotamers) δ: 8.76 (1H, br s), 7.38-7.26 (5H, m), 5.22-5.14 (2H, m), 4.41 (1H, doublet of quartets, J=24.5, 8.0, 4.5 Hz), 3.65-3.45 (2H, m), 2.32-1.88 (4H, m) $^{13}$C NMR (125 MHz) (CDCl$_3$)(amide rotamers) δ: 178.2, 176.2, 155.9, 154.4, 136.4, 136.2, 128.5, 128.4, 128.1, 127.9, 127.6, 67.5, 67.1, 59.3, 58.6, 46.9, 46.6, 30.9, 29.2, 24.3, 23.4.

s. 1-benzyl 2-(3-(3,4,5-trimethoxyphenyl)propyl) (S)-pyrrolidine-1,2-dicarboxylate (12)

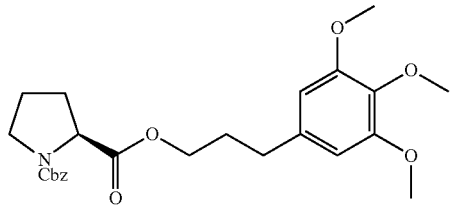 [SMILES: COc1cc(CCCOC(=O)[C@@H]2CCCN2C(=O)OCc2ccccc2)cc(OC)c1OC]

To a 100 mL roundbottom flask containing ((benzyloxy)carbonyl)-L-proline (1.59 g, 6.4 mmol) was added a stir bar and DCM (50 mL). The reaction mixture was stirred and the following reagents were added in the order listed: EDCI (1.33 g, 7.0 mmol), DMAP (0.122 g, 1.0 mmol), and TEA (1.01 g, 10.0 mmol). The reaction vessel was sealed and flushed with nitrogen. To the stirring mixture was added 3-(3,4,5-trimethoxyphenyl)propan-1-ol (1.44 g, 6.4 mmol) via syringe dissolved in DCM (10 mL). The reaction was allowed to stir overnight. The following day, the reaction was quenched with water (50 mL), transferred to a separatory funnel and partitioned. The organic layer was dried over sodium sulfate and concentrated in vacuo. The crude material was purified by silica gel chromatography (1:3 ethyl acetate:hexanes, $R_f$=0.51) to yield the pure product as a clear oil (1.3 g, 42% yield). $^1$H NMR (500 MHz) (CDCl$_3$)(amide rotamers) δ: 7.36-7.24 (5H, m), 6.39-6.34 (2H, app d), 5.19-5.06 (2H, m), 4.38 (1H, ddd, J=19.5, 15.5, 3.5 Hz), 4.19-4.00 (2H, m), 3.84-3.80 (9H, m), 3.66-3.47 (2H, m), 2.62 (1H, t, J=7.5 Hz), 2.51 (1H, t, J=8.0 Hz), 2.28-2.20 (1H, m), 2.02-1.80 (5H, m). $^{13}$C NMR (125 MHz) (CDCl$_3$) (amide rotamers) δ: 172.8, 172.7, 154.8, 154.2, 153.1, 153.1, 136.9, 136.7, 136.6, 136.5, 136.1, 136.1, 128.4, 128.3, 127.9, 127.8, 127.7, 105.2, 105.1, 66.9, 66.9, 64.3, 64.2, 60.8, 59.3, 58.9, 56.0, 46.9, 46.4, 32.3, 32.3, 31.0, 30.3, 30.1, 29.9, 24.3, 23.5. HRMS calc'd for [M+H]=368.1862, observed=368.1869. IR (NaCl, DCM): 2961, 2839, 1734, 1647, 1593, 1507, 1419, 1126, 911.

t. 1-benzyl 2-(3-phenylpropyl) (S)-pyrrolidine-1,2-dicarboxylate (13)

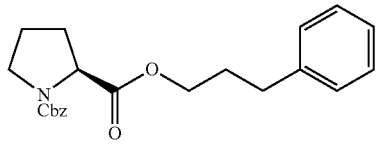 [SMILES: O=C(OCCCc1ccccc1)[C@@H]1CCCN1C(=O)OCc1ccccc1]

To a 250 mL oven dried roundbottom flask containing a stir bar was added ((benzyloxy)carbonyl)-L-proline (2.50 g, 10.0 mmol), followed by DCM (100 mL). Stirring commenced, and to the reaction mixture was added (in the order listed) TEA (1.7 mL, 1.21 g, 12.0 mmol), EDCI (2.0 g, 11.0 mmol), DMAP (0.244 g, 0.2 mmol), and 3-phenyl-1-propanol (1.49 g, 1.49 mL, 11.0 mmol). The reaction vessel was sealed and flushed with nitrogen and allowed to react overnight. The following day, the reaction mixture was transferred to a separatory funnel and extracted with water (once, 100 mL). The crude reaction mixture was concentrated on a rotary evaporator and purified through silica gel chromatography (1:4 ethyl acetate:hexanes, $R_f$=0.33) to yield the pure product as a clear oil (2.1 g, 57%). $^1$H NMR (500 MHz) (CDC$_3$) (amide rotamers) δ: 7.39-7.12 (10H, m), 5.20-5.07 (2H, m), 4.43-4.34 (1H, m), 4.19-4.14 (1H, m), 4.07-3.97 (1H, m), 3.70-3.45 (2H, m), 2.74-2.67 (1H, m), 2.58 (1H, t, J=7.5 Hz), 2.30-2.18 (1H, m), 2.03-1.81 (5H, m). $^{13}$C NMR (125 MHz) (CDCl$_3$) (amide rotamers) δ: 181.3, 172.8, 172.6, 154.3, 141.1, 140.9, 136.7, 136.5, 128.5, 128.4, 128.4, 128.3, 128.3, 127.9, 127.9, 127.8, 127.8, 126.0, 126.0, 125.8, 109.2, 67.0, 66.9, 64.3, 64.3, 62.3, 59.3, 58.9, 46.9, 46.4, 34.2, 32.0, 32.0, 31.9, 30.9, 30.2, 30.0, 29.9, 29.8, 26.8, 24.3, 23.5. HRMS calc'd for [M+H]=368.1826, observed=368.1862. IR (NaCl, DCM): 2955, 1743, 1705, 1652, 1416, 1119, 1088, 746.

u. 1-benzyl 2-phenethyl (S)-pyrrolidine-1,2-dicarboxylate (14)

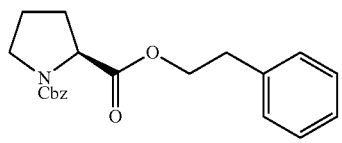 [SMILES: O=C(OCCc1ccccc1)[C@@H]1CCCN1C(=O)OCc1ccccc1]

To a 100 mL roundbottom flask containing a stir bar and ((benzyloxy)carbonyl)-L-proline (2.3 g, 9.2 mmol) was added DCM (50 mL). Stirring commenced and the following reagents were added (in the order listed) EDCI (2.18, 11.5 mmol), TEA (2.52 mL, 2.02 g, 20.0 mmol), DMAP (0.120 g, 0.1 mmol) and 2-phenylethanol (0.976 mL, 0.976 g, 8.0 mmol). The reaction vessel was sealed with a septa and flushed with nitrogen. Stirring commenced and the reaction was allowed to proceed overnight. The following day, the reaction mixture was transferred to a separatory funnel and washed with water (50 mL) and brine (50 mL). The crude material was concentrated in vacuo to yield an oil which was dissolved in a minimum amount of DCM and purified by silica gel chromatography (gradient 1:9 to 1:4 ethyl acetate:hexanes) to yield the product as a clear oil (0.985 g, 33%). $^1$H NMR (500 MHz) (CDCl$_3$) (amide rotamers) δ: 7.40-7.14 (11H, m), 5.24-5.01 (3H, m), 4.48-4.31 (2H, m), 4.27-4.17 (1H, m), 3.66-3.43 (2H, m), 2.96 (1H, t, J=7.0, 7.0 Hz), 2.81 (1H, t, J=7.0, 7.0H), 2.25-1.81 (5H, m). $^{13}$C NMR (125 MHz) (CDCl$_3$) (amide rotamers): 172.7, 172.5, 154.8, 154.2, 137.6, 137.4, 136.7, 136.6, 128.9, 128.8, 128.5, 128.4, 128.4, 128.4, 128.3, 128.2, 128.1, 128.0, 127.9, 127.9, 127.8, 127.8, 127.8, 126.6, 126.5, 67.0, 66.9, 66.9, 66.9, 66.8, 66.7, 65.4, 65.3, 59.2, 58.9, 46.9, 46.9, 46.4, 46.3, 35.0, 34.8, 30.9, 29.8, 24.3, 24.2, 23.5, 23.4. HRMS calc'd for [M+Na]=376.1525, observed=376.1525. IR (NaCl, DCM): 3063, 2956, 1744, 1708, 1586, 1453, 1415, 1352, 1277, 1172, 1088, 999, 749, 699.

v. Dibenzyl (S)-pyrrolidine-1,2-dicarboxylate (15)

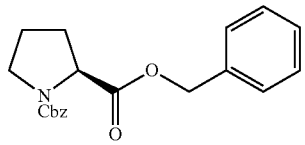 [SMILES: O=C(OCc1ccccc1)[C@@H]1CCCN1C(=O)OCc1ccccc1]

To a 100 mL roundbottom flask containing a stir bar was added benzyl-L-prolinate (purchased from Alfa Aesar, 0.858 g, 4.4 mmol) followed by DCM (20 mL). The vessel was sealed with a septa and flushed with nitrogen. To the stirring reaction mixture was added TEA (0.835 mL, 0.606 g, 6.0 mmol) and Cbz-Cl (0.580 mL, 0.697 g, 4.1 mmol). The reaction mixture was allowed to stir overnight. The following day the reaction mixture was transferred to a separatory funnel and extracted with dilute HCl (20 mL of 5% HCl v/v) and saturated sodium bicarbonate solution (20 mL). The organic layer was dried over sodium sulfate and concentrated in vacuo to yield the crude product. The crude material was purified by silica gel chromatography (1:2 ethyl acetate:hexanes, $R_f$=0.4) to yield the product as a clear oil (0.724 g, 51%). $^1$H NMR (500 MHz) (CDCl$_3$) (amide rotamers) δ: 7.38-7.23 (10H, m), 5.24-5.12 (2H, m), 5.09-5.00 (2H, m), 4.48-4.38 (1H, m), 3.67-6.57 (1H, m), 3.55-3.46 (1H, m), 2.29-2.19 (1H, m), 2.05-1.86 (3H, m). $^{13}$C NMR (125 MHz) (500 MHz) (CDCl$_3$) (amide rotamers) δ: 172.6, 172.4, 154.9, 154.2, 136.7, 136.5, 135.7, 135.5, 128.5, 128.4, 128.4, 128.3, 128.2, 128.1, 128.0, 127.9, 127.9, 127.8, 127.7, 67.0, 66.9, 66.8, 66.7, 59.2, 58.9, 46.9, 46.4, 30.9, 29.9, 24.3, 23.5. HRMS for [M+H]=340.1549, observed=340.1549. IR (NaCl, DCM): 2957, 1744, 1704, 1652, 1416, 1275, 1168, 1087, 986, 697.

2. Determination of Proteasome Activity

Human housekeeping 20 S and 26 S and complexes purified from erythrocytes were purchased from Enzo Life Sciences, Inc. (Farmingdale, N.Y.). The 1 mg/ml stock 20 S proteasome was diluted to 0.2 mg/ml working solution in 50 mM Tris/HCl, pH 8 containing 20% glycerol (dilution buffer). For the 26 S proteasome stock, the dilution buffer was supplemented with 2 mM ATP, 1 mM MgCl$_2$, and 1 mM DTT (dithiothreitol). The ChT-L peptidase activity was measured as arbitrary intensity units of fluorescence emitted by 7-amino-4-methylcoumarin (AMC) released from the canonical model peptide substrate succinyl-LeuLeuValTyr-methylcoumarin (SucLLVY-MCA; Bachem Bioscience Inc., Philadelphia, Pa.), used at concentration of 100 μM. Free AMC (Sigma-Aldrich, St. Louis, Mo.) was used as the standard. The Rpt5 C-terminal peptide was synthesized (standard solid-phase peptide chemistry) and purified to at least 98% purity by GenScript (Piscataway, N.J.). The Rpt5 peptide and the peptide substrate were dissolved in dimethylsulfoxide (DMSO) and such stock solutions were stored at −20° C. The total concentration of DMSO in final reaction mixtures never exceeded 3% (vol/vol).

The reaction was carried out in 96-well plates, in 100 µL of reaction mixture, for 1 hour at 37° C. In the case of 20 S proteasome, the reaction mixture consisted of 45 mM Tris/HCl, pH 8, 100 mM KCl with premixed 10 µM Rpt5 peptide and 100 µM Suc-LLVY-MCA, to which 200 ng (nearly 0.3 nmol) of proteasome and desired concentration of tested compounds in 1 µL of DMSO were added. To test the activity of 26 S proteasome under conditions challenging coordination of the three pairs of peptidase active centers, a mixture of three canonical substrates specific for the ChT-L (SucLLVY-MCA), trypsin-like (T-L; BocLRR-MCA) and caspase-like (Casp-L; Z-LLE-MCA) was used with each of the substrates at 33.3 µM (100 µM of the total substrate concentration). The reaction mixture in this case consisted of 50 mM Tris/HCl, pH 8, 20 mM NaCl, premixed with the substrates and 2 mM ATP, to which 200 ng (nearly 0.1 nmol) of the 26 S working solution and desired concentration of tested compounds in 0.5 µL of DMSO were added. The reaction rates were calculated from a linear segment of kinetic curves constructed from measurements in 1-minutes intervals (Fluoroskan Ascent plate reader; Thermo Fisher Scientific Inc., Waltham, Mass.). Reaction rates were calculated using a linear fit executed by Slope Analyzer and Enzyme Kinetics applications launched within Origin Pro 2017 (OriginLab). Specific activity of the control 20 S proteasome activated with the Rpt5 peptide was in the range of 1.4 to 2.3 nanomoles of AMC product released by 1 mg of 20 S per second (1.95±0.24; n=18). Specific activity of the control 26 S proteasome challenged with three substrates reached on average 0.28±0.06 nanomoles of AMC product released by 1 mg of the enzyme per second (n=6). For comparison, degradation of the canonical Suc-LLVY-MCA substrate by the control 26 S proteasome preceded with a rate in the range of 0.6-0.8 nanomoles of AMC released per mg of the enzyme per second. The data are presented as mean±SD or as a representative set from at least 3 independent experiments.

3. Atomic Force Microscopy (AFM) Imaging

The single molecule imaging of the 20 S proteasome was carried out as previously described, with a scanner E of the Multimode Nanoscope IIIa (Bruker Inc) (Gaczynska and Osmulski (2009) Atomic Force Microscopy as a Tool to Study the Proteasome Assemblies; Osmulski et al. (2009) *Structure* 17(8): 1137-1147. Available from http://www.scopus.com/inward/record.url?eid=2-s2.0-68149164657&partnerID=40&md5=dc5e413998472b20d822db9458de1955). In short, the proteasomes were deposited and electrostatically attached to a muscovite mica substrate, covered with imaging buffer (5 mM Tris/HCl, pH 7) and scanned in tapping mode in fluid using cantilevers with the spring constant of 0.35 N/m from the SNL (Sharp Nitride Lever) probes (Bruker Inc.) tuned to 9-10 kHz. Gentle scanning conditions with the amplitude setpoint in the range of 1.5-2.0V, drive voltage of 300-500 mV and 3.05 Hz scanning rate were used. Scans of 1 µm² fields (512×512 pixels) contained height-mode images of several dozens of top-view ("standing") 20 S proteasome molecules. The gate status was deduced from a profile of raw height values of pixels measured by a probe scanning across the single proteasome particles. The proteasome a face that included the gate was completely rendered by a six-pixel (11-12 nm) scan-line. If the α face scan-line presented a central dip (a local minimum), the particle was classified as containing the open gate. If a plot of height values presented a concave function without a local minimum, the particle was classified as an intermediate conformer. If the function was convex, the particle was classified as containing the closed gate. The "events" of gate opening/closing were analyzed for scans of distinct particles as well as multiple scans of the same particles.

4. Cell Culture

Human multiple myeloma RPMI 8226 cells were purchased from American Type Culture Collection (ATCC; Manassas, Va.) and cultured according to ATCC specifications. The cells (passage 2-4) were treated with compound 3 or the vehicle diluted with the medium 1:1000, for 48 hours. The content of live cells was determined by excluding the Trypan Blue-stained cells. The cells were counted with TC20 Automated Cell Counter (Bio-Rad Laboratories, Hercules, Calif.) and $EC_{50}$ was calculated with Origin Pro 2017 (OriginLab Corporation, Northampton, Mass.). When indicated, the cells were harvested, washed twice in PBS, resuspended in dilution buffer and stored in −80° C. To prepare crude lysates the thawed preparations were vortexed with glass beads and centrifuged for 5 min 5,000×g (4° C.). The supernate was centrifuged for 20 min 14,000×g. The resulting supernate was used as "crude lysate." SDS-PAGE was carried in 12% acrylamide, Tris-glycine gels from Invitrogen. Chameleon Duo (Li-Cor) and Rainbow RPN800E (GE Healthcare) molecular weight standards were separated on each gel alongside lysates. The proteins were transferred to nitrocellulose membrane in a semi-dry system. The membranes were probed with specific primary antibodies from Life Technologies (S6, PS6) and Li-Cor (COX IV), and then with secondary antibodies from Li-Cor. In each experiment visualization of S6, PS6 and COX IV was performed on the same membrane with Odyssey Infrared Imaging System (Li-Cor).

5. Characterization of Exemplary Compounds

The compounds below in Table 1 were synthesized with methods identical or analogous to those described herein. The requisite starting materials were commercially available, described in the literature, or readily synthesized by one skilled in the art of organic synthesis.

TABLE 1

| No. | Structure |
|---|---|
| B1 | 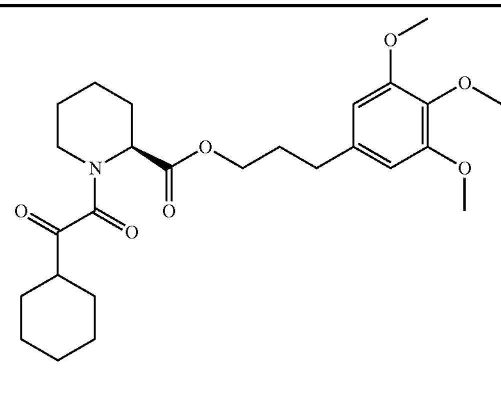 |

TABLE 1-continued

| No. | Structure |
|---|---|
| 2 | (structure) |
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |

6. Development of Pipecolic Ester Analogs

Herein, the development of small molecules with a pharmacophore resembling the "binding domain" of rapamycin are described as novel scaffolds capable of allosteric regulation of the proteasome. These studies extend previous work on a class of B1 compounds derived from the binding domain, which were found to inhibit and destabilize the 26

S proteasome and attenuate proliferation of cultured cancer cells (Gaczynska and Osmulski, unpublished observations).

Without wishing to be bound by theory, a goal was to minimize the structure of rapamycin as a starting point for the design of novel analogs. The piperidine ring was identified in the minimal domain of the parent pharmacophore (FIG. 1), as an ideal starting template for functionalization. For the purpose of substrate minimization, the hemiacetal moiety of the minimal binding domain was replaced with a cyclohexyl moiety ($R_1$), as the requirements of the $R_2$-moiety were investigated (see Table 2 below). The compounds were prepared starting with commercially available C2- or C3-substituted pipecolic acids. Acylation of pipecolic acid with acyl chlorides or chloroformates followed by EDCI coupling of the carboxylic acid with the respective alcohols yielded products 2-11 (Scheme 1). Similarly, acylation of proline using various bencylchlorofromates followed by EDCI coupling of the corresponding alcohols provided 12-15.

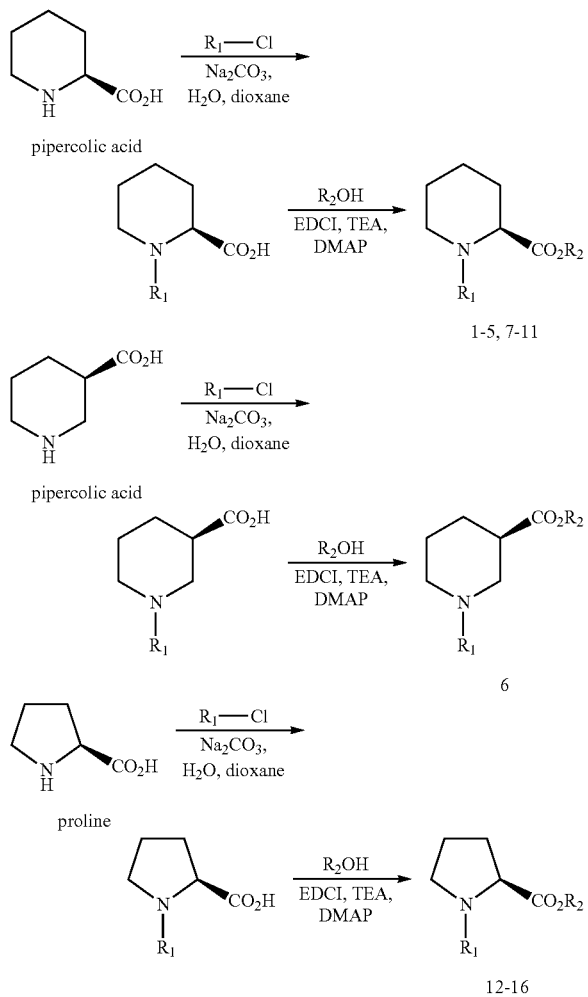

SCHEME 1.

7. Evaluation of 20 S ChT-L Activity by Pipecolic Acid Derivatives

The compounds were evaluated using the 20 S human housekeeping proteasome. It was activated with the Rpt5 derived 10-residue peptide that contains the C-terminal HbYX (hydrophobic-Tyr-any AA) motif activating the proteasome in trans and to some extend mimic the activation by the 19 S regulatory particle (Osmulski and Gaczynska (2013) *Molecular pharmacology* 84: 104-113; Smith et al. (2006) *J. Struct. Biol.* 156: 72-83; Smith et al. (2007) *Mol. Cell* 27: 731-744). Proteolytic activity was monitored over time using a fluorogenic peptide substrate specific for the chymotrypsin-like active center (ChT-L, Suc-LLVY-AMC) in the presence of a concentration range of the inhibitors. In this activity assay, hydrolysis of the substrate results in release of the highly fluorescent aminomethylcoumarin fluorophore. The linear portions of the fluorescence intensity plots were used to calculate the rates of Suc-LLVY-AMC hydrolysis and an $IC_{50}$ (concentration of drug at which 50% of the maximum rate inhibition occurs) is determined. Starting with the $R_1$-moiety, the cyclohexyl-oxoacetamide of the lead agent B1 was replaced with a benzyl carbamate to render an abridged scaffold, compound 2. The racemate compound 2 reduced the ChT-L activity of the proteasome with an $IC_{50}$ of 11.5 µM, which provided a great starting point to interrogate the structural requirements for activity of this new template. Next, the enantiomer of 2 was prepared, compounds (3S) starting from the corresponding chiral pipecolic acids. Gratifyingly, compound 3 was highly effective in reducing ChT-L-proteolysis by the 20 S with $IC_{50}$ of 3.1 µM. Considering the stereochemical match with rapamycin and B1, the structure-activity relationship studies were then focused on the S-enantiomer. Replacement of the benzyl carbamate with the aliphatic mimic carbamate 4, resulted in a significant drop in activity ($IC_{50}$ 15.2 µM). Further reduction of size (methylcarbamate 5) completely abrogated activity. Changes in the positioning of the ester (C-2 substitution versus C-3 substitution) also resulted in a drop in activity (compound 6, $IC_{50}$ 14.7 µM)). In addition, shortening of the $R_2$-chain length from n=3 to n=2 (compound 7) or to one methylene unit (compound 8) also significantly reduced its activity. Fortunately, it was found that the trimethoxy-moieties did not significantly impact the overall potency of the ester side chain and that the free aryl group (compound 9) was found to be a potent 20 S proteasome inhibitor ($IC_{50}$ 2.6 µM). The aryl moiety did seem to be important for activity, since the alkyl ester 10 or carboxylic acid 11 were found to be inactive.

TABLE 2

| No. | n | $R_1$ | $R_2$ | $IC_{50}$ (µM) |
|---|---|---|---|---|
| B1 (±) | 3 | cyclohexyl-oxoacetyl | 3,4,5-trimethoxybenzyl | 5.8 |

TABLE 2-continued

Structure: (S)-piperidine-2-carboxylate with N-R₁ and ester -O-(CH₂)ₙ-R₂

| No. | n | R₁ | R₂ | IC₅₀ (μM) |
|---|---|---|---|---|
| 2 (±) | 3 | -OC(O)OCH₂Ph (benzyl carbamate, Cbz) | 3,4,5-trimethoxyphenyl | 11.5 |
| 3 | 3 | Cbz (benzyl carbamate) | 3,4,5-trimethoxyphenyl | 2.0 |
| 4 | 3 | isobutyl carbamate | 3,4,5-trimethoxyphenyl | 15.2 |
| 5 | 3 | methyl carbamate | 3,4,5-trimethoxyphenyl | >50 |
| 6 (ester in C-3) | 3 | Cbz | 3,4,5-trimethoxyphenyl | 14.7 |
| 7 | 2 | Cbz | 3,4,5-trimethoxyphenyl | 20.1 |
| 8 | 1 | Cbz | 3,4,5-trimethoxyphenyl | 19.8 |
| 9 | 3 | Cbz | phenyl | 2.6 |
| 10 | 3 | Cbz | H | >50 |
| 11 | 0 | Cbz | H | >50 |

8. Evaluation of 20 S CT-L Activity by Proline Derivatives

Next, the ring size requirements were investigated by replacing the pipecolic acid with a proline-type motif. The proline analogues followed the same trends as the pipecolic acid derivatives. The proline derivative 12 only had modest activity, whereas the derivative 13 exhibited good potency (IC$_{50}$ 6.6 μM). Reduction of the R₂-ester side chain length (compounds 14 and 15) also decreased activity, consistent with the trend seen with the pipecolic acids 7 and 8.

TABLE 3

Structure: (S)-pyrrolidine-2-carboxylate with N-R₁ and ester -O-(CH₂)ₙ-R₂

| No. | n | R₁ | R₂ | IC₅₀ (μM) |
|---|---|---|---|---|
| 12 | 3 | Cbz | 3,4,5-trimethoxyphenyl | 23.8 |
| 13 | 3 | Cbz | phenyl | 6.6 |

TABLE 3-continued

[Structure: pyrrolidine with (S) C-2, C-3, N-R₁, and C(=O)-O-(CH₂)ₙ-R₂]

| No. | n | R₁ | R₂ | IC₅₀ (µM) |
|---|---|---|---|---|
| 14 | 2 | -O-C(=O)-O-CH₂-Ph | -CH₂-Ph | 19.2 |
| 15 | 1 | -O-C(=O)-O-CH₂-Ph | -CH₂-Ph | 33.5 |

9. In Silico Docking Studies

Figure 2:
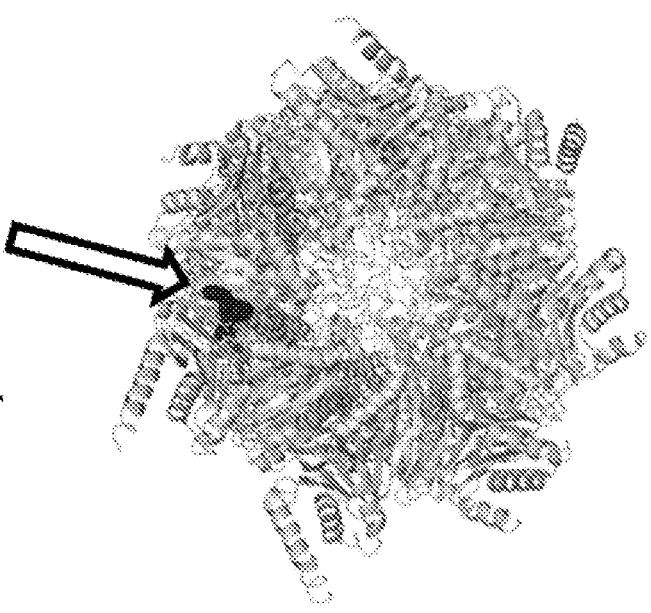
FIG. 2 shows representative side (left) and top (right) view images of the docking of scaffold 3 indicating a preference for binding to the α-ring on the 20 S proteasome.
Figure 2:
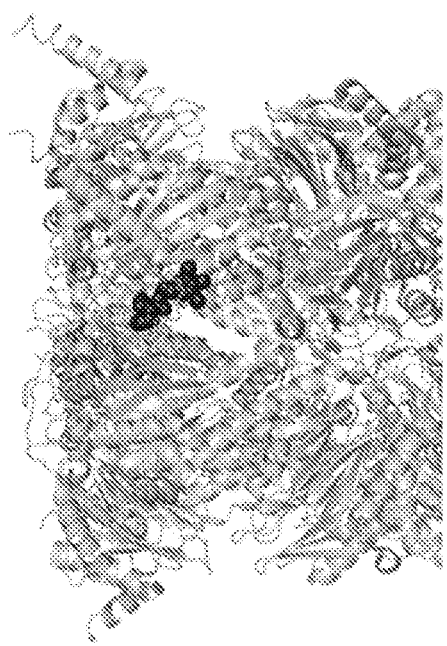

Unbiased in silico docking studies were conducted to gain insight into a possible binding site of the compounds in the 20 S proteasome (Jones et al. (2017) *ACS CHem. Biol.*, ahead of print, DOI 10.1021/acschembio.1027b00489). Autodock Vina run through PyRx was used to manage the workflow (Trott and Olson (2010) *J. Comput. Chem.* 31 455-461; Dallakyan and Olson (2015) *Methods Mol. Biol.* 1263: 243-250). For these studies, several of the most active and inactive agents were examined. The compounds were geometry optimized with the MM2 force field. Autodock Vina identified molecular conformations with the best fit and strongest binding affinity (global minimums). Without wishing to be bound by theory, these docking studies suggest that the compounds bind into the α/α-intersubunit pockets of the α-rings, as seen with endogenous Hb-Y—X-tails of the regulatory particles (RPs or caps) (Schweitzer et al. (2016) *Proceedings of the National Academy of Sciences of the United States of America* 113: 7816-7821). Compound B1 and scaffold 3 indicated a preference for binding deep into the hydrophobic binding pocket below the α2/α3 intersubunit cavity in the α-ring (FIG. 2). The pocket is used as the binding site for the Rpt3 HbYX tail of the 19 S regulatory particle. Other intersubunit pockets, α3/α4 and α6/α7, were also targeted albeit to a lesser extent.

As a next step, further characterization of the selected compounds was attempted. Rapamycin did not affect the activity of fully-assembled 26 S proteasome (Osmulski and Gaczynska (2013) *Molecular pharmacology* 84: 104-113). The single peptidase activities of proteasome treated with B1, compound 3, or compound 9 were affected only at concentrations above 10 M (data not shown). An assay with 26 S proteasome challenged at the same time was designed with substrates specific for all three peptidases. The mixture of substrates required an effort of all active sites, presumably coordinated, similar to the real life protein substrate. In this surrogate proteinase assay the compound 3 outperformed both B1 and compound 9, with $IC_{50}$ values of compound 3=1.2 µM, B1=4.6 µM, and compound 9>60 µM, respectively. Without wishing to be bound by theory, the result suggested a compromised coordination between the active sites, a unique outcome for a compound interacting exclusively or preferentially with the α ring (FIG. 2). This is consistent with the molecular modeling results and further suggests the inter-subunit pocket in the α rings as the binding site.

10. Atomic Force Microscopy (AFM) Imaging

Next, AFM imaging of the native human 20 S core proteasome treated with 10 µM compound 3 was performed to get insight into the putative effects of the compound on the conformation of the α face in the single molecule fashion. In the in-liquid tapping mode AFM method, the outer shape of the α face is monitored by the ultra-sharp probe interacting iuyfdsea with the protein molecule mostly by van der Waals forces (Gaczynska and Osmulski (2008) *Methods Cell Biol.* 90: 39-60). It was previously found that the native 20 S core constantly switches between conformations with a smooth convex or concave/irregular surface of the gate area (Osmulski and Gaczynska (2000) *J. Biol. CHem.* 275: 13171-13174). The former conformers, suggesting a closed gate, prevailed with about 75% of single particle cases (Osmulski and Gaczynska (2000) *J. Biol. CHem.* 275: 13171-13174). Treatment with 10 µM of rapamycin shifted the conformational equilibrium of the 20 S core from about 75% to about 50% of closed-gate molecules (Osmulski and Gaczynska (2013) *Molecular pharmacology* 84: 104-113). An apparent similar shift was induced by compound 3, when the partition of closed conformers dropped from 73±1% (n=4 experiments, 90 events of gate opening/closing) to 45±11% (n=6 experiments, 218 events). Moreover, upon additional refined analysis of "not closed" conformers, it was possible to distinguish the presumably open-gate forms from intermediate forms. While the partition of open forms remained remarkably steady in control and drug-treated proteasomes, the number of intermediates increased significantly. Without wishing to be bound by theory, the result suggests destabilization of the α face and the gate area induced by compound 3 docking in the inter-subunit pocket (see FIG. 2).

Figures 3A, 3B:
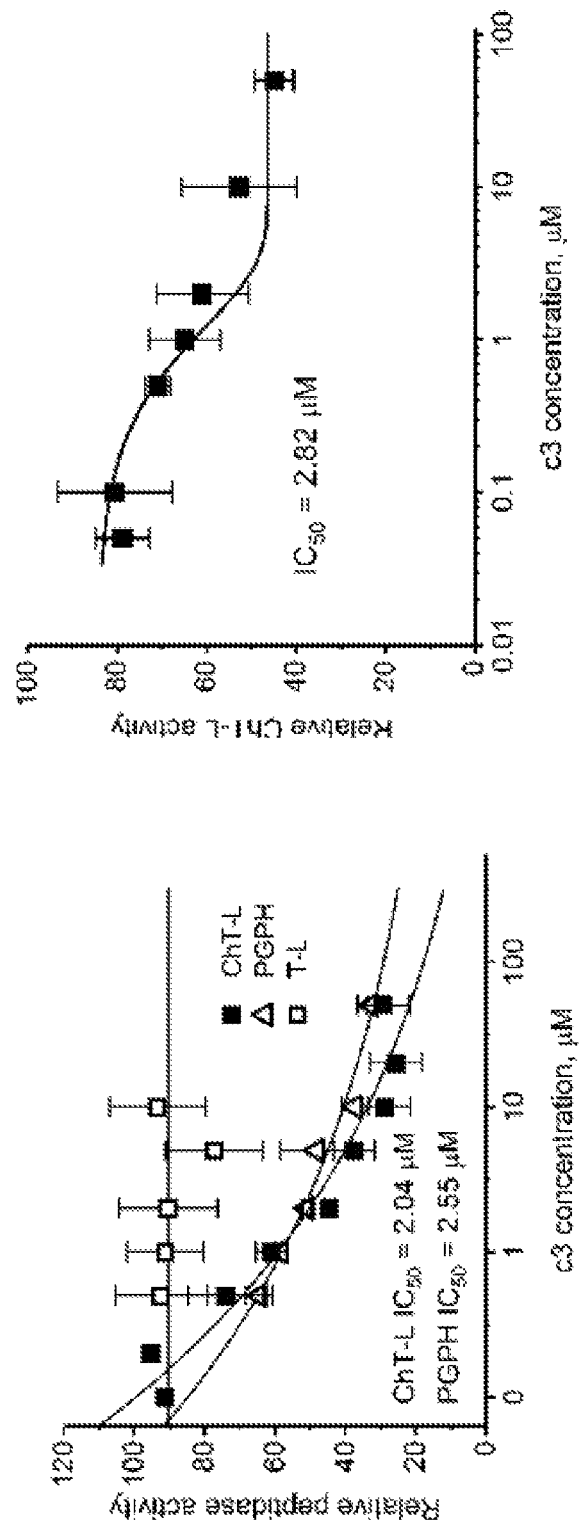
FIG. 3A and FIG. 3B show representative data illustrating that compound 3 inhibits selected peptidase activities of the core 20 S proteasome with low micromolar $IC_{50}$.

11. Compound 3 Inhibits Peptidase Activities of the Proteasome with Low Micromolar Concentrations The leading ChT-L activity of the 20 S proteasome was not the only core peptidase affected by compound 3. The PGPH activity was inhibited as well, with $IC_{50}$ 2.6 µM (FIG. 3A). To the contrary, the T-L peptidase was not affected (FIG. 3A). Apparently, activation of 20 S with tRpt5 was not mandatory to detect inhibition of the workhorse ChT-L peptidase by compound 3. As demonstrated in FIG. 3B, inhibition of the latent core proceeded with a respectable $IC_{50}$ of 2.8 µM; however, it plateaued at about 40% of activity left. Neither PGPH nor T-L peptidases were significantly affected, with $IC_{50}$>50 µM.

Referring to FIG. 3A, not only ChT-L, but also PGPH peptidase, was inhibited with low-micromolar $IC_{50}$ by the compound when the core was activated with ten-residue C-terminal peptide tRpt5 derived from the 19 S ATPase Rpt5. The maximal 10-fold activation was induced by the 10 µM tRpt5, and was used in all the assays. tRpt5 was routinely added to the reaction buffer before the inhibitor. Adding compound 3 before tRpt5 did not significantly affect the proteasome response: the remaining ChT-L activity was 56% 4% (tRpt5 last) versus 53%±7% (tRpt5 1 first; n=3 in both cases).

Referring to FIG. 3B, ChT-L peptidase of the latent core was inhibited by low micromolar concentrations of compound 3. The PGPH peptidase was not affected even by 10 µM compound 3 (99%±14% of control activity; n=5); only 50 µM of compound 3 reduced this activity to 71% 11% of the control (n=3). In turn, the T-L peptidase was weakly inhibited even at low concentrations (with 1 µM of compound 3: 77%±11% of the control; n=3). However, under the assay conditions, the activity was never inhibited more than 50% (with 50 µM of compound 3: 64%±12%; n=4).

12. Evaluation of Conformational Changes in α Face Gate Dynamics Induced by Compound 3

Figure 4:
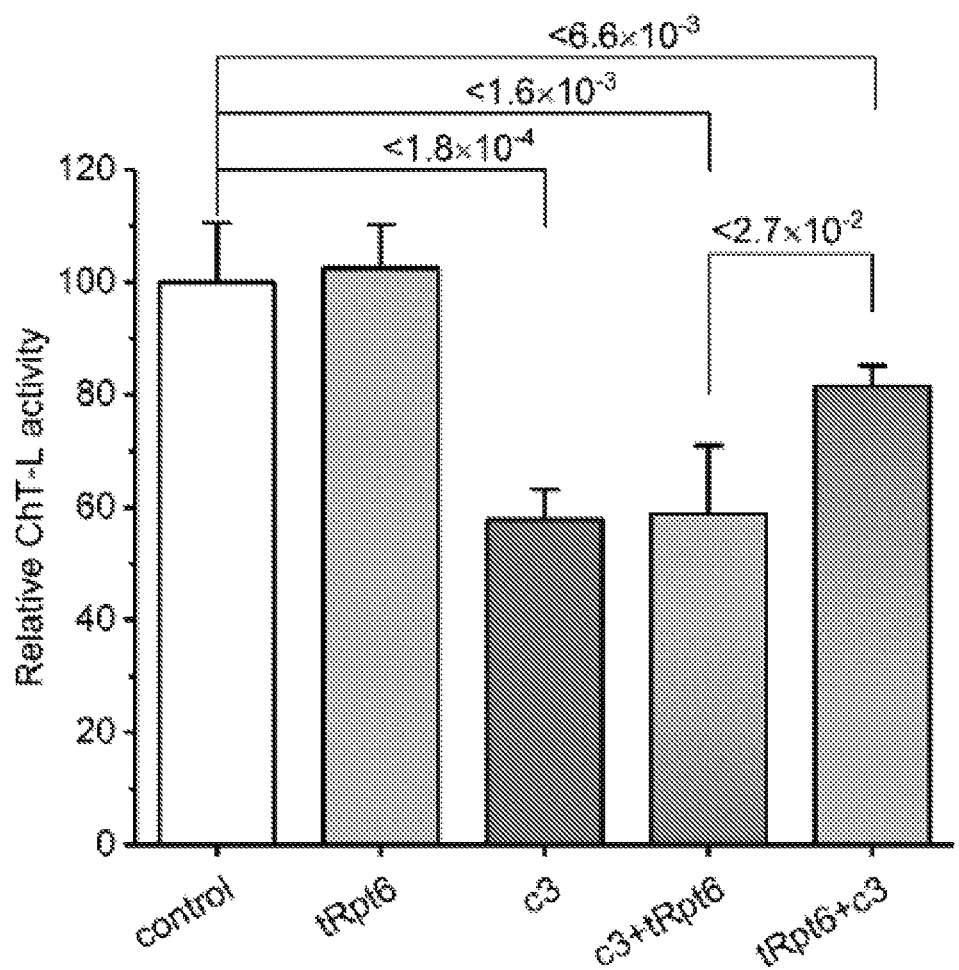
FIG. 4 shows representative data indicating that the C-terminal peptide derived from Rpt6 subunit compromises inhibition of the ChT-L activity of the latent core by the compound 3, however only when added to the proteasome prior to the inhibitor.

Since the α2/α3 cavity has been demonstrated as the docking site of the C-terminal "tail" of the Rpt6 subunit of the regulatory particle (Lander et al. (2012) *Nature* 482 (7384): 186-91; Dong et al. (2010) *Nature* 565(7737): 49-55), the potential competition between compound 3 and the 10-residue peptide derived from C-terminal fragment of Rpt6 (KNMSIKKLWK; tRpt6) was explored. According to the most recent model of the 26 S proteasome dynamic cycle, Rpt6 succeeds the Hb-Y—X containing anchor subunits Rpt5, Rpt3, and Rpt2 in docking into the α face pockets and promoting an intermediate conformation between latent and activated (open gate) proteasomes (Dong et al. (2010) *Nature* 565(7737): 49-55). The C-terminus of the Rpt6 subunit does not display the Hb-Y—X motif and, thus, it is not expected to activate the 20 S core in trans. However, addition of the tRpt6 peptide to the 20 S proteasome before addition of compound 3 significantly attenuated inhibition of the core (FIG. 3A and FIG. 3B). No attenuation was observed when compound 3 was preincubated with the core before addition of tRpt6 (FIG. 4). Without wishing to be bound by theory, this result may be a strong indication of competition between the tRpt6 and compound 3 for binding to the core, consistent with the outcome of in silico docking studies (FIG. 2). For comparison, no competition between tRpt5, expected to occupy the α5/α6 pocket, and compound 3 was detected. The tRpt5 peptide was used at the maximal-activation saturating concentration (10 µM), and the order of addition of tRpt5 and compound 3 did not compromise the inhibition.

Referring to FIG. 4, the C-terminal peptide derived from Rpt6 subunit compromises inhibition of the ChT-L activity of the latent core by the compound 3; however, only when added to the proteasome prior to the inhibitor. The peptide alone did not affect the proteasome activity. 1 µM compound 3 and 2 µM tRpt6 were tested. Mean±SD; n=3 to 6.

13. Compound 3 Destabilizes the α Face of the Proteasome

Figure 5:
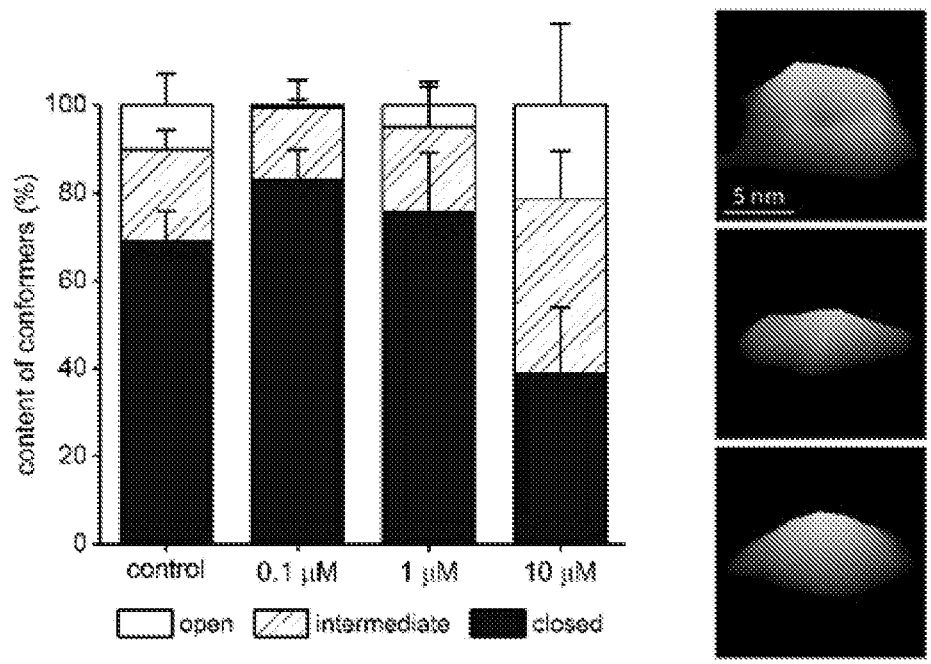
FIG. 5 shows representative data indicating that compound 3 destabilizes the α face of proteasome.
Figure 6B:
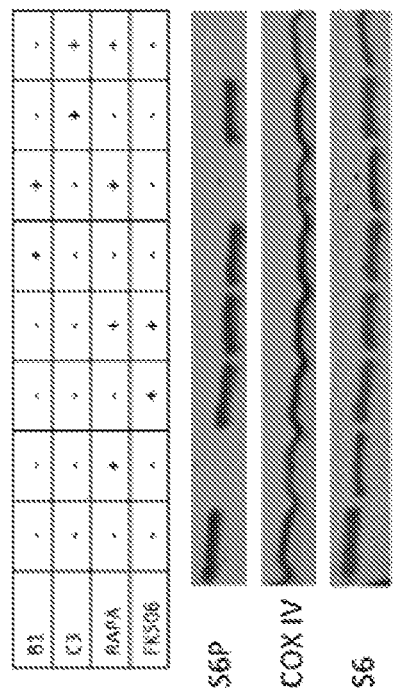
FIG. 6A and FIG. 6B show representative data illustrating that compound 3 inhibits proliferation of human multiple myeloma RPMI 8226 cultured cells. However, it does not target mTOR and FKBP12, the two proteins that rapamycin is binding.
Figure 6A:
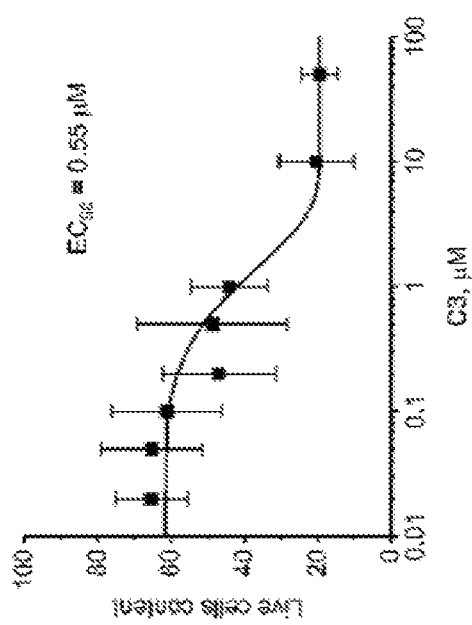

The putative binding site of compound 3 in the α ring pocket, identified by molecular modeling (FIG. 2) and biochemical data (FIG. 4), led to the examination of whether the inhibitor-induced conformational changes in a face gate dynamics. For this purpose, imaging of native 20 S proteasomes was employed using a previously established method of atomic force microscopy (AFM). In this method, topography of the α face of buffer-submerged proteasomes that stand on their opposite a face is rendered in real time by the ultra-sharp probe. A tip of the probe interacts with the molecules mostly by van der Waals forces (Gaczynska and Osmulski (2011) *Methods Mol. Biol.* 736: 117-32). The distribution of conformation types of a face is routinely accessed with sequential scans of fields of multiply randomly distributed proteasomes. Alternatively, consecutive single scan lines representing the gate status of individual particles are collected. The particles are classified as closed-gate if their a face is smooth and regularly concave (FIG. 5). In contrast, the open-gate particles display a centrally placed "crater." In intermediate conformers, the α face forms a slant such that it is not concave and lacks a local-minimum (Gizynska et al. (2019) *J. Med. Chem.* 62(1): 359-70). It was previously found that the native 20 S core constantly switches between these gate conformations. The abundance of conformers depends on a type of the ligand bound to the core. Namely, in the latent core in the absence of any ligands, except water molecules, the closed-gate state prevails (about 75%) (Osmulski and Gaczynska (2002) *Biochemistry* 41(22): 7047-53). Interestingly, the AFM-detected partition of closed (most stable), intermediate and open conformers in the free latent core closely matches conformational landscape of the 19 S-bound core recently revealed by cryoEM studies (Chen et al. (2016) *Proc. Nat. Acad. Sci.* 113(46): 12991-6). Based on the AFM data, a model of the allosteric positive feedback loop between the active centers and the gate was proposed, with the catalytic act prompting gate opening (Osmulski et al. (2009) *Structure* 17(8): 1137-47). Here, it was determined that the presence of only 100 nM compound 3 increased the abundance of closed-gate conformers and rendered the open-gate forms nearly undetectable (FIG. 6A and FIG. 6B). At 1 µM concentration of compound 3, the open-gate proteasomes were detectable again, but their contribution was only about a half of that observed in the control particles. The landscape changed strikingly when the proteasome particles were treated with 10 µM of compound 3. Now, less than a half of the particles were in the closed-gate conformation, and the contribution of open-gate and intermediate forms increased about twice, comparing to the control (see FIG. 5). Without wishing to be bound by theory, this continuous decline of contribution from the closed particles in the inhibitor-treated proteasomes is interpreted to be a result of potential cooperativity between two identical allosteric sites being progressively saturated with compound 3. It is plausible that the higher ligand concentrations limit coordination between the rings leading to a substantially larger representation of the intermediate conformations. Although the proteasomes still could flip between the gate conformations, their peptidolytic capabilities were severely restricted at the highest tested concentration of compound 3. The possibility that the weak attachment of α ring to a mica surface may limit ligand access to the binding site or change the binding site structure or constrain its dynamics effectively producing proteasomes with two binding sites of different ligand affinity cannot be completely excluded. However, such restrictions were not observed with other small ligands (Forster et al. (2005) *Mol. Cell* 18(5): 589-99; Gaczynska and Osmulski (2011) *Methods Mol. Biol.* 736: 117-32). The docking data rather exclude substantial contribution of potential other binding sites since their very weak affinity toward compound 3 was predicted. PR peptides (derivatives of PR39), imidazoline derivative TCH-165, and rapamycin all induced a strong decrease in contribution of the closed forms in the 20 S particles population (Osmulski and Gaczynska (2013) *Mol. Pharmacol.* 84(1): 104-13; Gizynska et al. (2019) J Med. Chem. 62(1): 359-70; Njomen et al. (2018) *Biochemistry* 57(28): 4214-24). The activity of the core proteasome was inhibited or activated by these compounds; however a common trait was destabilization of the 26 S proteasome (Gaczynska et al. (2003) *Biochemistry* 42(29): 8663-70; Osmulski and Gaczynska (2013) *Mol. Pharmacol.* 84(1): 104-13;

Gizynska et al. (2019) *J. Med. Chem.* 62(1): 359-70; Njomen et al. (2018) *Biochemistry* 57(28): 4214-24).

Referring to FIG. 5, compound 3 destabilizes the α face of proteasome. The partition of conformers is shifted toward lower representation of the closed-gate particles and higher of the intermediate and open-gate 20 S proteasomes upon treatment with 10 μM of compound 3 (left panel). 269 events for control and 408 events for compound 3-treated 20 S from 3 independent experiments were analyzed. "Event" was a single run of the AFM probe across the proteasome particle. The differences of abundance between closed and intermediate forms were statistically significant, with $p<0.0001$ and $p<0.0005$ (T test). AFM images (pseudo 3D, 20° tilt) of an α face of typical closed, intermediate and an open particle (top to bottom) are shown in the right panel. The lighter shades of grey represent exposed (higher) portions of the α face of top-view particles.

14. Compound 3 Inhibits Proliferation of Human Multiple Myeloma RPMI 8226 Cultured Cells but does not Target mTOR and FKBP12

The effects of compound 3 observed in vitro prompted its influence on the proliferation of cultured cancer cells to be tested, namely the multiple myeloma RPMI 8226 line. The treatment did lower the content of live cells with $EC_{50}$ of 550 nM (FIG. 6A). Such relatively low $EC_{50}$, as compared to in vitro determined $IC_{50}$ values for peptidase activities (2-3 μM; FIG. 3A and FIG. 3B) should come to no surprise. Even a partial destabilization of proteasome assemblies would be expected to significantly affect physiology of cancer cells. The in vitro readout of single peptidase activities is a useful and convenient measure of the catalytic prowess of proteasome. However, especially in the case of allosteric regulators, it may not fully reflect the important structural and functional effects.

Importantly, neither B1 nor compound 3 affected the activity of mTOR. As demonstrated in FIG. 6B, in the cells treated with B1 or compound 3 the canonical product of mTOR kinase, phosphorylated ribosomal protein S6 (PS6), was readily detectable. Also, even if B1 and compound 3 resemble the binding domain of rapamycin, they did not emulate actions of macrocyclic binding domain mimics such as FK506. FK506 lacks the effector domain needed for mTOR inhibition, however, it binds to FKBP12. When used in excess together with rapamycin that utilizes both FKBP12 and mTOR binding, FK506 abolishes the kinase inhibition. No such actions were detectable with B1 and compound 3 used at concentrations nearing $EC_{50}$ (FIG. 6A and FIG. 6B).

Referring to FIG. 6A, cells were treated with compound 3 or vehicle (DMSO) for 48 hours. The data are averages (±SD) of three-to-five independent experiments.

Referring to FIG. 6B, the Western blotting data presented are representative of three independent experiments. The RPMI 8226 cultured cells were treated for 24 hours with rapamycin (2 nM), a macrocyclic mimic of rapamycin binding domain FK506 (10 μM), compound 3 (0.2 μM) or compound B1 (0.2 μM). Under no conditions did the count of live cells fall below 50% of the control; however, compound 3 and B1 inhibited the cells' proliferation to 60%-65% of control. Crude lysates prepared from the harvested cells were separated by SDS-PAGE, Western blotted, and probed with specific antibodies against the mTOR substrate S6, the product of mTOR kinase PS6 (phosphorylated S6) and a "loading control" housekeeping protein COX IV. Only rapamycin inhibited phosphorylation of S6. In turn, FK506 in combination with rapamycin suppressed the inhibition by competing for binding to FKBP12. Compound 3 and B1 did not inhibit the S6 phosphorylation and did not mimic the actions of FK506.

Figure 7:
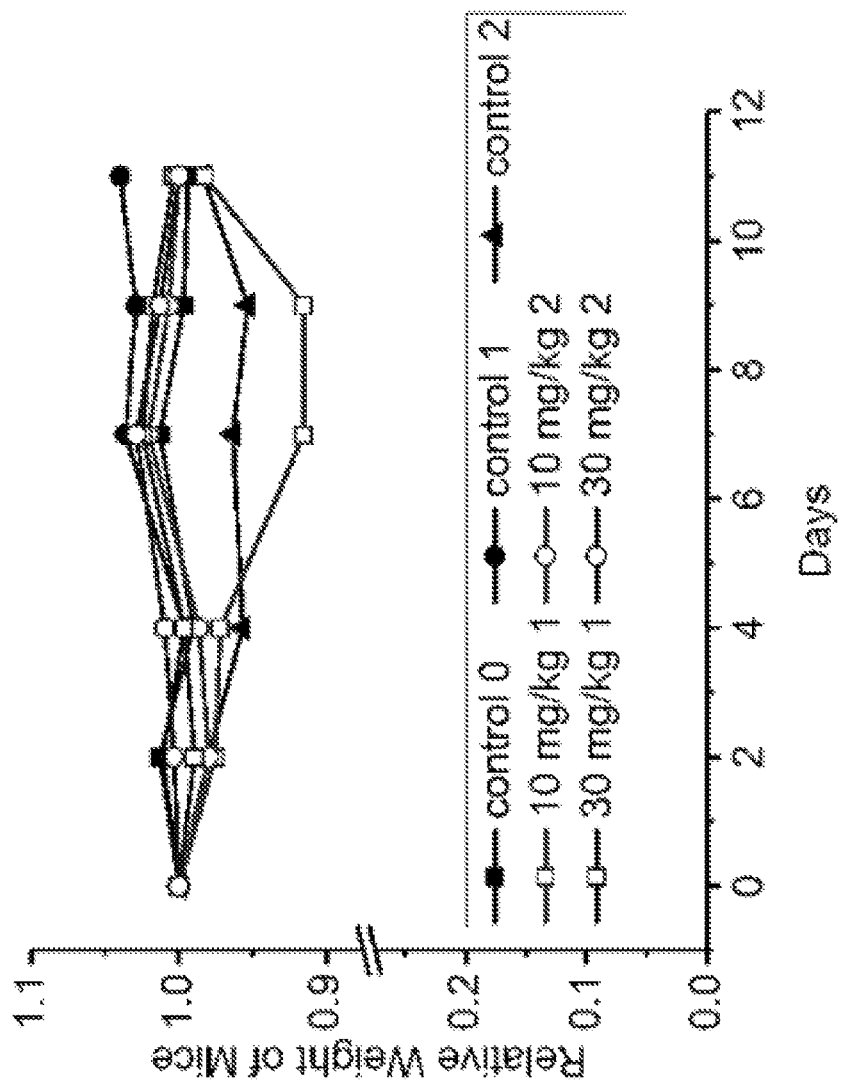
FIG. 7 shows representative data indicating that compound 3 is non-toxic for mice up to a highest tested dose of 30 mg/kg.

15. Compound 3 is Non-Toxic for Mice Up to a Highest Tested Dose of 30 Mg/Kg A pilot toxicity study was performed with three control mice: "control 0" not injected, controls 1 and 2 injected intravenously with the vehicle (5% ethanol, 5% cremophor in water with 5% dextrose [D5W]), two mice treated with 10 mg/kg of compound 3, and two mice treated with 30 mg/kg of the compound. Six injections were performed on Mondays, Wednesdays, and Fridays for two weeks, and the weight and overall condition of the mice were monitored. As shown in FIG. 7, the weight did not differ significantly between the control and treated mice. No differences in the animals' behavior were noted.

Figure 8:
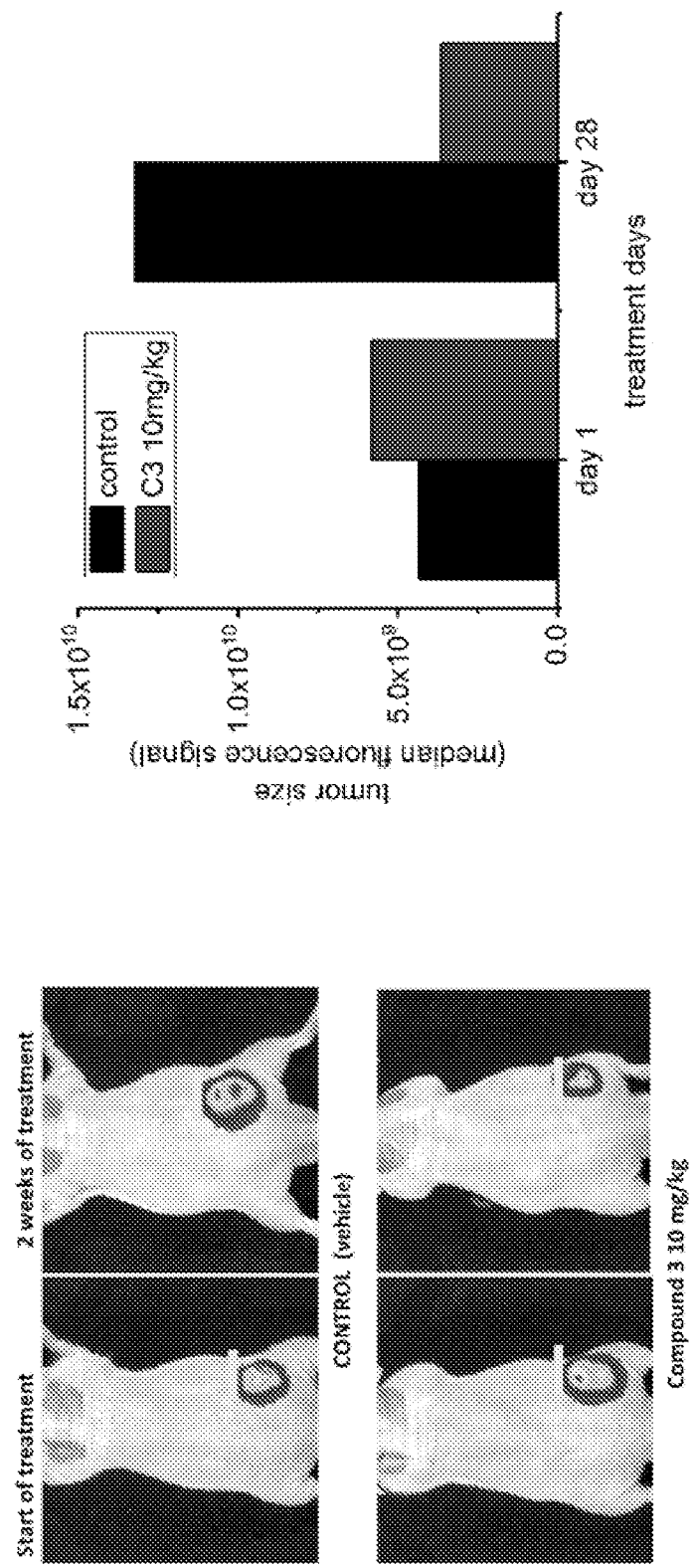
FIG. 8 shows representative data indicating that compound 3 attenuates the growth of the tumor in nude mice xenografted with human prostate cancer PC3 cells.

16. Compound 3 Attenuates the Growth of the Tumor in Nude Mice Xenografted with Human Prostate Cancer PC3 Cells The efficacy study was performed with mice xenografted with human cultured androgen-resistant prostate cancer PC3 cells. To assure efficient monitoring of tumor growth and dissemination, the cells expressing green fluorescent protein (GFP) and luciferine were used for xenografting (Bioware Brite PC3-RedFLuc-GFP). The study involved nineteen nude mice. Tumor-growing mice were treated intra-tumorally (IT) with the vehicle (dimethylsulfoxide; DMSO; 8 control mice) or with 10 mg/kg of compound 3 (10 mice). Injections were carried on Mondays, Wednesdays, and Fridays. To assure accurate assessment of the tumor size, at the time of first and last treatments the mice were injected with luciferine (substrate for luciferase) and the total intensity of fluorescent product was recorded by the Xenogen IVIS Spectrum small animal imager. The imaging method is considered much more accurate than the caliper measurements that can be easily biased by scar tissue in shrinking tumors. Treatment with compound 3 attenuated the growth of xenografted tumor. Referring to FIG. 8 left panel, sample images of control and treated mice are shown. The color scale from blue (lowest) through green, yellow and red (highest) corresponds to the intensity of fluorescence emitted from the tumor and thus represents the total mass of live cancer cells. Referring to FIG. 8 right panel, median ratios of last-to-first total tumor fluorescence values are shown. Apparently, the median tumor size in controls increased nearly three-fold (ratio=3.05), whereas in the treated cohort a tumor shrinkage was recorded instead (ratio=0.62).

17. Compound 3 Attenuates Migration and Proliferation of Cultured

Prostate Cancer PC3 Cells

Figure 9:
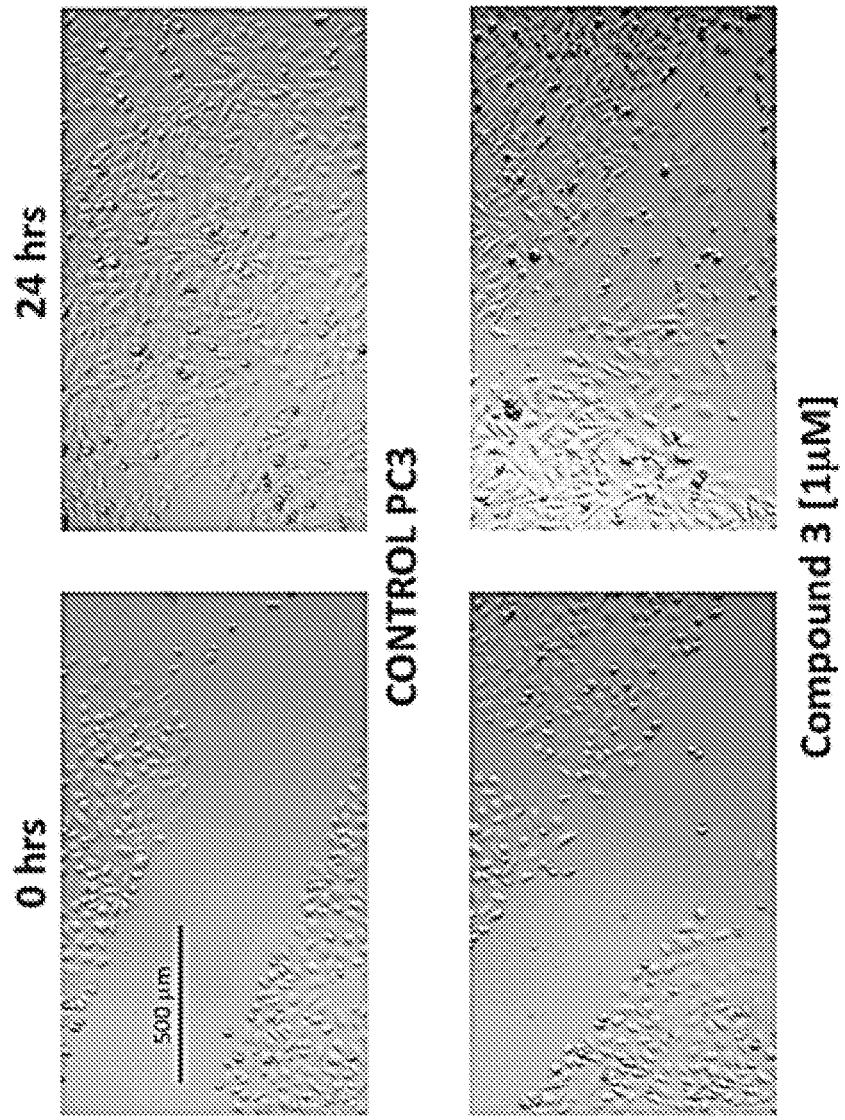
FIG. 9 shows representative data indicating that compound 3 attenuates migration and proliferation of cultured prostate cancer PC3 cells.

The "scratch test" was performed with human cultured androgen-resistant prostate cancer PC3 cells. The surface of growing confluent cells was scratched to produce a 0.5 mm wide gap. The scratch was photographed at time 0 hrs. and the cells were cultured with vehicle (DMSO; 1:1000) or with 1 μM of compound 3. After 24 hrs the scratch in control culture was almost entirely closed. In the cell culture treated with compound 3, the scratch was still visible (see FIG. 9).

Figure 10:
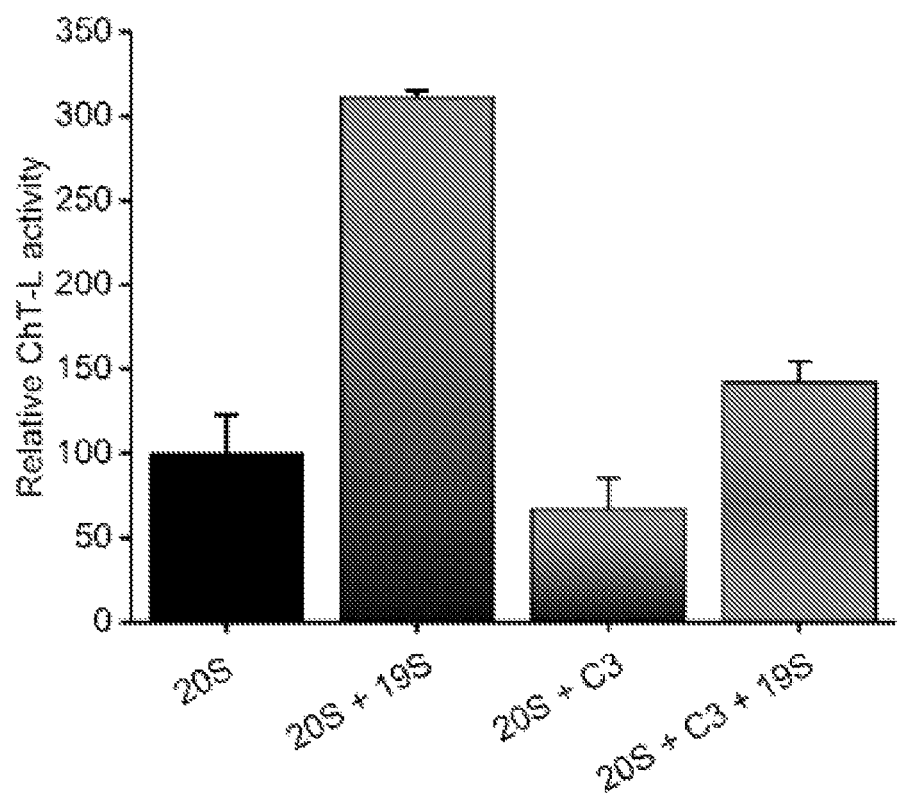
FIG. 10 shows representative data indicating that compound 3 not only inhibits the fully-assembled 26 S proteasome with low-micromolar efficacy, but also prevents activation of the core proteasome by the 19 S regulatory particle.

18. Compound 3 not Only Inhibits the Fully-Assembled 26 S Proteasome with Low-Micromolar Efficacy, but Also Prevents Activation of the Core Proteasome by the 19 S Regulatory Particle The 26 S proteasome can be reconstructed in vitro from the purified core (20 S) and regulatory particle (19 S) protein complexes. Activation of the core is considered a measure of effectiveness of the reconstruction. As shown in FIG. 10, the core was activated about 3-fold with 2:1 molar ratio of 19 S:20 S. Pretreatment (10 minutes, RT) of the 20 S proteasome with a low dose (1 µM) of compound 3 strongly attenuated the activation, by about two-thirds in comparison to 20 S treated with compound c3. The reconstruction was carried out in the presence of ATP (1 mM ATP, 0.5 mM $MgCl_2$, 0.5 mM dithiothreitol), as required for the optimal conditions of the 20 S-19 S binding. Averages and SD from three independent experiments are presented.

Figure 11:
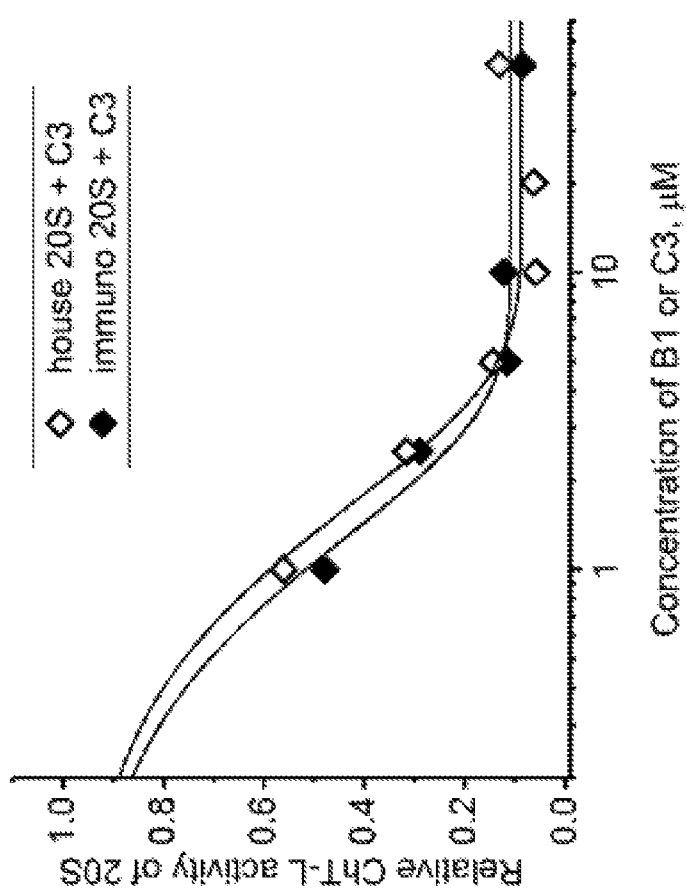
FIG. 11 shows representative data indicating that compound 3 inhibits both housekeeping and immunoproteasomes with similar efficacy.

19. Compound 3 Inhibits Both Housekeeping and Immunoproteasomes with Similar Efficacy Immuno and housekeeping forms are serving distinct physiological functions. The clinically used competitive inhibitors do target them with a similar efficacy; however such outcome is not obvious with allosteric inhibitors such as compound 3. Referring to FIG. 11, the relative activities of the proteasome forms are shown, activated with the Rpt5-derived peptide and treated with compound 3.

Summarizing, the pipecolic ester scaffold emerges as an attractive template for a new class of allosteric proteasome inhibitors that destabilize the α ring and the gate of the core 20 S proteasome, and attenuate the growth of cancer cells.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula selected from:

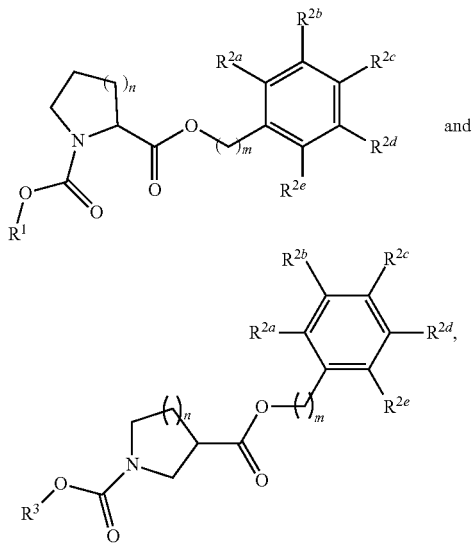

wherein n is 1 or 2;
wherein m is 1, 2, or 3;
wherein $R^1$ is selected from $(CH_2)_qCy^1$, $Cy^1$, and C1-C8 acyclic alkyl substituted with 0, 1, 2, or 3 groups independently selected from halogen, —CN, —$NH_2$, —$NO_2$, —OH, —C(O)$NR^{20a}R^{20b}$, —$CO_2H$, and —$CO_2$(C1-C4 alkyl);
wherein q, when present, is 1, 2, or 3;
wherein each of $R^{20a}$ and $R^{20b}$, when present, is independently selected from hydrogen and C1-C4 alkyl;
wherein $Cy^1$ is selected from cyclohexyl and 6-membered monocyclic aryl, and is substituted with 0, 1, 2, or 3 groups independently selected from halogen, —CN, —$NH_2$, —$NO_2$, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and
wherein each of $R^{2a}$, $R^{2b}$, $R^{2c}$, $R^{2d}$, and $R^{2e}$ is independently selected from hydrogen, halogen, —CN,

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: synthetic construct

<400> SEQUENCE: 1

Lys Asn Met Ser Ile Lys Lys Leu Trp Lys
1               5                   10

—NH₂, —NO₂, —OH, C1-C4 alkyl, C1-C4 haloalkyl, C1-C4 hydroxyalkyl, C1-C4 alkoxy, C1-C4 haloalkoxy, C1-C4 alkylamino, and (C1-C4)(C1-C4) dialkylamino; and wherein R³, when present, is selected from C1-C8 alkyl, (CH₂)qCy¹, and Cy¹, provided at least one of $R^{2a}$, $R^{2b}$, $R^{2c}$, $R^{2d}$, and $R^{2e}$ is —OH, C1-C4 alkoxy, or C1-C4 haloalkoxy, and provided when at least one of $R^{2a}$, $R^{2b}$, $R^{2c}$, $R^{2d}$, and $R^{2e}$ is C1-C4 alkoxy and R¹ is C1-C8 acyclic alkyl, then R¹ is substituted with 1, 2, or 3 groups independently selected from halogen, —CN, —NH₂, —NO₂, —OH, —C(O)NR$^{20a}$R$^{20b}$, —CO₂H, and —CO₂(C1-C4 alkyl), or a pharmaceutically acceptable salt thereof.

2. The compound of claim 1, wherein n is 1.

3. The compound of claim 1, wherein R¹ is selected from (CH₂)qCy¹ and Cy¹.

4. The compound of claim 1, wherein R¹ is CH₂Cy¹.

5. The compound of claim 1, wherein the compound has a structure represented by a formula selected from:

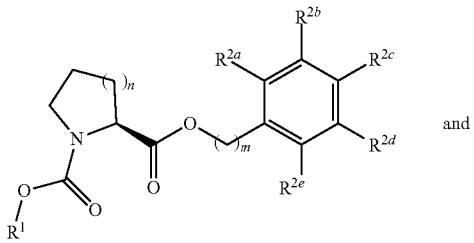 and 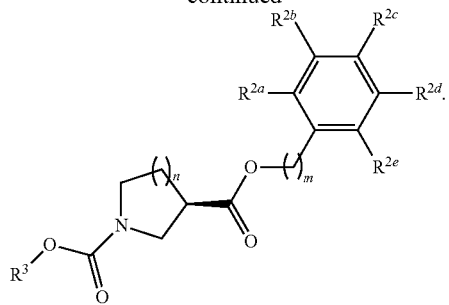

6. The compound of claim 1, wherein the compound has a structure represented by a formula:

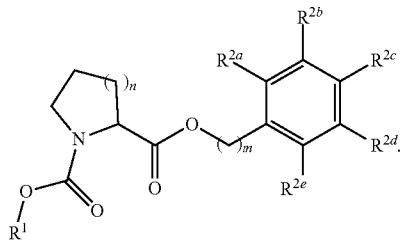

7. A pharmaceutical composition comprising a therapeutically effective amount of at least one compound of claim 1 and a pharmaceutically acceptable carrier.

* * * * *